(12) United States Patent
Giot et al.

(10) Patent No.: US 6,753,314 B1
(45) Date of Patent: Jun. 22, 2004

(54) PROTEIN-PROTEIN COMPLEXES AND METHODS OF USING SAME

(75) Inventors: Loic Giot, East Haven, CT (US); Traci A. Mansfield, Bramford, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/538,092

(22) Filed: Mar. 29, 2000

Related U.S. Application Data

(60) Provisional application No. 60/178,965, filed on Feb. 1, 2000, and provisional application No. 60/127,352, filed on Apr. 1, 1999.

(51) Int. Cl.$^7$ ..................... C07K 14/395; C12N 15/10
(52) U.S. Cl. ................... 514/12; 530/350; 536/23.5; 435/254.21; 435/320.1; 435/252.3; 435/7.1; 435/69.7
(58) Field of Search ................... 514/12; 530/350; 536/23.5; 435/254.21, 320.1, 252.3, 7.1, 69.7

(56) References Cited

FOREIGN PATENT DOCUMENTS

| | | |
|---|---|---|
| WO | WO 99/35256 | 7/1999 |
| WO | WO 00/46406 | 8/2000 |

OTHER PUBLICATIONS

Aneskievich, B. J. and E. Fuchs (1995). "The A/B domain of truncated retinoic acid receptors can block differentiation and promote features of malignancy." *J Cell Sci* 108(Pt 1): 195–205.

Bishop, D. K., Park, et al. (1992). "DMC1: a meiosis–specific yeast homolog of E. coli recA required for recombination, synaptonemal complex formation, and cell cycle progression." *Cell* 69(3): 439–56.

Cvrckova, F. and K. Nasmyth (1993). "Yeast G1 cyclins CLN1 and CLN2 and a GAP–like protein have a role in bud formation." *Embo J* 12(13): 5277–86.

Fabre, E. and E. Hurt (1997). "Yeast genetics to dissect the nuclear pore complex and nucleocytoplasmic trafficking." *Annu Rev Genet* 31: 277–313.

Funakoshi, T., A. Matsuura, et al. (1997). "Analyses of APG13 gene involved in autophagy in yeast, *Saccharomyces cerevisiae*." *Gene* 192(2): 207–13.

Genbank Accession No.: AB007948.

Hollingsworth, N. M., L. Ponte, et al. (1995). "MSH5, a novel MutS homolog, facilitates meiotic reciprocal recombination between homologs in *Saccharomyces cerevisiae* but not mismatch repair." *Genes Dev* 9(14): 1728–39.

Hoyt, M. A., L. Totis, et al. (1991). "*S. cerevisiae* genes required for cell cycle arrest in response to loss microtubule function." *Cell* 66(3): 507–17.

Hwang, L. H., L. F. Lau, et al. (1998). "Budding yeast Cdc20: a target of the spindle checkpoint [see comments] [published erratum appears in Science May 29, 1998;280(5368):1331]." *Science* 279(5353): 1041–4.

Kessler, M. M., M. F. Henry, et al. (1997). "Hrp1, a sequence–specific RNA–binding protein that shuttles between the nucleus and the cytoplasm, is required for mRNA 3'–end formation in yeast." *Genes Dev* 11(19): 2545–56.

Kim, J., S. V. Scott, et al. (1997). "Transport of a large oligomeric protein by the cytoplasm to vacuole protein targeting pathway." *J Cell Biol* 137(3): 609–18.

Nasmyth, K. (1993). "Control of the yeast cell cycle by the Cdc28 protein kinase." *Curr Opin Cell Biol* 5(2): 166–79.

Saul, D. J. and P. E. Sudbery (1985), "Molecular cloning of WH12, a gene involved in the regulation of cell proliferation in *Saccharomyces cerevisiae*." *J Gen Microbiol* 131(Pt 7): 1797–806.

Scott, S. V., A. Hefner–Gravink, et al. (1996). "Cytoplasm–to–vacuole targeting and autophagy employ the same machinery to deliver proteins to the yeast vacuole." *Proc Natl Acad Sci U S A* 93(22): 12304–8.

Scott, S. V. and D. J. Klionsky (1998). "Delivery of proteins and organelles to the vacuole from the cytoplasm." *Curr Opin Cell Biol* 10(4): 523–9.

Singer–Kruger, B., H. Stenmark, et al. (1994). "Role of three rab5–like GTPases, Ypt51p, Ypt52p, and Ypt53p, in the endocytic and vacuolar protein sorting pathways of yeast." *J Cell Biol* 125(2): 283–98.

Taylor, S. S., E. Ha, et al. (1998). "The human homologue of Bub3 is required for kinetochore localization of Bub1 and a Mad3/Bub1–related protein kinase." *J Cell Biol* 142(1): 1–11.

Thumm, M., R. Egner, et al. (1994). "Isolation of autophagocytosis mutants of *Saccharomyces cerevisiae*." *FEBS Lett* 349(2): 275–80.

Tsukada, M. and Y. Ohsumi (1993). "Isolation and characterization of autophagy–defective mutants of *Saccharomyces cerevisiae*." *FEBS Lett* 333(1–2): 169–74.

Usui, T., T. Ohta, et al. (1998). "Complex formation and functional versatility of Mre11 of budding yeast in recombination." *Cell* 95(5): 705–16.

(List continued on next page.)

*Primary Examiner*—Karen Cochrane Carlson
*Assistant Examiner*—Chih-Min Kam
(74) *Attorney, Agent, or Firm*—Ivor R. Elrifi, Esq.; Mintz, Levin, Cohn, Ferris, Glovsky & Popeo, P.C.

(57) ABSTRACT

The invention provides complexes of at least two polypeptides, and methods of using the same. Purified complexes of two polypeptides are provided, including chimeric complexes, and chimeric polypeptides and complexes thereof are also provided, as are nucleic acids encoding chimeric polypeptides and vectors and cells containing the same. Also provided are methods of identifying agents that disrupt polypeptide complexes, methods of identifying complex or polypeptide in a sample, and for removing the same, methods of determining altered expression of a polypeptide in a subject, and methods of treating/preventing disorders involving altered levels of complex or polypeptide.

5 Claims, No Drawings

OTHER PUBLICATIONS

Wigge, P. A., O. N. Jensen, et al. (1998). "Analysis of the Saccharomyces spindle pole by matrix–assisted laser desorption/ionization (MALDI) mass spectrometry." *J Cell Biol* 141(4): 967–77.

Uetz et al., (2000). "A comprehensive analysis of protein–protein interactions in *Saccharomyces cerevisiae*." *Nature* 403: 623–631.

Fromont–Racine, M. et al. (1997). *Nature Genetics 16*: 277–282.

Wodicka, L. et al. (1997). *Nature Biotech. 15*: 1359–1367.

Lecrenier, N. et al. (1998). *Bioessays 20*: 1–5.

Bendixen, C. et al. (1994). *Nuc. Acids Res. 22*:1778–1779.

Luo, Y. et al. (1996). *Biotechniques 20*: 564–568.

Cho, R. et al. (1998). *Proc. of the Natl. Acad. Sci. USA 95*: 3752–3757.

Flores, A. et al. (1999). *Proc. of the Natl. Acad. Sci. USA 96*:7815–7820.

International Search Report, issued Sep. 19, 2000.

US 6,753,314 B1

PROTEIN-PROTEIN COMPLEXES AND METHODS OF USING SAME

RELATED APPLICATIONS

This application claims priority from U.S. Ser. No. 60/127,352, filed Apr. 1, 1999, and U.S. Ser. No. 60/178,965, filed Feb. 1, 2000 ("Human Ortholog Protein Interactions of Yeast Interactions"). The contents of these applications are incorporated by reference in their entirety.

FIELD OF THE INVENTION

The invention relates generally to polypeptides and complexes of two or more polypeptides, as well as to methods of use thereof.

BACKGROUND OF THE INVENTION

Most, if not all, biologically important activities are mediated at the tissue, cellular, and subcellular level at least in part by interactions between one or more proteins. These biologically important activities can include, e.g., cell division, cell differentiation, anabolic activities, and catabolic activities. Interacting proteins or polypeptides can form a complex. Accordingly, failure to form a given polypeptide complex can result in deleterious consequences to a cell or individual. Conversely, the inappropriate formation of a given polypeptide complex can likewise be undesirable.

The identification of protein complexes associated with specific biological activities can be used to identify or prevent conditions associated with the absence or presence of these complexes.

SUMMARY OF THE INVENTION

The invention is based, in part, upon the identification of protein-protein interactions in the yeast S. cerevisiae and humans. Interacting proteins present in complexes according to the invention are shown in, e.g., Table 3.

In one aspect, the invention provides a purified complex including a first polypeptide that includes the amino acid sequence encoded by the open reading frame ("ORF") listed in Table 3, column 1, and a second polypeptide that includes the amino acid sequence of the corresponding polypeptide encoded by the ORF recited in column 5 of Table 3. Gene names for the ORFs recited in Table 3, column 1, and Table 3, column 5 are provided in Table 3, columns 2 and 6, respectively.

In another aspect, the invention provides a purified complex including a first polypeptide and a second polypeptide selected from, or including, the human polypeptides recited in Table 7, column 2, and the corresponding polypeptides recited in Table 7, column 6. Complexes of polypeptides including the binding domains of such polypeptides, and complexes having labeled polypeptide, are also provided.

The invention also provides purified complexes of a first and a second polypeptide. The first polypeptide is a polypeptide functionally classified in the MIPS database as a Cell/Growth/Cell Division/DNA Synthesis protein; a Cell Rescue/Cell Defense/Cell Death and Aging Protein; a Cellular Biogenesis protein; a Cellular Organization protein; a Classification Not-Yet Clear Cut protein; an Energy Protein; an Intracellular Transport protein; an Ionic Homeostasis protein, a Metabolism protein; a Protein Destination protein; a Protein Synthesis protein; a Retrotransposon/Plasmid protein; a Signal Transduction protein; a Transcription protein; a Transport Facilitation protein, or an Unclassified protein. The second polypeptide is the corresponding polypeptide recited in Table 3, column 5 or Table 7, column 6, respectively.

The invention also provides a purified complex of a first and second polypeptide, where at least one of the polypeptides is a microtubule or microtubule-associated protein, a heme biosynthesis protein, or a cell wall or cell-wall synthesis protein.

The invention further provides purified chimeric complexes including a yeast polypeptide and a human ortholog polypeptide. In some embodiments the yeast polypeptide includes the amino acid sequence of the polypeptides recited in Table 7, column 1, and the human polypeptide includes the amino acid sequence of the corresponding polypeptides recited in Table 7, column 6. In other embodiments the yeast polypeptide is selected from, or includes, the polypeptides recited in Table 7, column 5, and the human ortholog polypeptide is selected from, or includes, the polypeptides recited in Table 7, column 2.

In a further aspect, the invention provides chimeric polypeptides having six or more amino acids of a first polypeptide covalently linked to six or more amino acids of a second polypeptide. In some embodiments, the chimeric polypeptides are yeast-yeast chimeras, while in others the chimeric polypeptides are human-human or yeast-human chimera. In some embodiments, the first polypeptide is selected from the polypeptides recited in Table 3, column 1, and the second polypeptide is selected from the polypeptides recited in Table 3, column 5. In other embodiments, the first polypeptide is selected from polypeptides recited in Table 7, columns 1 or 2, and the second polypeptide is selected from the polypeptides recited in Table 7, columns 5 or 6. Nucleic acids encoding chimeric polypeptides, and vectors and cells containing the same, are also provided.

In yet another aspect, the invention provides an antibody which specifically binds polypeptide complexes according to the invention. The antibody preferably binds to a complex comprising one or more polypeptides with greater affinity than its affinity for either polypeptide that is not present in the complex.

Also provided by the invention are kits containing reagent which can specifically detect the complexes of the invention. In one embodiment, the reagent is a complex-specific antibody, while in other embodiments the reagent is an antibody specific for the first or second polypeptides of the complex.

In another aspect, the invention provides pharmaceutical compositions including the complexes described herein. Such compositions are formulated to be suitable for therapeutic administration in the treatment of deficiencies or diseases involving altered levels of the complexes of the invention.

In still another aspect, the invention provides methods of identifying an agent which disrupts a polypeptide complex by providing a complex described herein, contacting the complex with a test agent, and detecting the presence of a polypeptide displaced from the complex. In certain embodiments, the complex includes at least one polypeptide comprising a microtubule or microtubule-associated protein, a heme biosynthesis protein, or a cell wall or cell-wall synthesis protein.

In a further aspect, the invention provides a method for inhibiting the interaction of a protein with a ligand by contacting a complex of the protein and ligand with an agent that disrupts the complex. In certain embodiments, the protein is a microtubule or microtubule associated protein, a heme biosynthesis protein, or a cell wall or cell-wall synthesis protein, and the ligand is a corresponding interacting polypeptide described herein.

In yet another aspect, the invention provides a method of identifying a polypeptide complex in a subject by providing a biological sample from the subject and detecting, if present, the level of a complex, described herein, in the subject.

Also provided by the invention is a method for detecting a polypeptide in a biological sample by providing a biological sample containing a first polypeptide, and contacting the sample with a second polypeptide under conditions suitable to form a polypeptide complex.

In another aspect, the invention provides a method for removing a first polypeptide from a biological sample by providing a biological sample including the first polypeptide, contacting the sample with a second polypeptide under conditions suitable for formation of a polypeptide complex, and removing the complex, thereby effectively removing the first polypeptide. In certain embodiments, the first polypeptide is selected from, or includes, the polypeptides recited in Table 7, column 2, and the second polypeptide is selected from, or includes, the polypeptides recited in Table 7, column 6. In another embodiment, the first polypeptide is selected from, or includes, the polypeptides recited in Table 7, column 6, and the second polypeptide is selected from, or includes, the polypeptides recited in Table 7, column 2.

In a further aspect, the invention provides a method for determining altered expression of a polypeptide in a subject by providing a biological sample from the subject, measuring the level of polypeptide complex in the sample, and comparing the level of the complex in the sample to the level of complex in a reference sample with a known polypeptide expression level.

In a still further aspect, the invention provides a method of treating or preventing a disease or disorder involving altered levels of a complex described herein or a polypeptide described herein, by administering, to a subject in need thereof, a therapeutically-effective amount of at least one molecule that modulates the function of the complex or polypeptide. In one embodiment, the agent modulates the function of a polypeptide selected from the polypeptides recited in Table 7, columns 2 or 6.

In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference herein in their entirety.

DETAILED DESCRIPTION OF THE INVENTION

The invention provides complexes of interacting polypeptides which have not heretofore been shown to interact directly, as well as methods of using these complexes.

Some interacting polypeptides were identified by identifying which of the predicted open-reading frames (ORFs) of the yeast S. cerevisiae encode polypeptides that interact in a yeast two-hybrid system. In one screen, 692 discrete interacting protein pairs were discovered. These interacting pairs include (i) interactions that place functionally unclassified proteins in a biological context, (ii) novel interactions between proteins involved in the same biological function, and (iii) novel interactions that link together biological functions into larger cellular processes.

A summary of the screening used to identify interacting yeast ORFS is shown in Table 1.

TABLE 1

Screen Summary

| Description | Total |
|---|---|
| Yeast ORF PCR Products | 6144 |
| Yeast ORFs cloned[a] | 5345 |
| ORFs pooled to generate the activation domain library | 5341[b] |
| Yeast ORFs identified to have interactions[c] | 817 |
| Total discrete interacting protein pairs | 692 |
| Interactions identified in independent experiments[d] | 286 |
| Interactions identified multiple times in a single experiment | 186 |
| Interactions identified only once | 220 |

[a]Number of PCR products giving transformants in both plasmids (pOBD2 and pOAD).
[b]One yeast ORF activation domain construct was excluded from the pool due to self-activation in a test screen (YJR009C - glyceraldehyde-3-phosphate dehydrogenase and YNL333W - Snz2) and three yeast ORF activation domain constructs were excluded because they encoded proteins that could affect the selection process (YPL248C - Gal4, YML051W - Gal80 and YEL021W - Ura3).
[c]The total number of yeast ORFs found as an interacting binding domain clone and/or an interacting activation domain clone in the screens.
[d]All screening experiments were performed in duplicate.

Table 2 indicates that the interacting proteins disclosed herein can be grouped by functional roles using the Munich Information Center for Protein Sequences ("MIPS") classification system.

TABLE 2

Interactions grouped by Protein Functional Roles (as classified by the MIPS database)[a]

| MIPS classification | MIPS Classification Proteins in Category[b] | Results from the screen | | |
|---|---|---|---|---|
| | | Proteins with Interactions[c] | Total Interactions | Interactions within a Category |
| Metabolism | 1023 | 133 | 189 | 40 |
| Energy | 239 | 29 | 39 | 3 |
| Cell Growth, Cell Division and DNA Synthesis | 767 | 138 | 227 | 46 |
| Transcription | 734 | 134 | 185 | 38 |
| Protein Synthesis | 345 | 18 | 37 | 5 |
| Protein Destination | 525 | 76 | 98 | 15 |
| Transport Facilitation | 302 | 14 | 20 | 0 |
| Intracellular Transport | 438 | 50 | 99 | 8 |
| Cellular Biogenesis | 185 | 23 | 35 | 3 |
| Signal Transduction | 122 | 25 | 32 | 4 |
| Cell Rescue, Defense, Cell Death and Aging | 341 | 48 | 69 | 7 |
| Ionic Homeostasis | 120 | 8 | 18 | 0 |
| Cellular Organization | 2144 | 290 | 388 | 130 |
| Retrotransposons and Plasmid Proteins[d] | 113 | 1 | 1 | 0 |
| Classification Not Yet Clear-Cut | 151 | 22 | 42 | 1 |
| Unclassified Proteins | 2593 | 313 | 388 | 110 |

[a]In the MIPS database, proteins have been classified into at least one category, and one third of proteins have been placed in more than one category. See MIPS Yeast Genome Database (MYGD) Functional Catalogue [www.mips.biochem.mpg.de/proj/yeast], Mewes et al., Nucl. Acid Res. 25:28 (1997); Mewes et al., Nucl. Acid. Res. 26:33 (1998).
[b]Numbers based on 6234 ORFs.
[c]Total based on 885 ORFs. Total interactions with at least one protein in the category.
[d]Only eight of the yeast ORFs in this category were contained in the original 6144 ORF screening population.

Some newly disclosed interactions place functionally unclassified proteins from the yeast genome in a biological context. For example, two proteins of unknown function, YGR010Wp and YLR328Wp (77% identical), were observed to interact with each other, and also to bind to ornithine aminotransferase (Car2p), which catalyzes a step in arginine metabolism. This observation suggests that YGR010WP and YLR328Wp are implicated in arginine metabolism. In addition, because YGR010Wp and YLR328Wp are 40% identical to the human protein KIAA0479 (Genbank accession number AB007948), the interactive data further suggest that the human protein KIAA0479 is also involved in arginine metabolism.

Also included in the interactions are complexes of two or more proteins involved in functional pathways for which direct interactions have not been described previously. For example, proteins involved in autophagy, e.g., Apg13p, are shown herein to interact with proteins of the Cvt (cytoplasm-to-vacuole targeting) pathway, e.g., Lap4p. Previously, direct interactions between proteins involved in autophagy and the Cvt pathway had not been reported. Autophagy is a degradation pathway used under conditions of nutrient stress to non-selectively recycle cytoplasmic proteins and organelles to their constituent components, while the Cvt pathway is a biosynthetic pathway that transports the vacuolar enzyme aminopeptidase I (API, encoded by LAP4) specifically to the vacuole. See Scott et al., *Curr. Opin. Cell. Biol.* 10: 523 (1998). Several mutants in the Cvt pathway (cvt) and autophagocytosis (aut and apg) are allelic, suggesting that both pathways utilize some of the same molecular components. See Tsukada et al., *FEBS Letters* 333: 169 (1993); Thumm et al., *FEBS Letters* 349: 275 (1994); Harding et al., *J. Cell. Biol.* 131: 17621 (1996); Scott et al., *Proc. Natl. Acad. Sci. USA* 93: 12304 (1996).

A number of ORFs encoding proteins of unknown functions have been identified as components of autophagy. Since several of the genes altered in apg, aut, and cvt mutants have not yet been cloned, ORFs found in these interactions can be examined to determine if they encode any of these altered genes. It has also been shown that Lap4p is a self-interactor, corroborating previous evidence that Lap4p assembles into a dodecamer (see Funakoshi et al., *Gene* 192: 207 (1997)), and the observed interaction between Apg1 and Apg13 lends support to previous genetic evidence suggesting that APG1 is a high-copy suppressor of apg13 (Kim et al, *J. Cell. Biol.* 137: 609 (1997)).

An interaction was also identified between YDR201 Wp and YKR037Cp, two proteins known to be localized to the spindle pole body by mass spectrometry. See Wigge et al., *J. Cell Biol.* 141: 967 (1998). The interaction of these proteins may indicate their involvement in the regulation of mitotic events.

New insights into novel interactions between proteins involved in the same biological function are also provided. For example, the nuclear polyadenylated RNA-binding proteins Nab2p and Nab4p bind to the 3' end of mRNA, but have distinct roles. See Kessler et al., *Genes Dev.* 11: 2545 (1997). Nab2p is required for the regulation of poly(A) tail length and export of mRNA from the nucleus, and Nab4p is essential for the cleavage of pre-mRNA at the correct 3' site. The newly described interaction between Nab2p and Nab4p suggests that they may act in concert.

Similarly, in yeast, diverse cyclins bind to Cdc28p in a coordinated manner to modulate its kinase activity during the cell cycle. The B-type cyclins play a critical role in the induction of bipolar mitotic spindle formation. See Nasmyth, *Curr. Opin. Cell. Biol.* 5: 166 (1993). Each of the B-type cyclins, Clb1p, Clb2p and Clb3p, has presently been observed to form a complex with Cks1p and Cdc28p. The identification of interactions between Cks1p and each of Clb1p, Clb2p and Clb3p, suggests that the kinase activity of Cdc28p could be mediated by cyclin Bs through their interaction with Cks1p.

In another example, Ypt53p, a rab5-like GTPase involved in vacuolar protein sorting and endocytosis, has presently been shown to interact with Siw4p, a putative tyrosine phosphatase which acts in a complex to control nutrient-dependent cell proliferation. See Singer-Kruger et al., *J. Cell. Biol.* 125: 283 (1994); Saul et al., *Gen. Microbiol.* 131: 1797 (1985). One possible explanation for the observed interaction is that Ypt53p senses nutrient availability to coordinate cell cycle progression.

The newly identified protein-protein interactions connect biological functions into larger cellular processes. For example, the nuclear pore complex (NPC), consisting of as many as 50 different subunits, is the macromolecular-conducting channel between the nucleus and the cytoplasm. See Fabre et al., *Ann. Rev. Genet.* 31: 277 (1997); Marelli et al., *J. Cell Biol.* 143: 1813 (1998). Two newly identified NPC components, Nup53p and Nup59p/Asm4p, interact with Ndc1p, a protein required for spindle pole body (SPB) duplication and component of the nuclear envelope. Evidence of a physical interaction between components of the NPC and SPB suggests that these two structures located in the nuclear envelope may coordinate communication between the nucleus and the cytoplasm.

Another interaction involves the meiosis-specific protein, Msh5p, which is required for the resolution of cross-overs during meiosis. Hollingsworth et al., *Genes Dev.* 9: 1728 (1995). Meiotic recombination is initiated by double-strand breaks (DSBs), a prerequisite to cross-over formation that is resolved in a structure called the synaptonemal complex (SC). Mre11p is part of a complex that participates in DSB formation. See Usui et al., *Cell* 95: 705 (1998). It is also known that Tid3p helps form the spindle pole body and interacts with Dmc1p, a protein required for the formation of the SC. See Bishop et al., Cell 69: 439–56 (1992). It has presently been shown that Msh5p interacts with both Mre11p and Tid3p. These novel associations tie DSB formation and the resolution of cross-overs with Msh5p as the linking protein.

Similarly, to exit the cell cycle, cells must undergo a series of checkpoints that monitor correct microtubule and spindle formation. See Guenette et al., *J. Cell. Sci.* 108: 195 (1995). The present invention identifies at least two interactions that tie cycle regulation to microtubule assembly. The first is between a microtubule checkpoint protein, Bub3p and a spindle pole body checkpoint protein, Mad3p. This observation mirrors the recent interaction described between the human homologs of Bub3p and Mad3p. See Hoyt et al., *Cell* 66: 507–17 (1991); Hwang et al., *Science* 279. 1041 (1998); Taylor et al., *J. Cell Biol.* 142: 1 (1998). Interestingly, the second is between Mad3p and a known regulator of the Cdc28p kinase, Cln3p, See Cvrckova et al., *EMBO J.* 12: 5277 (1993). These interactions could give rise to a cascade Bub3→Mad3→Cln3p→Cdc28p, and may suggest a pathway to propagate the signal of incorrect microtubule formation during early events at the cell cycle arrest in G1 phase.

The complexes disclosed herein are useful, inter alia, in identifying agents which modulate cellular processes in which one or more members of the complex have previously been associated. For example, interacting Pro-Pairs 1a–1b (representing open reading frames YGR108W and YBR135W, or genes CLB1 and CKS1, respectively) as shown in Table 3, have both been previously implicated in cell growth, cell division, and/or DNA synthesis.

Accordingly, new agents which modulate cell growth, cell division, and/or DNA synthesis can be identified by evaluating the ability of a test agent to affect formation or dissolution of a complex of the Pro-Pairs 1a and 1b.

Complexes according to the invention can also be used in methods for identifying a desired polypeptides in a biological sample by forming a complex of a first polypeptide and a second polypeptide that interacts with the first polypeptide. The presence of the complex indicates that the sample contains the first polypeptide.

These utilities, as well as additional utilities, are discussed in greater detail below Purified Polypeptide Complexes In one aspect, the invention includes a purified complex that includes two or more polypeptides. In one embodiment, the invention provides purified complexes of two or more polypeptides. One of the polypeptides includes a polypeptide selected from the polypeptides recited in Table 3, column 1 (referenced as ProPair 1a–692a) and another includes a polypeptide selected from the polypeptides recited in Table 3, column 5 (referenced as ProPair 1b–692b). In some embodiments the first and second polypeptides of the complex are the polypeptides enumerated in Table 3. In some embodiments a first polypeptide is listed as a "bait" polypeptide and a second polypeptide is denoted as "prey" polypeptide while in other embodiments the first polypeptide corresponds to a "prey" polypeptide and the second is a "bait" polypeptide.

By "corresponding polypeptide" is meant, with reference to Tables 3–7, the polypeptide recited in the same row, reading across from left-to-right or right-to-left, as a specific selected peptide. For example, in Table 3, in the first row, the corresponding polypeptide of YGR108W is YBR135W. These protein pairs are designated as 1a and 1b, as is indicated in Table 3.

Similarly, in the first row, the corresponding polypeptide of YBR135W (ProPair 1b) is YBR108W. (ProPair 1a). In the second row, however, the corresponding polypeptide of YBR135W (a prey protein; ProPair 2b) is YPR119W (a bait protein; ProPair 2a).

Also as used herein, "protein" and "protein complex" are used synonymously with "polypeptide" and "polypeptide complex." A "purified" polypeptide, protein or biologically active portion thereof is substantially free of cellular material or other contaminating proteins from the cell or tissue source from which the polypeptide is derived, or substantially free from chemical precursors or other chemicals when chemically synthesized. The language "substantially free of cellular material" includes preparations of protein in which the protein is separated from cellular components of the cells from which it is isolated or recombinantly produced. In one embodiment, the language "substantially free of cellular material" includes preparations of polypeptide complex having less than about 30% (by dry weight) of non-complex proteins (also referred to herein as a "contaminating protein"), more preferably less than about 20% of contaminating protein, still more preferably less than about 10% of contaminating protein, and most preferably less than about 5% non-complex protein. When the polypeptide or complex is recombinantly produced, it is also preferably substantially free of culture medium, i.e., culture medium represents less than about 20%, more preferably less than about 10%, and most preferably less than about 5% of the volume of the protein preparation.

TABLE 3

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YGR108W | CLB1 | 1a | Cell Growth, Cell Division And DNA Synthesis; | YBR135W | CKS1 | 1b | Cell Growth, Cell Division And DNA Synthesis; |
| YPR119W | CLB2 | 2a | Cell Growth, Cell Division And DNA Synthesis; | YBR135W | CKS1 | 2b | Cell Growth, Cell Division And DNA Synthesis; |
| YDL155W | CLB3 | 3a | Cell Growth, Cell Division And DNA Synthesis; | YBR135W | CKS1 | 3b | Cell Growth, Cell Division And DNA Synthesis; |
| YDR206W | EBS1 | 4a | Cell Growth, Cell Division And DNA Synthesis; | YJL030W | MAD2 | 4b | Cell Growth, Cell Division And DNA Synthesis; |
| YDR206W | EBS1 | 5a | Cell Growth, Cell Division And DNA Synthesis; | YBR057C | MUM2 | 5b | Cell Growth, Cell Division And DNA Synthesis; |
| YGL175C | SAE2 | 6a | Cell Growth, Cell Division And DNA Synthesis; | YGL175C | SAE2 | 6b | Cell Growth, Cell Division And DNA Synthesis; |
| YGL229C | SAP4 | 7a | Cell Growth, Cell Division And DNA Synthesis; | YJL030W | MAD2 | 7b | Cell Growth, Cell Division And DNA Synthesis; |
| YOR026W | BUB3 | 8a | Cell Growth, Cell Division And DNA Synthesis; | YJL013C | MAD3 | 8b | Cell Growth, Cell Division And DNA Synthesis; Cellular Organization; |
| YGL229C | SAP4 | 9a | Cell Growth, Cell Division And DNA Synthesis; | YJL013C | MAD3 | 9b | Cell Growth, Cell Division And DNA Synthesis; Cellular Organization; |
| YDL127W | PCL2 | 10a | Cell Growth, Cell Division And DNA Synthesis; | YDR146C | SWI5 | 10b | Cell Growth, Cell Division And DNA Synthesis; Transcription; Cellular Organization; |
| YDR108W | GSG1 | 11a | Cell Growth, Cell Division And DNA Synthesis; | YGR234W | YHB1 | 11b | Cell Rescue, Defense, Cell Death And Aging; Cellular Organization; |
| YDR099W | BMH2 | 12a | Cell Growth, Cell Division And DNA Synthesis; | YBL043W | ECM13 | 12b | Cellular Biogenesis; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YOL034W | | 13a | Cell Growth, Cell Division And DNA Synthesis; | YMR117C | | 13b | Cellular Organization; |
| YER180C | ISC10 | 14a | Cell Growth, Cell Division And DNA Synthesis; | YGL026C | TRP5 | 14b | Metabolism; Cellular Organization; |
| YGL229C | SAP4 | 15a | Cell Growth, Cell Division And DNA Synthesis; | YBR196C | PGI1 | 15b | Metabolism; Energy; Cellular Organization; |
| YGL158W | RCK1 | 16a | Cell Growth, Cell Division And DNA Synthesis; | YLR113W | HOG1 | 16b | Metabolism; Signal Transduction; Cell Rescue, Defense, Cell Death And Aging; |
| YDR206W | EBS1 | 17a | Cell Growth, Cell Division And DNA Synthesis; | YER027C | GAL83 | 17b | Metabolism; Transcription; |
| YDR206W | EBS1 | 18a | Cell Growth, Cell Division And DNA Synthesis; | YOR047C | STD1 | 18b | Metabolism; Transcription; |
| YPR119W | CLB2 | 19a | Cell Growth, Cell Division And DNA Synthesis; | YNL135C | FPR1 | 19b | Protein Destination; Cellular Organization; |
| YDR206W | EBS1 | 20a | Cell Growth, Cell Division And DNA Synthesis; | YOL149W | DCP1 | 20b | Transcription; |
| YLR117C | SYF3 | 21a | Cell Growth, Cell Division And DNA Synthesis; | YBR188C | NTC20 | 21b | Transcription; |
| YFL035C | MOB2 | 22a | Cell Growth, Cell Division And DNA Synthesis; | YOL036W | | 22b | Unclassified Proteins; |
| YDR099W | BMH2 | 23a | Cell Growth, Cell Division And DNA Synthesis; | YNL042W | | 23b | Unclassified Proteins; |
| YPR119W | CLB2 | 24a | Cell Growth, Cell Division And DNA Synthesis; | YDR386W | MUS81 | 24b | Unclassified Proteins; |
| YPR119W | CLB2 | 25a | Cell Growth, Cell Division And DNA Synthesis; | YDR412W | | 25b | Unclassified Proteins; |
| YPR119W | CLB2 | 26a | Cell Growth, Cell Division And DNA Synthesis; | YHR035W | | 26b | Unclassified Proteins; |
| YPR119W | CLB2 | 27a | Cell Growth, Cell Division And DNA Synthesis; | YNR022C | | 27b | Unclassified Proteins; |
| YPR046W | MCM16 | 28a | Cell Growth, Cell Division And DNA Synthesis; | YJR135C | MCM22 | 28b | Unclassified Proteins; |
| YOR127W | RGA1 | 29a | Cell Growth, Cell Division And DNA Synthesis; | YHL042W | | 29b | Unclassified Proteins; |
| YOR127W | RGA1 | 30a | Cell Growth, Cell Division And DNA Synthesis; | YJL185C | | 30b | Unclassified Proteins; |
| YGL175C | SAE2 | 31a | Cell Growth, Cell Division And DNA Synthesis; | YCR086W | | 31b | Unclassified Proteins; |
| YGL229C | SAP4 | 32a | Cell Growth, Cell Division And DNA Synthesis; | YJL178C | | 32b | Unclassified Proteins; |
| YGL229C | SAP4 | 33a | Cell Growth, Cell Division And DNA Synthesis; | YJL211C | | 33b | Unclassified Proteins; |
| YGL229C | SAP4 | 34a | Cell Growth, Cell Division And DNA Synthesis; | YMR181C | | 34b | Unclassified Proteins; |
| YGL229C | SAP4 | 35a | Cell Growth, Cell Division And DNA Synthesis; | YOR062C | | 35b | Unclassified Proteins; |
| YGL229C | SAP4 | 36a | Cell Growth, Cell Division And DNA Synthesis; | YPR040W | | 36b | Unclassified Proteins; |
| YMR096W | SNZ1 | 37a | Cell Growth, Cell Division And DNA Synthesis; | YMR095C | SNO1 | 37b | Unclassified Proteins; |
| YHR014W | SPO13 | 38a | Cell Growth, Cell Division And DNA Synthesis; | YHR185C | | 38b | Unclassified Proteins; |
| YLR215C | | 39a | Cell Growth, Cell Division And DNA Synthesis; | YLR386W | | 39b | Unclassified Proteins; |
| YDR076W | RAD55 | 40a | Cell Growth, Cell Division And DNA Synthesis; Cell Rescue, Defense, Cell Death And Aging; Cellular Organization; | YER095W | RAD51 | 40b | Cell Growth, Cell Division And DNA Synthesis; Cell Rescue, Defense, Cell Death And Aging; Cellular Organization; |
| YOR368W | RAD17 | 41a | Cell Growth, Cell Division And DNA Synthesis; Cell Rescue, Defense, Cell Death And Aging; | YLR288C | MEC3 | 41b | Cell Growth, Cell Division And DNA Synthesis; Cellular Biogenesis; Cell Rescue, Defense, Cell Death And Aging; |
| YPL204W | HRR25 | 42a | Cell Growth, Cell Division And DNA Synthesis; Cell Rescue, Defense, Cell Death And Aging; Cellular Organization; | YHR185C | | 42b | Unclassified Proteins; |
| YJL160C | | 43a | Cell Growth, Cell Division And DNA Synthesis; Cell Rescue, Defense, Cell Death And Aging; | YCR059C | | 43b | Unclassified Proteins; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YPL140C | MKK2 | 44a | Cell Growth, Cell Division And DNA Synthesis; Cellular Biogenesis; Signal Transduction; Cell Rescue, Defense, Cell Death And Aging; | YHR030C | SLT2 | 44b | Cell Growth, Cell Division And DNA Synthesis; Signal Transduction; Cell Rescue, Defense, Cell Death And Aging; |
| YLR288C | MEC3 | 45a | Cell Growth, Cell Division And DNA Synthesis; Cellular Biogenesis; Cell Rescue, Defense, Cell Death And Aging; | YMR159C | SAP18 | 45b | Unclassified Proteins; |
| YGR014W | MSB2 | 46a | Cell Growth, Cell Division And DNA Synthesis; Cellular Organization; | YJL030W | MAD2 | 46b | Cell Growth, Cell Division And DNA Synthesis; |
| YDL154W | MSH5 | 47a | Cell Growth, Cell Division And DNA Synthesis; Cellular Organization; | YBR133C | HSL7 | 47b | Cell Growth, Cell Division And DNA Synthesis; |
| YDL154W | MSH5 | 48a | Cell Growth, Cell Division And DNA Synthesis; Cellular Organization; | YMR224C | MRE11 | 48b | Cell Growth, Cell Division And DNA Synthesis; Cellular Biogenesis; Cell Rescue, Defense, Cell Death And Aging; Cellular Organization; |
| YAL040C | CLN3 | 49a | Cell Growth, Cell Division And DNA Synthesis; Cellular Organization; | YJL013C | MAD3 | 49b | Cell Growth, Cell Division And DNA Synthesis; Cellular Organization; |
| YPL049C | DIG1 | 50a | Cell Growth, Cell Division And DNA Synthesis; Cellular Organization; | YDR480W | DIG2 | 50b | Cell Growth, Cell Division And DNA Synthesis; Cellular Organization; |
| YER179W | DMC1 | 51a | Cell Growth, Cell Division And DNA Synthesis; Cellular Organization; | YER179W | DMC1 | 51b | Cell Growth, Cell Division And DNA Synthesis; Cellular Organization; |
| YIL150C | DNA43 | 52a | Cell Growth, Cell Division And DNA Synthesis; Cellular Organization; | YGL201C | MCM6 | 52b | Cell Growth, Cell Division And DNA Synthesis; Cellular Organization; |
| YGR014W | MSB2 | 53a | Cell Growth, Cell Division And DNA Synthesis; Cellular Organization; | YJL013C | MAD3 | 53b | Cell Growth, Cell Division And DNA Synthesis; Cellular Organization; |
| YHR184W | SSP1 | 54a | Cell Growth, Cell Division And DNA Synthesis; Cellular Organization; | YHR184W | SSP1 | 54b | Cell Growth, Cell Division And DNA Synthesis; Cellular Organization; |
| YDR388W | RVS167 | 55a | Cell Growth, Cell Division And DNA Synthesis; Cellular Organization; | YCR009C | RVS161 | 55b | Cell Growth, Cell Division And DNA Synthesis; Intracellular Transport; Cellular Organization; |
| YGR014W | MSB2 | 56a | Cell Growth, Cell Division And DNA Synthesis; Cellular Organization; | YDL165W | CDC36 | 56b | Cell Growth, Cell Division And DNA Synthesis; Transcription; Cellular Organization; |
| YDL154W | MSH5 | 57a | Cell Growth, Cell Division And DNA Synthesis; Cellular Organization; | YGL025C | PGD1 | 57b | Cell Growth, Cell Division And DNA Synthesis; Transcription; Cellular Organization; |
| YMR139W | RIM11 | 58a | Cell Growth, Cell Division And DNA Synthesis; Cellular Organization; | YJR094C | IME1 | 58b | Cell Growth, Cell Division And DNA Synthesis; Transcription; Cellular Organization; |
| YML031W | NDC1 | 59a | Cell Growth, Cell Division And DNA Synthesis; Cellular Organization; | YDL088C | ASM4 | 59b | Cell Rescue, Defense, Cell Death And Aging; |
| YDL017W | CDC7 | 60a | Cell Growth, Cell Division And DNA Synthesis; Cellular Organization; | YGR099W | TEL2 | 60b | Cellular Organization; |
| YGR014W | MSB2 | 61a | Cell Growth, Cell Division And DNA Synthesis; Cellular Organization; | YIL144W | TID3 | 61b | Cellular Organization; |
| YDL154W | MSH5 | 62a | Cell Growth, Cell Division And DNA Synthesis; Cellular Organization; | YIL144W | TID3 | 62b | Cellular Organization; |
| YDL017W | CDC7 | 63a | Cell Growth, Cell Division And DNA Synthesis; Cellular Organization; | YKL039W | PTM1 | 63b | Classification Not Yet Clear-Cut; |
| YOL069W | NUF2 | 64a | Cell Growth, Cell Division And DNA Synthesis; Cellular Organization; | YER099C | PRS2 | 64b | Metabolism; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YDR218C | SPR28 | 65a | Cell Growth, Cell Division And DNA Synthesis; Cellular Organization; | YJR076C | CDC11 | 65b | Metabolism; Cell Growth, Cell Division And DNA Synthesis; Cellular Organization; |
| YDL017W | CDC7 | 66a | Cell Growth, Cell Division And DNA Synthesis; Cellular Organization; | YJL088W | ARG3 | 66b | Metabolism; Cellular Organization; |
| YDL017W | CDC7 | 67a | Cell Growth, Cell Division And DNA Synthesis; Cellular Organization; | YDL160C | DHH1 | 67b | Transcription; Cellular Organization; |
| YGR014W | MSB2 | 68a | Cell Growth, Cell Division And DNA Synthesis; Cellular Organization; | YPL211W | NIP7 | 68b | Transcription; Cellular Organization; |
| YLR319C | BUD6 | 69a | Cell Growth, Cell Division And DNA Synthesis; Cellular Organization; | YGL015C | | 69b | Unclassified Proteins; |
| YDL017W | CDC7 | 70a | Cell Growth, Cell Division And DNA Synthesis; Cellular Organization; | YCR022C | | 70b | Unclassified Proteins; |
| YDL017W | CDC7 | 71a | Cell Growth, Cell Division And DNA Synthesis; Cellular Organization; | YCR050C | | 71b | Unclassified Proteins; |
| YDL017W | CDC7 | 72a | Cell Growth, Cell Division And DNA Synthesis; Cellular Organization; | YEL023C | | 72b | Unclassified Proteins; |
| YDL017W | CDC7 | 73a | Cell Growth, Cell Division And DNA Synthesis; Cellular Organization; | YFR057W | | 73b | Unclassified Proteins; |
| YDL017W | CDC7 | 74a | Cell Growth, Cell Division And DNA Synthesis; Cellular Organization; | YNR048W | | 74b | Unclassified Proteins; |
| YDL017W | CDC7 | 75a | Cell Growth, Cell Division And DNA Synthesis; Cellular Organization; | YOR006C | | 75b | Unclassified Proteins; |
| YDL154W | MSH5 | 76a | Cell Growth, Cell Division And DNA Synthesis; Cellular Organization; | YGL170C | | 76b | Unclassified Proteins; |
| YML031W | NDC1 | 77a | Cell Growth, Cell Division And DNA Synthesis; Cellular Organization; | YMR153W | | 77b | Unclassified Proteins; |
| YNL189W | SRP1 | 78a | Cell Growth, Cell Division And DNA Synthesis; Intracellular Transport; Cellular Organization; | YKL130C | SHE2 | 78b | Cell Growth, Cell Division And DNA Synthesis; Cellular Organization; |
| YDR335W | MSN5 | 79a | Cell Growth, Cell Division And DNA Synthesis; Intracellular Transport; | YDR146C | SWI5 | 79b | Cell Growth, Cell Division And DNA Synthesis; Transcription; Cellular Organization; |
| YNL189W | SRP1 | 80a | Cell Growth, Cell Division And DNA Synthesis; Intracellular Transport; Cellular Organization; | YML028W | TSA1 | 80b | Cell Rescue, Defense, Cell Death And Aging; Cellular Organization; |
| YNL189W | SRP1 | 81a | Cell Growth, Cell Division And DNA Synthesis; Intracellular Transport; Cellular Organization; | YMR226C | | 81b | Classification Not Yet Clear-Cut; |
| YNL154C | YCK2 | 82a | Cell Growth, Cell Division And DNA Synthesis; Intracellular Transport; Cell Rescue, Defense, Cell Death And Aging; Cellular Organization; | YOR355W | GDS1 | 82b | Classification Not Yet Clear-Cut; |
| YNL189W | SRP1 | 83a | Cell Growth, Cell Division And DNA Synthesis; Intracellular Transport; Cellular Organization; | YBR252W | DUT1 | 83b | Metabolism; |
| YNL189W | SRP1 | 84a | Cell Growth, Cell Division And DNA Synthesis; Intracellular Transport; Cellular Organization; | YPR062W | FCY1 | 84b | Metabolism; |
| YNL189W | SRP1 | 85a | Cell Growth, Cell Division And DNA Synthesis; Intracellular Transport; Cellular Organization; | YJR159W | SOR1 | 85b | Metabolism; |
| YNL189W | SRP1 | 86a | Cell Growth, Cell Division And DNA Synthesis; Intracellular Transport; Cellular Organization; | YPL214C | THI6 | 86b | Metabolism; |
| YNL189W | SRP1 | 87a | Cell Growth, Cell Division And DNA Synthesis; Intracellular Transport; Cellular Organization; | YFL061W | | 87b | Metabolism; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YNL189W | SRP1 | 88a | Cell Growth, Cell Division And DNA Synthesis; Intracellular Transport; Cellular Organization; | YOL058W | ARG1 | 88b | Metabolism; Cellular Organization; |
| YNL189W | SRP1 | 89a | Cell Growth, Cell Division And DNA Synthesis; Intracellular Transport; Cellular Organization; | YPL111W | CAR1 | 89b | Metabolism; Cellular Organization; |
| YNL189W | SRP1 | 90a | Cell Growth, Cell Division And DNA Synthesis; Intracellular Transport; Cellular Organization; | YLR303W | MET17 | 90b | Metabolism; Cellular Organization; |
| YNL189W | SRP1 | 91a | Cell Growth, Cell Division And DNA Synthesis; Intracellular Transport; Cellular Organization; | YDL236W | PHO13 | 91b | Metabolism; Cellular Organization; |
| YNL189W | SRP1 | 92a | Cell Growth, Cell Division And DNA Synthesis; Intracellular Transport; Cellular Organization; | YER065C | ICL1 | 92b | Metabolism; Energy; Cellular Organization; |
| YNL154C | YCK2 | 93a | Cell Growth, Cell Division And DNA Synthesis; Intracellular Transport; Cell Rescue, Defense, Cell Death And Aging; Cellular Organization; | YMR267W | PPA2 | 93b | Metabolism; Energy; Cellular Organization; |
| YNL189W | SRP1 | 94a | Cell Growth, Cell Division And DNA Synthesis; Intracellular Transport; Cellular Organization; | YGL221C | NIF3 | 94b | Transcription; |
| YNL189W | SRP1 | 95a | Cell Growth, Cell Division And DNA Synthesis; Intracellular Transport; Cellular Organization; | YHL009C | YAP3 | 95b | Transcription; Cellular Organization; |
| YNL154C | YCK2 | 96a | Cell Growth, Cell Division And DNA Synthesis; Intracellular Transport; Cell Rescue, Defense, Cell Death And Aging; Cellular Organization; | YCL054W | | 96b | Transcription; Cellular Organization; |
| YNL154C | YCK2 | 97a | Cell Growth, Cell Division And DNA Synthesis; Intracellular Transport; Cell Rescue, Defense, Cell Death And Aging; Cellular Organization; | YCR011C | ADP1 | 97b | Transport Facilitation; Cellular Organization; |
| YCR009C | RVS161 | 98a | Cell Growth, Cell Division And DNA Synthesis; Intracellular Transport; Cellular Organization; | YBR108W | | 98b | Unclassified Proteins; |
| YNL189W | SRP1 | 99a | Cell Growth, Cell Division And DNA Synthesis; Intracellular Transport; Cellular Organization; | YJR133W | YJR133W | 99b | Unclassified Proteins; |
| YNL189W | SRP1 | 100a | Cell Growth, Cell Division And DNA Synthesis; Intracellular Transport; Cellular Organization; | YGR024C | | 100b | Unclassified Proteins; |
| YNL154C | YCK2 | 101a | Cell Growth, Cell Division And DNA Synthesis; Intracellular Transport; Cell Rescue, Defense, Cell Death And Aging; Cellular Organization; | YER079W | | 101b | Unclassified Proteins; |
| YNL154C | YCK2 | 102a | Cell Growth, Cell Division And DNA Synthesis; Intracellular Transport; Cell Rescue, Defense, Cell Death And Aging; Cellular Organization; | YKL204W | | 102b | Unclassified Proteins; |
| YNL154C | YCK2 | 103a | Cell Growth, Cell Division And DNA Synthesis; Intracellular Transport; Cell Rescue, Defense, Cell Death And Aging; Cellular Organization; | YMR180C | | 103b | Unclassified Proteins; |
| YGL116W | CDC20 | 104a | Cell Growth, Cell Division And DNA Synthesis; Protein Destination; Cellular Organization; | YJL030W | MAD2 | 104b | Cell Growth, Cell Division And DNA Synthesis; |
| YJL001W | PRE3 | 105a | Cell Growth, Cell Division And DNA Synthesis; Protein Destination; Cell Rescue, Defense, Cell Death And Aging; Cellular Organization; | YLR386W | | 105b | Unclassified Proteins; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YFR052W | RPN12 | 106a | Cell Growth, Cell Division And DNA Synthesis; Protein Destination; Cell Rescue, Defense, Cell Death And Aging; Cellular Organization; | YDR273W | | 106b | Unclassified Proteins; |
| YFR052W | RPN12 | 107a | Cell Growth, Cell Division And DNA Synthesis; Protein Destination; Cell Rescue, Defense, Cell Death And Aging; Cellular Organization; | YJR133W | | 107b | Unclassified Proteins; |
| YBL105C | PKC1 | 108a | Cell Growth, Cell Division And DNA Synthesis; Signal Transduction; Cell Rescue, Defense, Cell Death And Aging; Cellular Organization; | YML109W | ZDS2 | 108b | Cell Growth, Cell Division And DNA Synthesis; |
| YPR054W | SMK1 | 109a | Cell Growth, Cell Division And DNA Synthesis; Signal Transduction; | YFL029C | CAK1 | 109b | Cell Growth, Cell Division And DNA Synthesis; |
| YLR229C | CDC42 | 110a | Cell Growth, Cell Division And DNA Synthesis; Signal Transduction; Cellular Organization; | YDL135C | RDI1 | 110b | Cell Growth, Cell Division And DNA Synthesis; Signal Transduction; Cellular Organization; |
| YLR362W | STE11 | 111a | Cell Growth, Cell Division And DNA Synthesis; Signal Transduction; | YCL032W | STE50 | 111b | Cell Growth, Cell Division And DNA Synthesis; Signal Transduction; |
| YJR086W | STE18 | 112a | Cell Growth, Cell Division And DNA Synthesis; Signal Transduction; Cellular Organization; | YOR212W | STE4 | 112b | Cell Growth, Cell Division And DNA Synthesis; Signal Transduction; Cellular Organization; |
| YLR305C | STT4 | 113a | Cell Growth, Cell Division And DNA Synthesis; Signal Transduction; | YOR355W | GDS1 | 113b | Classification Not Yet Clear-Cut; |
| YLR305C | STT4 | 114a | Cell Growth, Cell Division And DNA Synthesis; Signal Transduction; | YOR047C | STD1 | 114b | Metabolism; Transcription; |
| YMR052W | FAR3 | 115a | Cell Growth, Cell Division And DNA Synthesis; Signal Transduction; | YFR008W | | 115b | Unclassified Proteins; |
| YAR003W | | 116a | Cell Growth, Cell Division And DNA Synthesis; Transcription; | YBR175W | | 116b | Unclassified Proteins; |
| YAR003W | | 117a | Cell Growth, Cell Division And DNA Synthesis; Transcription; | YDR140W | | 117b | Unclassified Proteins; |
| YGL192W | IME4 | 118a | Cell Growth, Cell Division And DNA Synthesis; Transcription; Cellular Organization; | YBR057C | MUM2 | 118b | Cell Growth, Cell Division And DNA Synthesis; |
| YCL055W | KAR4 | 119a | Cell Growth, Cell Division And DNA Synthesis; Transcription; Cellular Organization; | YBR057C | MUM2 | 119b | Cell Growth, Cell Division And DNA Synthesis; |
| YNL210W | MER1 | 120a | Cell Growth, Cell Division And DNA Synthesis; Transcription; Cellular Organization; | YKL142W | MRP8 | 120b | Protein Synthesis; Cellular Organization; |
| YOR061W | CKA2 | 121a | Cell Growth, Cell Division And DNA Synthesis; Transcription; Cellular Organization; | YOR039W | CKB2 | 121b | Transcription; Cellular Organization; |
| YNR010W | CSE2 | 122a | Cell Growth, Cell Division And DNA Synthesis; Transcription; Cellular Organization; | YOR174W | MED4 | 122b | Transcription; Cellular Organization; |
| YHL027W | RIM101 | 123a | Cell Growth, Cell Division And DNA Synthesis; Transcription; Cellular Organization; | YJL056C | ZAP1 | 123b | Transcription; Cellular Organization; |
| YOL006C | TOP1 | 124a | Cell Growth, Cell Division And DNA Synthesis; Transcription; Cellular Organization; | YMR233W | | 124b | Unclassified Proteins; |
| YLR433C | CNA1 | 125a | Cell Growth, Cell Division And DNA Synthesis; Transcription; Ionic Homeostasis; Cellular Organization; | YNL047C | | 125b | Unclassified Proteins; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YGL058W | RAD6 | 126a | Cell Growth, Cell Division And DNA Synthesis; Transcription; Protein Destination; Cell Rescue, Defense, Cell Death And Aging; Cellular Organization; | YCR066W | RAD18 | 126b | Cell Growth, Cell Division And DNA Synthesis; Protein Destination; Cell Rescue, Defense, Cell Death And Aging; Cellular Organization; |
| YPR018W | RLF2 | 127a | Cell Growth, Cell Division And DNA Synthesis; Transcription; Protein Destination; Cellular Organization; | YBR195C | MSI1 | 127b | Cell Growth, Cell Division And DNA Synthesis; Transcription; Protein Destination; Cellular Biogenesis; Signal Transduction; |
| YHR084W | STE12 | 128a | Cell Growth, Cell Division And DNA Synthesis; Transcription; Signal Transduction; Cellular Organization; | YDR480W | DIG2 | 128b | Cell Growth, Cell Division And DNA Synthesis; Cellular Organization; |
| YBR244W | | 129a | Cell Rescue, Defense, Cell Death And Aging; | YLR117C | SYF3 | 129b | Cell Growth, Cell Division And DNA Synthesis; |
| YLL057C | | 130a | Cell Rescue, Defense, Cell Death And Aging; | YLL057C | | 130b | Cell Rescue, Defense, Cell Death And Aging; |
| YIL011W | | 131a | Cell Rescue, Defense, Cell Death And Aging; | YMR201C | RAD14 | 131b | Cell Rescue, Defense, Cell Death And Aging; Cellular Organization; |
| YHL046C | | 132a | Cell Rescue, Defense, Cell Death And Aging; | YOR355W | GDS1 | 132b | Classification Not Yet Clear-Cut; |
| YGR213C | RTA1 | 133a | Cell Rescue, Defense, Cell Death And Aging; | YHR134W | | 133b | Unclassified Proteins; |
| YDR061W | | 134a | Cell Rescue, Defense, Cell Death And Aging; | YCR086W | | 134b | Unclassified Proteins; |
| YLR046C | | 135a | Cell Rescue, Defense, Cell Death And Aging; | YHL006C | | 135b | Unclassified Proteins; |
| YJL092W | HPR5 | 136a | Cell Rescue, Defense, Cell Death And Aging; Cellular Organization; | YOR355W | GDS1 | 136b | Classification Not Yet Clear-Cut; |
| YDR077W | SED1 | 137a | Cell Rescue, Defense, Cell Death And Aging; Cellular Organization; | YDR044W | HEM13 | 137b | Metabolism; Cellular Organization; |
| YJL092W | HPR5 | 138a | Cell Rescue, Defense, Cell Death And Aging; Cellular Organization; | YDR510W | SMT3 | 138b | Protein Destination; |
| YJL092W | HPR5 | 139a | Cell Rescue, Defense, Cell Death And Aging; Cellular Organization; | YBR184W | MEL1 | 139b | Unclassified Proteins; |
| YJL092W | HPR5 | 140a | Cell Rescue, Defense, Cell Death And Aging; Cellular Organization; | YDR078C | PUN1 | 140b | Unclassified Proteins; |
| YLR390W | ECM19 | 141a | Cellular Biogenesis; | YDR145W | TAF61 | 141b | Transcription; |
| YHR171W | | 142a | Cellular Biogenesis; Cellular Organization; | YBR217W | | 142b | Protein Destination; Cellular Biogenesis; Cellular Organization; |
| YHR171W | | 143a | Cellular Biogenesis; Cellular Organization; | YNR007C | AUT1 | 143b | Protein Destination; Intracellular Transport; |
| YHR171W | | 144a | Cellular Biogenesis; Cellular Organization; | YBL078C | AUT1 | 144b | Protein Destination; Intracellular Transport; Cellular Organization; |
| YKR037C | | 145a | Cellular Organization; | YJR091C | JSN1 | 145b | Cell Growth, Cell Division And DNA Synthesis; |
| YCL059C | KRR1 | 146a | Cellular Organization; | YGL201C | MCM6 | 146b | Cell Growth, Cell Division And DNA Synthesis; Cellular Organization; |
| YDR106W | ARP10 | 147a | Cellular Organization; | YHR129C | ARP1 | 147b | Cell Growth, Cell Division And DNA Synthesis; Intracellular Transport; Cellular Organization; |
| YMR092C | AIP1 | 148a | Cellular Organization; | YLR102C | APC9 | 148b | Cell Growth, Cell Division And DNA Synthesis; Protein Destination; |
| YDR201W | | 149a | Cellular Organization; | YIL144W | TID3 | 149b | Cellular Organization; |
| YER018C | | 150a | Cellular Organization; | YMR117C | | 150b | Cellular Organization; |
| YKR037C | | 151a | Cellular Organization; | YDR201W | | 151b | Cellular Organization; |
| YLR429W | CRN1 | 152a | Cellular Organization; | YDR328C | SKP1 | 152b | Metabolism; Cell Growth, Cell Division And DNA Synthesis; Protein Destination; Cellular Organization; |
| YER018C | | 153a | Cellular Organization; | YHR193C | EGD2 | 153b | Metabolism; Transcription; Cellular Organization; |
| YDR122W | KIN1 | 154a | Cellular Organization; Classification Not Yet Clear-Cut; | YOL082W | | 154b | Unclassified Proteins; |
| YNL218W | | 155a | Classification Not Yet Clear-Cut; | YJL030W | MAD2 | 155b | Cell Growth, Cell Division And DNA Synthesis; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YNL023C | FAP1 | 156a | Classification Not Yet Clear-Cut; | YMR224C | MRE11 | 156b | Cell Growth, Cell Division And DNA Synthesis; Cellular Biogenesis; Cell Rescue, Defense, Cell Death And Aging; Cellular Organization; |
| YNL023C | FAP1 | 157a | Classification Not Yet Clear-Cut; | YKL130C | SHE2 | 157b | Cell Growth, Cell Division And DNA Synthesis; Cellular Organization; |
| YCL024W | | 158a | Classification Not Yet Clear-Cut; | YKR048C | NAP1 | 158b | Cell Growth, Cell Division And DNA Synthesis; Protein Destination; Cellular Biogenesis; Cellular Organization; |
| YFR024C-A | | 159a | Classification Not Yet Clear-Cut; | YBL007C | SLA1 | 159b | Cell Growth, Cell Division And DNA Synthesis; Protein Destination; Cellular Organization; |
| YNL218W | | 160a | Classification Not Yet Clear-Cut; | YNL218W | | 160b | Classification Not Yet Clear-Cut; |
| YLL046C | RNP1 | 161a | Classification Not Yet Clear-Cut; | YFR047C | | 161b | Metabolism; |
| YBR274W | | 162a | Classification Not Yet Clear-Cut; | YLR258W | GSY2 | 162b | Metabolism; Energy; Cellular Organization; |
| YDL002C | NHP10 | 163a | Classification Not Yet Clear-Cut; | YER092W | | 163b | Unclassified Proteins; |
| YER059W | PCL6 | 164a | Classification Not Yet Clear-Cut; | YJL084C | | 164b | Unclassified Proteins; |
| YER059W | PCL6 | 165a | Classification Not Yet Clear-Cut; | YLR190W | | 165b | Unclassified Proteins; |
| YBR274W | | 166a | Classification Not Yet Clear-Cut; | YMR255W | | 166b | Unclassified Proteins; |
| YDR084C | | 167a | Classification Not Yet Clear-Cut; | YGL161C | | 167b | Unclassified Proteins; |
| YDR084C | | 168a | Classification Not Yet Clear-Cut; | YGL198W | | 168b | Unclassified Proteins; |
| YFR024C-A | | 169a | Classification Not Yet Clear-Cut; | YGR268C | | 169b | Unclassified Proteins; |
| YMR077C | | 170a | Classification Not Yet Clear-Cut; | YKL052C | | 170b | Unclassified Proteins; |
| YHR039C | | 171a | Energy; | YDR480W | DIG2 | 171b | Cell Growth, Cell Division And DNA Synthesis; Cellular Organization; |
| YPR048W | | 172a | Energy; | YOR355W | GDS1 | 172b | Classification Not Yet Clear-Cut; |
| YPR048W | | 173a | Energy; | YDL215C | GDH2 | 173b | Metabolism; Cellular Organization; |
| YPR048W | | 174a | Energy; | YNL199C | GCR2 | 174b | Metabolism; Transcription; Cellular Organization; |
| YNL118C | PSU1 | 175a | Energy; | YOL149W | DCP1 | 175b | Transcription; |
| YNL118C | PSU1 | 176a | Energy; | YEL015W | | 176b | Unclassified Proteins; |
| YPR048W | | 177a | Energy; | YPR070W | | 177b | Unclassified Proteins; |
| YPL174C | NIP100 | 178a | Intracellular Transport; | YHR129C | ARP1 | 178b | Cell Growth, Cell Division And DNA Synthesis; Intracellular Transport; Cellular Organization; |
| YPL174C | NIP100 | 179a | Intracellular Transport; | YIL144W | TID3 | 179b | Cellular Organization; |
| YGR057C | LST7 | 180a | Intracellular Transport; | YKL015W | PUT3 | 180b | Metabolism; Transcription; Cellular Organization; |
| YPL174C | NIP100 | 181a | Intracellular Transport; | YJL184W | | 181b | Unclassified Proteins; |
| YER105C | NUP157 | 182a | Intracellular Transport; Cellular Organization; | YJL030W | MAD2 | 182b | Cell Growth, Cell Division And DNA Synthesis; |
| YFR002W | NIC96 | 183a | Intracellular Transport; Cellular Organization; | YGR120C | | 183b | Intracellular Transport; Cellular Organization; |
| YHL019C | APM2 | 184a | Intracellular Transport; Cellular Organization; | YKL135C | APL2 | 184b | Protein Destination; Intracellular Transport; Cellular Organization; |
| YGR119C | NUP57 | 185a | Intracellular Transport; Cellular Organization; | YMR236W | TAF17 | 185b | Transcription; Cellular Organization; |
| YGR119C | NUP57 | 186a | Intracellular Transport; Cellular Organization; | YJL041W | NSP1 | 186b | Transcription; Intracellular Transport; Cellular Organization; |
| YGR119C | NUP57 | 187a | Intracellular Transport; Cellular Organization; | YGL172W | NUP49 | 187b | Transcription; Intracellular Transport; Cellular Organization; |
| YFR002W | NIC96 | 188a | Intracellular Transport; Cellular Organization; | YMR153W | | 188b | Unclassified Proteins; |
| YER105C | NUP157 | 189a | Intracellular Transport; Cellular Organization; | YEL015W | | 189b | Unclassified Proteins; |
| YER105C | NUP157 | 190a | Intracellular Transport; Cellular Organization; | YMR153W | | 190b | Unclassified Proteins; |
| YMR129W | POM152 | 191a | Intracellular Transport; Cellular Organization; | YJL057C | IKS1 | 191b | Unclassified Proteins; |
| YMR129W | POM152 | 192a | Intracellular Transport; Cellular Organization; | YMR153W | | 192b | Unclassified Proteins; |
| YNL287W | SEC21 | 193a | Intracellular Transport; Cellular Organization; | YBR281C | | 193b | Unclassified Proteins; |
| YOR115C | | 194a | Intracellular Transport; Cellular Organization; | YOL082W | | 194b | Unclassified Proteins; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YDR503C | LPP1 | 195a | Metabolism; | YKL130C | SHE2 | 195b | Cell Growth, Cell Division And DNA Synthesis; Cellular Organization; |
| YOR128C | ADE2 | 196a | Metabolism; | YCR066W | RAD18 | 196b | Cell Growth, Cell Division And DNA Synthesis; Protein Destination; Cell Rescue, Defense, Cell Death And Aging; Cellular Organization; |
| YNL201C | | 197a | Metabolism; | YOR355W | GDS1 | 197b | Classification Not Yet Clear-Cut; |
| YOR128C | ADE2 | 198a | Metabolism; | YCR067C | SED4 | 198b | Intracellular Transport; Cellular Organization; |
| YOR128C | ADE2 | 199a | Metabolism; | YOR128C | ADE2 | 199b | Metabolism; |
| YIR032C | DAL3 | 200a | Metabolism; | YIR032C | DAL3 | 200b | Metabolism; |
| YGR267C | FOL2 | 201a | Metabolism; | YGR267C | FOL2 | 201b | Metabolism; |
| YOL061W | PRS5 | 202a | Metabolism; | YER099C | PRS2 | 202b | Metabolism; |
| YPL214C | THI6 | 203a | Metabolism; | YPL214C | THI6 | 203b | Metabolism; |
| YNR012W | URK1 | 204a | Metabolism; | YDR020C | | 204b | Metabolism; |
| YDL246C | | 205a | Metabolism; | YJR159W | SOR1 | 205b | Metabolism; |
| YDL246C | | 206a | Metabolism; | YDL246C | | 206b | Metabolism; |
| YFR047C | | 207a | Metabolism; | YFR047C | | 207b | Metabolism; |
| YHL018W | | 208a | Metabolism; | YHL018W | | 208b | Metabolism; |
| YHR111W | | 209a | Metabolism; | YHR111W | | 209b | Metabolism; |
| YIL074C | | 210a | Metabolism; | YER081W | | 210b | Metabolism; |
| YIL074C | | 211a | Metabolism; | YIL074C | | 211b | Metabolism; |
| YLR245C | | 212a | Metabolism; | YLR245C | | 212b | Metabolism; |
| YLR432W | | 213a | Metabolism; | YDL215C | GDH2 | 213b | Metabolism; Cellular Organization; |
| YNL201C | | 214a | Metabolism; | YFL056C | AAD6 | 214b | Metabolism; Energy; |
| YOR226C | | 215a | Metabolism; | YPL088W | | 215b | Metabolism; Energy; |
| YNL201C | | 216a | Metabolism; | YOR047C | STD1 | 216b | Metabolism; Transcription; |
| YDL013W | HEX3 | 217a | Metabolism; | YDR510W | SMT3 | 217b | Protein Destination; |
| YLR432W | | 218a | Metabolism; | YKR026C | GCN3 | 218b | Protein Synthesis; Cellular Organization; |
| YHR204W | | 219a | Metabolism; | YGL030W | RPL30 | 219b | Protein Synthesis; Cellular Organization; |
| YBR006W | | 220a | Metabolism; | YDR382W | RPP2B | 220b | Protein Synthesis; Cellular Organization; |
| YDL013W | HEX3 | 221a | Metabolism; | YER116C | | 221b | Transcription; |
| YNL201C | | 222a | Metabolism; | YPR115W | | 222b | Transcription; |
| YPL059W | | 223a | Metabolism; | YIL105C | | 223b | Transcription; |
| YLR432W | | 224a | Metabolism; | YDR167W | TAF25 | 224b | Transcription; Cellular Organization; |
| YOR128C | ADE2 | 225a | Metabolism; | YBR134W | | 225b | Unclassified Proteins; |
| YGR155W | CYS4 | 226a | Metabolism; | YCR086W | | 226b | Unclassified Proteins; |
| YOR269W | PAC1 | 227a | Metabolism; | YLR254C | | 227b | Unclassified Proteins; |
| YBR006W | | 228a | Metabolism; | YKL023W | | 228b | Unclassified Proteins; |
| YDL203C | | 229a | Metabolism; | YGR058W | | 229b | Unclassified Proteins; |
| YDL203C | | 230a | Metabolism; | YOR372C | | 230b | Unclassified Proteins; |
| YDR400W | | 231a | Metabolism; | YCR059C | | 231b | Unclassified Proteins; |
| YHR204W | | 232a | Metabolism; | YER126C | | 232b | Unclassified Proteins; |
| YLR432W | | 233a | Metabolism; | YDR469W | | 233b | Unclassified Proteins; |
| YPL059W | | 234a | Metabolism; | YNL047C | | 234b | Unclassified Proteins; |
| YDL006W | PTC1 | 235a | Metabolism Cell Growth, Cell Division And DNA Synthesis; Cellular Biogenesis; Signal Transduction; Cell Rescue, Defense, Cell Death And Aging; | YDR162C | NBP2 | 235b | Protein Destination; |
| YDR328C | SKP1 | 236a | Metabolism; Cell Growth, Cell Division And DNA Synthesis; Protein Destination; Cellular Organization; | YFL009W | CDC4 | 236b | Cell Growth, Cell Division And DNA Synthesis; Cellular Organization; |
| YGL155W | CDC43 | 237a | Metabolism; Cell Growth, Cell Division And DNA Synthesis; Protein Destination; Cellular Organization; | YKL019W | RAM2 | 237b | Metabolism; Protein Destination; Cellular Organization; |
| YDR328C | SKP1 | 238a | Metabolism; Cell Growth, Cell Division And DNA Synthesis; Protein Destination; Cellular Organization; | YLR352W | | 238b | Unclassified Proteins; |
| YPL161C | BEM4 | 239b | Metabolism; Cell Growth, Cell Division And DNA Synthesis; Signal Transduction; | YGL126W | SCS3 | 239b | Metabolism; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YPL161C | BEM4 | 240a | Metabolism; Cell Growth, Cell Division And DNA Synthesis; Signal Transduction; | YIL163C | | 240b | Unclassified Proteins; |
| YPL161C | BEM4 | 241a | Metabolism; Cell Growth, Cell Division And DNA Synthesis; Signal Transduction; | YLR049C | | 241b | Unclassified Proteins; |
| YNL236W | SIN4 | 242a | Metabolism; Cell Growth, Cell Division And DNA Synthesis; Transcription; Cellular Organization; | YJL030W | MAD2 | 242b | Cell Growth, Cell Division And DNA Synthesis; |
| YNL236W | SIN4 | 243a | Metabolism; Cell Growth, Cell Division And DNA Synthesis; Transcription; Cellular Organization; | YGL238W | CSE1 | 243b | Cell Growth, Cell Division And DNA Synthesis; Cellular Organization; |
| YNL236W | SIN4 | 244a | Metabolism; Cell Growth, Cell Division And DNA Synthesis; Transcription; Cellular Organization; | YJL013C | MAD3 | 244b | Cell Growth, Cell Division And DNA Synthesis; Cellular Organization; |
| YNL236W | SIN4 | 245a | Metabolism; Cell Growth, Cell Division And DNA Synthesis; Transcription; Cellular Organization; | YOR355W | GDS1 | 245b | Classification Not Yet Clear-Cut; |
| YDR207C | UME6 | 246a | Metabolism; Cell Growth, Cell Division And DNA Synthesis; Transcription; Cellular Organization; | YOR355W | GDS1 | 246b | Classification Not Yet Clear-Cut; |
| YNL236W | SIN4 | 247a | Metabolism; Cell Growth, Cell Division And DNA Synthesis; Transcription; Cellular Organization; | YFR033C | QCR6 | 247b | Energy; Cellular Organization; |
| YNL236W | SIN4 | 248a | Metabolism; Cell Growth, Cell Division And DNA Synthesis; Transcription; Cellular Organization; | YJR034W | PET191 | 248b | Energy; Protein Destination; Cellular Organization; |
| YNL236W | SIN4 | 249a | Metabolism; Cell Growth, Cell Division And DNA Synthesis; Transcription; Cellular Organization; | YDR054C | CDC34 | 249b | Metabolism; Cell Growth, Cell Division And DNA Synthesis; Protein Destination; Cellular Organization; |
| YNL236W | SIN4 | 250a | Metabolism; Cell Growth, Cell Division And DNA Synthesis; Transcription; Cellular Organization; | YKL012W | PRP40 | 250b | Transcription; Cellular Organization; |
| YNL236W | SIN4 | 251a | Metabolism; Cell Growth, Cell Division And DNA Synthesis; Transcription; Cellular Organization; | YGR046W | | 251b | Unclassified Proteins; |
| YNL236W | SIN4 | 252a | Metabolism; Cell Growth, Cell Division And DNA Synthesis; Transcription; Cellular Organization; | YGR117C | | 252b | Unclassified Proteins; |
| YDR207C | UME6 | 253a | Metabolism; Cell Growth, Cell Division And DNA Synthesis; Transcription; Cellular Organization; | YOL082W | | 253b | Unclassified Proteins; |
| YGR144W | THI43 | 254a | Metabolism; Cell Rescue, Defense, Cell Death And Aging; | YGR144W | THI4 | 254b | Metabolism; Cell Rescue, Defense, Cell Death And Aging; |
| YER062C | HOR2 | 255a | Metabolism; Cell Rescue, Defense, Cell Death And Aging; | YPL201C | | 255b | Unclassified Proteins; |
| YDR477W | SNF1 | 256a | Metabolism; Cell Rescue, Defense, Cell Death And Aging; Cellular Organization; | YER027C | GAL83 | 256b | Metabolism; Transcription; |
| YBR176W | ECM31 | 257a | Metabolism; Cellular Biogenesis; | YBR176W | ECM31 | 257b | Metabolism; Cellular Biogenesis; |
| YDR376W | ARH1 | 258a | Metabolism; Cellular Organization; | YIR024C | GIF1 | 258b | Cell Growth, Cell Division And DNA Synthesis; |
| YDR408C | ADE8 | | Metabolism; Cellular Organization; | YGL127C | SOH1 | | Cell Growth, Cell Division And DNA Synthesis; Transcription; |
| YDR376W | ARH1 | 259a | Metabolism; Cellular Organization; | YCR093W | CDC39 | 259b | Cell Growth, Cell Division And DNA Synthesis; Transcription; Cellular Organization; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YDR408C | ADE8 | 260a | Metabolism; Cellular Organization; | YCR063W | | 260b | Classification Not Yet Clear-Cut; |
| YLR438W | CAR2 | 261a | Metabolism; Cellular Organization; | YHL025W | SNF6 | 261b | Metabolism; Cell Growth, Cell Division And DNA Synthesis; Transcription; Cellular Organization; |
| YOR180C | EHD2 | 262a | Metabolism; Cellular Organization; | YLR284C | EHD1 | 262b | Metabolism; Cellular Organization; |
| YOR202W | HIS3 | 263a | Metabolism; Cellular Organization; | YOR202W | HIS3 | 263b | Metabolism; Cellular Organization; |
| YER023W | PRO3 | 264a | Metabolism; Cellular Organization; | YER023W | PRO3 | 264b | Metabolism; Cellular Organization; |
| YKL067W | YNK1 | 265a | Metabolism; Cellular Organization; | YKL067W | YNK1 | 265b | Metabolism; Cellular Organization; |
| YGL154C | LYS5 | 266a | Metabolism; Cellular Organization; | YGL154W | FZF1 | 266b | Metabolism; Transcription; Cell Rescue, Defense, Cell Death And Aging; Cellular Organization; |
| YGR229C | SMI1 | 267a | Metabolism; Cellular Organization; | YKR099W | BAS1 | 267b | Metabolism; Transcription; Cellular Organization; |
| YBL042C | FUI1 | 268a | Metabolism; Cellular Organization; | YER021W | RPN3 | 268b | Protein Destination; |
| YHR128W | FUR1 | 269a | Metabolism; Cellular Organization; | YPR185W | APG13 | 269b | Protein Destination; Intracellular Transport; |
| YOR375C | GDH1 | 270a | Metabolism; Cellular Organization; | YJL124C | SPB8 | 270b | Transcription; |
| YDR408C | ADE8 | 271a | Metabolism; Cellular Organization; | YOR174W | MED4 | 271b | Transcription; Cellular Organization; |
| YOR303W | CPA1 | 272a | Metabolism; Cellular Organization; | YOR039W | CKB2 | 272b | Transcription; Cellular Organization; |
| YGR061C | ADE6 | 273a | Metabolism; Cellular Organization; | YLR386W | | 273b | Unclassified Proteins; |
| YLR438W | CAR2 | 274a | Metabolism; Cellular Organization; | YGR010W | | 274b | Unclassified Proteins; |
| YLR438W | CAR2 | 275a | Metabolism; Cellular Organization; | YLR328W | | 275b | Unclassified Proteins; |
| YOL059W | GPD2 | 276a | Metabolism; Cellular Organization; | YFL017C | | 276b | Unclassified Proteins; |
| YNL104C | LEU4 | 277a | Metabolism; Cellular Organization; | YKL183W | | 277b | Unclassified Proteins; |
| YLR345W | | 278a | Metabolism; Energy; | YLR321C | SFH1 | 278b | Cell Growth, Cell Division And DNA Synthesis; Transcription; Cellular Biogenesis; Cellular Organization; |
| YJL137C | GLG2 | 279a | Metabolism; Energy; | YJL137C | GLG2 | 279b | Metabolism; Energy; |
| YGL134W | PCL10 | 280a | Metabolism; Energy; | YPL031C | PHO85 | 280b | Metabolism; Energy; Cell Growth, Cell Division And DNA Synthesis; Transcription; Cellular Organization; |
| YLR345W | | 281a | Metabolism; Energy; | YGR158C | MTR3 | 281b | Transcription; Cellular Organization; |
| YKR096W | | 282a | Metabolism; Energy; | YBL051C | | 282b | Unclassified Proteins; |
| YER133W | GLC7 | 283a | Metabolism; Energy; Cell Growth, Cell Division And DNA Synthesis; Protein Synthesis; Cellular Organization; | YNL233W | BNI4 | 283b | Cell Growth, Cell Division And DNA Synthesis; Protein Destination; Cellular Organization; |
| YLR071C | RGR1 | 284a | Metabolism; Energy; Cell Growth, Cell Division And DNA Synthesis; Transcription; Cellular Organization; | YDL065C | PEX19 | 284b | Cellular Organization; |
| YDR074W | TPS2 | 285a | Metabolism; Energy; Cell Rescue, Defense, Cell Death And Aging; Cellular Organization; | YER019C-A | SBH2 | 285b | Protein Destination; Transport Facilitation; Intracellular Transport; |
| YDR074W | TPS2 | 286a | Metabolism; Energy; Cell Rescue, Defense, Cell Death And Aging; Cellular Organization; | YAR066W | | 286b | Unclassified Proteins; |
| YBR221C | PDB1 | 287a | Metabolism; Energy; Cellular Organization; | YLR345W | | 287b | Metabolism; Energy; |
| YDR148C | KGD2 | 288a | Metabolism; Energy; Cellular Organization; | YDR510W | SMT3 | 288b | Protein Destination; |
| YMR267W | PPA2 | 289a | Metabolism; Energy; Cellular Organization; | YKR026C | GCN3 | 289b | Protein Synthesis; Cellular Organization; |
| YDR001C | | 290a | Metabolism; Energy; Cellular Organization; | YLR270W | | 290b | Unclassified Proteins; |
| YCL040W | GLK1 | 291a | Metabolism; Energy; Intracellular Transport; Cellular Organization; | YBR040W | FIG1 | 291b | Cell Growth, Cell Division And DNA Synthesis; Cellular Organization; |
| YCL040W | GLK1 | 292a | Metabolism; Energy; Intracellular Transport; Cellular Organization; | YML099C | ARG81 | 292b | Metabolism; Transcription; Cellular Organization; |
| YMR079W | SEC14 | 293a | Metabolism; Intracellular Transport; Cellular Organization; | YDL001W | | 293b | Unclassified Proteins; |
| YDL090C | RAM1 | 294a | Metabolism; Protein Destination; Signal Transduction; Cellular Organization; | YKL019W | RAM2 | 294b | Metabolism; Protein Destination; Cellular Organization; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YLR150W | STM1 | 295a | Metabolism; Signal Transduction; | YJR072C | | 295b | Unclassified Proteins; |
| YGL254W | FZF1 | 296a | Metabolism; Transcription; Cell Rescue, Defense, Cell Death And Aging; Cellular Organization; | YHR215W | PHO12 | 296b | Metabolism; Cellular Organization; |
| YGL115W | SNF4 | 297a | Metabolism; Transcription; Cell Rescue, Defense, Cell Death And Aging; Cellular Organization; | YER027C | GAL83 | 297b | Metabolism; Transcription; |
| YGL254W | FZF1 | 298a | Metabolism; Transcription; Cell Rescue, Defense, Cell Death And Aging; Cellular Organization; | YOR039W | CKB2 | 298b | Transcription; Cellular Organization; |
| YGL254W | FZF1 | 299a | Metabolism; Transcription; Cell Rescue, Defense, Cell Death And Aging; Cellular Organization; | YGR047C | TFC4 | 299b | Transcription; Cellular Organization; |
| YOL108C | INO4 | 300a | Metabolism; Transcription; Cellular Organization; | YKL017C | HCS1 | 300b | Cell Growth, Cell Division And DNA Synthesis; |
| YOL108C | INO4 | 301a | Metabolism; Transcription; Cellular Organization; | YMR317W | | 301b | Cellular Biogenesis; |
| YNL314W | DAL82 | 302a | Metabolism; Transcription; Cellular Organization; | YNL314W | DAL82 | 302b | Metabolism; Transcription; Cellular Organization; |
| YOL108C | INO4 | 303a | Metabolism; Transcription; Cellular Organization; | YDR123C | INO2 | 303b | Metabolism; Transcription; Cellular Organization; |
| YOL108C | INO4 | 304a | Metabolism; Transcription; Cellular Organization; | YKL135C | APL2 | 304b | Protein Destination; Intracellular Transport; Cellular Organization; |
| YJL110C | GZF3 | 305a | Metabolism; Transcription; Cellular Organization; | YNL021W | HDA1 | 305b | Transcription; Protein Destination; Cellular Organization; |
| YOL108C | INO4 | 306a | Metabolism; Transcription; Cellular Organization; | YNL279W | | 306b | Unclassified Proteins; |
| YOR348C | PUT4 | 307a | Metabolism; Transport Facilitation; Intracellular Transport; Cellular Organization; | YMR228W | MTF1 | 307b | Cell Growth, Cell Division And DNA Synthesis; Transcription; Cellular Organization; |
| YOR348C | PUT4 | 308a | Metabolism; Transport Facilitation; Intracellular Transport; Cellular Organization; | YCR045C | | 308b | Protein Destination; |
| YOR348C | PUT4 | 309a | Metabolism; Transport Facilitation; Intracellular Transport; Cellular Organization; | YJL084C | | 309b | Unclassified Proteins; |
| YOR348C | PUT4 | 310a | Metabolism; Transport Facilitation; Intracellular Transport; Cellular Organization; | YLR294C | | 310b | Unclassified Proteins; |
| YMR091C | NPL6 | 311a | Protein Destination; | YFR037C | RSC8 | 311b | Cell Growth, Cell Division And DNA Synthesis; Transcription; Cellular Organization; |
| YER144C | UBP5 | 312a | Protein Destination; | YBR059C | | 312b | Classification Not Yet Clear-Cut; |
| YLR417W | VPS36 | 313a | Protein Destination; | YPL002C | SNF8 | 313b | Metabolism; |
| YDL097C | RPN6 | 314a | Protein Destination; | YEL009C | GCN4 | 314b | Metabolism; Transcription; Cellular Organization; |
| YDR394W | RPT3 | 315a | Protein Destination; | YGR232W | | 315b | Protein Destination; |
| YPL003W | ULA1 | 316a | Protein Destination; | YPR066W | UBA3 | 316b | Protein Destination; |
| YOR132W | VPS17 | 317a | Protein Destination; | YOR069W | VPS5 | 317b | Protein Destination; Cellular Organization; |
| YDR098C | | 318a | Protein Destination; | YGL071W | RCS1 | 318b | Transcription; Ionic Homeostasis; Cellular Organization; |
| YER174C | | 319a | Protein Destination; | YGL071W | RCS1 | 319b | Transcription; Ionic Homeostasis; Cellular Organization; |
| YML094W | GIM5 | 320a | Protein Destination; | YLR200W | YKE2 | 320b | Unclassified Proteins; |
| YOL111C | | 321a | Protein Destination; | YOR007C | SGT2 | 321b | Unclassified Proteins; |
| YHR057C | CYP2 | 322a | Protein Destination; Cell Rescue, Defense, Cell Death And Aging; Cellular Organization; | YJR091C | JSN1 | 322b | Cell Growth, Cell Division And DNA Synthesis; |
| YPL149W | APG5 | 323a | Protein Destination; Cellular Biogenesis; Cellular Organization; | YBR217W | | 323b | Protein Destination; Cellular Biogenesis; Cellular Organization; |
| YPL149W | APG5 | 324a | Protein Destination; Cellular Biogenesis; Cellular Organization; | YMR159C | SAP18 | 324b | Unclassified Proteins; |
| YBR217W | | 325a | Protein Destination; Cellular Biogenesis; Cellular Organization; | YMR159C | SAP18 | 325b | Unclassified Proteins; |
| YMR314W | PRE5 | 326a | Protein Destination; Cellular Organization; | YKL130C | SHE2 | 326b | Cell Growth, Cell Division And DNA Synthesis; Cellular Organization; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YPR051W | MAK3 | 327a | Protein Destination; Cellular Organization; | YEL053C | MAK10 | 327b | Energy; |
| YNL135C | FPR1 | 328a | Protein Destination; Cellular Organization; | YER052C | HOM3 | 328b | Metabolism; |
| YKL103C | LAP4 | 329a | Protein Destination; Cellular Organization; | YKL103C | LAP4 | 329b | Protein Destination; Cellular Organization; |
| YHR060W | VMA22 | 330a | Protein Destination; Cellular Organization; | YLR447C | VMA6 | 330b | Protein Destination; Transport Facilitation; Intracellular Transport; Ionic Homeostatis; Cellular Organization; |
| YOL088C | MPD2 | 331a | Protein Destination; Cellular Organization; | YHR091C | MSR1 | 331a | Protein Synthesis; Cellular Organization; |
| YKL103C | LAP4 | 332a | Protein Destination; Cellular Organization; | YOL082W | | 332b | Unclassified Proteins; |
| YOL088C | MPD2 | 333a | Protein Destination; Cellular Organization; | YLR312C | | 333b | Unclassified Proteins; |
| YEL060C | PRB1 | 334a | Protein Destination; Cellular Organization; | YML032C-A | | 334b | Unclassified Proteins; |
| YOR362C | PRE10 | 335a | Protein Destination; Cellular Organization; | YFL017C | | 335b | Unclassified Proteins; |
| YDR292C | SRP101 | 336a | Protein Destination; Cellular Organization; | YMR163C | | 336b | Unclassified Proteins; |
| YHR060W | VMA22 | 337a | Protein Destination; Cellular Organization; | YDR469W | | 337b | Unclassified Proteins; |
| YPR185W | APG13 | 338a | Protein Destination; Intracellular Transport; | YGL180W | APG1 | 338b | Cell Growth, Cell Division And DNA Synthesis; Protein Destination; Intracellular Transport; Cellular Organization; |
| YPR185W | APG13 | 339a | Protein Destination; Intracellular Transport; | YGR253C | PUP2 | 339b | Cell Growth, Cell Division And DNA Synthesis; Protein Destination; Cell Rescue, Defense, Cell Death And Aging; Cellular Organization; |
| YPR185W | APG13 | 340a | Protein Destination; Intracellular Transport; | YGR120C | | 340b | Intracellular Transport; Cellular Organization; |
| YBR170C | NPL4 | 341a | Protein Destination; Intracellular Transport; | YGR048W | UFD1 | 341b | Protein Destination; |
| YPR185W | APG13 | 342a | Protein Destination; Intracellular Transport; | YNL086W | | 342b | Unclassified Proteins; |
| YNL093W | YPT53 | 343a | Protein Destination; Intracellular Transport; | YNL032W | SIW14 | 343b | Unclassified Proteins; |
| YPR173C | VPS4 | 344a | Protein Destination; Intracellular Transport; Cellular Biogenesis; Cellular Organization; | YLR025W | SNF7 | 344b | Metabolism; Cell Growth, Cell Division And DNA Synthesis; Protein Destination; Cellular Organization; |
| YPL259C | APM1 | 345a | Protein Destination; Intracellular Transport; Cellular Biogenesis; Cellular Organization; | YKL135C | APL2 | 345b | Protein Destination; Intracellular Transport; Cellular Organization; |
| YJL154C | VPS35 | 346a | Protein Destination; Intracellular Transport; Cellular Biogenesis; Cellular Organization; | YGL166W | CUP2 | 346b | Transcription; Ionic Homeostasis; Cellular Organization; |
| YDR142C | PEX7 | 347a | Protein Destination; Intracellular Transport; Cellular Organization; | YIL160C | POT1 | 347b | Metabolism; Energy; Cellular Organization; |
| YNR006W | VPS27 | 348a | Protein Destination; Intracellular Transport; Cellular Organization; | YHL002W | | 348b | Signal Transduction; |
| YDR142C | PEX7 | 349a | Protein Destination; Intracellular Transport; Cellular Organization; | YGR239C | | 349b | Unclassified Proteins; |
| YDR142C | PEX7 | 350a | Protein Destination; Intracellular Transport; Cellular Organization; | YHR160C | | 350b | Unclassified Proteins; |
| YDL212W | SHR3 | 351a | Protein Destination; Signal Transduction; Cellular Organization; | YDR508C | GNP1 | 351b | Metabolism; Transport Organization; |
| YDR115W | | 352a | Protein Synthesis; | YKL142W | MRP8 | 352b | Protein Synthesis; Cellular Organization; |
| YER102W | RPS8B | 353a | Protein Synthesis; Cellular Organization; | YBR135W | CKS1 | 353b | Cell Growth, Cell Division And DNA Synthesis; |
| YOR276W | CAF20 | 354a | Protein Synthesis; Cellular Organization; | YOL139C | CDC33 | 354b | Cell Growth, Cell Division And DNA Synthesis; Protein Synthesis; Cellular Organization; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YKL142W | MRP8 | 355a | Protein Synthesis; Cellular Organization; | YMR165C | SMP2 | 355b | Energy; Cell Growth, Cell Division And DNA Synthesis; Cellular Biogenesis; |
| YKR026C | GCN3 | 356a | Protein Synthesis; Cellular Organization; | YKR026C | GCN3 | 356b | Protein Synthesis; Cellular Organization; |
| YKL142W | MRP8 | 357a | Protein Synthesis; Cellular Organization; | YKL142W | MRP8 | 357b | Protein Synthesis; Cellular Organization; |
| YMR309C | NIP1 | 358a | Protein Synthesis; Cellular Organization; | YNL244C | SUI1 | 358b | Protein Synthesis; Cellular Organization; |
| YLR264W | RPS28B | 359a | Protein Synthesis; Cellular Organization; | YOL149W | DCP1 | 359b | Transcription; |
| YLR291C | GCD7 | 360a | Protein Synthesis; Cellular Organization; | YPL070W | | 360b | Unclassified Proteins; |
| YMR309C | NIP1 | 361a | Protein Synthesis; Cellular Organization; | YNL047C | | 361b | Unclassified Proteins; |
| YMR309C | NIP1 | 362a | Protein Synthesis; Cellular Organization, | YOR284W | | 362b | Unclassified Proteins; |
| YGL189C | RPS26A | 363a | Protein Synthesis; Cellular Organization; | YLR435W | | 363b | Unclassified Proteins; |
| YER131W | RPS26B | 364a | Protein Synthesis; Cellular Organization; | YLR435W | | 364b | Unclassified Proteins; |
| YLR264W | RPS28B | 365a | Protein Synthesis; Cellular Organization; | YBR094W | | 365b | Unclassified Proteins; |
| YER102W | RPS8B | 366a | Protein Synthesis; Cellular Organization; | YFL017C | | 366b | Unclassified Proteins; |
| YDR429C | TIF35 | 367a | Protein Synthesis; Cellular Organization; | YFL017C | | 367b | Unclassified Proteins; |
| YCR02OC-A | MAK31 | 368a | Retrotransposons And Plasmid Proteins; | YEL053C | MAK10 | 368b | Energy; |
| YHR158C | KEL1 | 369a | Sional Transduction; | YOR047C | STD1 | 369b | Metabolism; Transcription; |
| YHR158C | KEL1 | 370a | Signal Transduction; | YJR122W | CAF17 | 370b | Transcription; Cellular Organization; |
| YHR158C | KEL1 | 371a | Signal Transduction; | YMR181C | | 371b | Unclassified Proteins; |
| YCR027C | | 372a | Signal Transduction; | YOL083W | | 372b | Unclassified Proteins; |
| YHL002W | | 373a | Signal Transduction; | YNR005C | | 373b | Unclassified Proteins; |
| YKL166C | TPK3 | 374a | Signal Transduction; Cellular Organization; | YIL033C | SRA1 | 374b | Metabolism; Cell Growth, Cell Division And DNA Synthesis; Cell Rescue, Defense, Cell Death And Aging; Cellular Organization; |
| YDR017C | KCS1 | 375a | Transcription; | YDR099W | BMH2 | 375b | Cell Growth, Cell Division And DNA Synthesis; |
| YOR025W | HST3 | 376a | Transcription; | YLR403W | SFP1 | 376b | Cell Growth, Cell Division And DNA Synthesis; Cellular Organization; |
| YIL105C | | 377a | Transcription; | YER179W | DMC1 | 377b | Cell Growth, Cell Division And DNA Synthesis; Cellular Organization; |
| YDR026C | | 378a | Transcription; | YDR110W | FOB1 | 378b | Cell Growth, Cell Division And DNA Synthesis; Cellular Organization; |
| YIL105C | | 379a | Transcription; | YKL130C | SHE2 | 379b | Cell Growth, Cell Division And DNA Synthesis; Cellular Organization; |
| YML015C | TAF40 | 380a | Transcription; | YDR174W | | 380b | Cellular Organization; |
| YGL150C | INO80 | 381a | Transcription; | YOR355W | GDS1 | 381b | Classification Not Yet Clear-Cut; |
| YGL150C | INO80 | 382a | Transcription; | YDL002C | NHP10 | 382b | Classification Not Yet Clear-Cut; |
| YER127W | LCP5 | 383a | Transcription; | YDR299W | BFR2 | 383b | Intracellular Transpon; |
| YPR107C | YTH1 | 384a | Transcription; | YBR205W | KTR3 | 384b | Metabolism; Protein Destination; |
| YGR221C | NIF3 | 385a | Transcription; | YGR221C | NIF3 | 385b | Transcription; |
| YML015C | TAF40 | 386a | Transcription; | YDR167W | TAF25 | 386b | Transcription; Cellular Organization; |
| YPR107C | YTH1 | 387a | Transcription; | YJR093C | FIP1 | 387b | Transcription; Cellular Organization; |
| YDR439W | LRS4 | 388a | Transcription; | YCR086W | | 388b | Unclassified Proteins; |
| YCR004C | YCP4 | 389a | Transcription; | YDR032C | | 389b | Unclassified Proteins; |
| YER116C | | 390a | Transcription; | YGR024C | | 390b | Unclassified Proteins; |
| YIL105C | | 391a | Transcription; | YNL047C | | 391b | Unclassified Proteins; |
| YIR005W | | 392a | Transcription; | YGL174W | | 392b | Unclassified Proteins; |
| YDR311W | TFB1 | 393a | Transcription; Cell Rescue, Defense, Cell Death And Aging; Cellular Organization; | YGR120C | | 393b | Intracellular Transport; Cellular Organization; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YDR311W | TFB1 | 394a | Transcription; Cell Rescue, Defense, Cell Death And Aging; Cellular Organization; | YKL103C | LAP4 | 394b | Protein Destination; Cellular Organization; |
| YDR311W | TFB1 | 395a | Transcription; Cell Rescue, Defense, Cell Death And Aging; Cellular Organization; | YOL082W | | 395b | Unclassified Proteins; |
| YDR225W | HTA1 | 396a | Transcription; Cellular Organization; | YKR048C | NAP1 | 396b | Cell Growth, Cell Division And DNA Synthesis; Protein Destination; Cellular Biogenesis; Cellular Organization; |
| YMR112C | | 397a | Transcription; Cellular Organization; | YBR253W | SRB6 | 397b | Metabolism; Cell Growth, Cell Division And DNA Synthesis; Transcription; Cellular Organization; |
| YGR208W | SIP2 | 398a | Transcription; Cellular Organization; | YGL115W | SNF4 | 398b | Metabolism; Transcription; Cell Rescue, Defense, Cell Death And Aging; Cellular Organization; |
| YGL122C | NAB2 | 399a | Transcription; Cellular Organization; | YKR026C | GCN3 | 399b | Protein Synthesis; Cellular Organization; |
| YDL160C | DHH1 | 400a | Transcription; Cellular Organization; | YOL149W | DCP1 | 400b | Transcription; |
| YGR158C | MTR3 | 401a | Transcription; Cellular Organization; | YDL111C | RRP42 | 401b | Transcription; |
| YKL028W | TFA1 | 402a | Transcription; Cellular Organization; | YDR311W | TFB1 | 402b | Transcription; Cell Rescue, Defense, Cell Death And Aging; Cellular Organization; |
| YGL237C | HAP2 | 403a | Transcription; Cellular Organization; | YBL021C | HAP3 | 403b | Transcription; Cellular Organization; |
| YGL237C | HAP2 | 404a | Transcription; Cellular Organization; | YOR358W | HAP5 | 404b | Transcription; Cellular Organization; |
| YBL021C | HAP3 | 405a | Transcription; Cellular Organization; | YOR358W | HAP5 | 405b | Transcription; Cellular Organization; |
| YOL123W | HRP1 | 406a | Transcription; Cellular Organization; | YGL122C | NAB2 | 406b | Transcription; Cellular Organization; |
| YOL135C | MED7 | 407a | Transcription; Cellular Organization; | YOR174W | MED4 | 407b | Transcription; Cellular Organization; |
| YPR110C | RPC40 | 408a | Transcription; Cellular Organization; | YNL113W | RPC19 | 408b | Transcription; Cellular Organization; |
| YJL025W | RRN7 | 409a | Transcription; Cellular Organization; | YBL014C | RRN6 | 409b | Transcription; Cellular Organization; |
| YMR270C | RRN9 | 410a | Transcription; Cellular Organization; | YBL025W | RRN10 | 410b | Transcription; Cellular Organization; |
| YOR159C | SME1 | 411a | Transcription; Cellular Organization; | YPR182W | SMX3 | 411b | Transcription; Cellular Organization; |
| YPR182W | SMX3 | 412a | Transcription; Cellular Organization; | YLR275W | SMD2 | 412b | Transcription; Cellular Organization; |
| YGR104C | SRB5 | 413a | Transcription; Cellular Organization; | YBR193C | MED8 | 413b | Transcription; Cellular Organization; |
| YDR308C | SRB7 | 414a | Transcription; Cellular Organization; | YOR174W | ME04 | 414b | Transcription; Cellular Organization; |
| YDR308C | SRB7 | 415a | Transcription; Cellular Organization; | YOL135C | MED7 | 415b | Transcription; Cellular Organization; |
| YGL112C | TAF60 | 416a | Transcription; Cellular Organization; | YMR236W | TAF17 | 416b | Transcription; Cellular Organization; |
| YKL028W | TFA1 | 417a | Transcription; Cellular Organization; | YKR062W | TFA2 | 417b | Transcription; Cellular Organization; |
| YOR210W | RPB10 | 418a | Transcription; Cellular Organization; | YGL166W | CUP2 | 418b | Transcription; Ionic Homeostasis; Cellular Organization; |
| YIR018W | YAP5 | 419a | Transcription; Cellular Organization; | YGL071W | RCS1 | 419b | Transcription; Ionic Homeostasis; Cellular Organization; |
| YDL160C | DHH1 | 420a | Transcription; Cellular Organization; | YEL015W | | 420b | Unclassified Proteins; |
| YPR110C | RPC40 | 421a | Transcription; Cellular Organization; | YLR238W | | 421b | Unclassified Proteins; |
| YDL150W | RPC53 | 422a | Transcription; Cellular Organization; | YKR025W | | 422b | Unclassified Proteins; |
| YDR088C | SLU7 | 423a | Transcription; Cellular Organization; | YDL144C | | 423b | Unclassified Proteins; |
| YMR039C | SUB1 | 424a | Transcription; Cellular Organization; | YMR316C-B | | 424b | Unclassified Proteins; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YGL112C | TAF60 | 425a | Transcription; Cellular Organization; | YMR255W | | 425b | Unclassified Proteins; |
| YDR002W | | 426a | Transcription; Intracellular Transport; Cellular Organization; | YKR048C | NAP1 | 426b | Cell Growth, Cell Division And DNA Synthesis; Protein Destination; Cellular Biogenesis; Cellular Organization; |
| YLR293C | GSP1 | 427a | Transcription; Intracellular Transport; Cellular Organization; | YJR074W | MOG1 | 427b | Unclassified Proteins; |
| YOR185C | GSP2 | 428a | Transcription; Intracellular Transport; Cellular Organization; | YJR074W | MOG1 | 428b | Unclassified Proteins; |
| YLR216C | CPR6 | 429a | Transcription; Protein Destination; Cellular Organization; | YIR037W | HYR1 | 429b | Cell Rescue, Defense, Cell Death And Aging; |
| YBR237W | PRP5 | 430a | Transcription; Protein Destination; Cellular Organization; | YDR073W | SNF11 | 430b | Metabolism; Cell Growth, Cell Division And DNA Synthesis; Transcription; Cellular Organization; |
| YGR252W | GCN5 | 431a | Transcription; Protein Destination; Cellular Organization; | YDR448W | ADA2 | 431b | Transcription; Cellular Organization; |
| YBR052C | | 432a | Transport Facilitation; | YDR032C | | 432b | Unclassified Proteins; |
| YKR104W | | 433a | Transport Facilitation; Cell Rescue, Defense, Cell Death And Aging; | YOL143C | RIB4 | 433b | Metabolism; |
| YLL028W | | 434a | Transport Facilitation; Cell Rescue, Defense, Cell Death And Aging; | YGL166W | CUP2 | 434b | Transcription; Ionic Homeostasis; Cellular Organization; |
| YIL013C | PDR11 | 435a | Transport Facilitation; Cellular Organization; | YDR174W | | 435b | Cellular Organization; |
| YOL130W | ALR1 | 436a | Transport Facilitation; Intracellular Transport; Cell Rescue, Defense, Cell Death And Aging; Ionic Homeostasis; Cellular Organization; | YGL025C | PGD1 | 436b | Cell Growth, Cell Division And DNA Synthesis; Transcription; Cellular Organization; |
| YOL130W | ALR1 | 437a | Transport Facilitation; Intracellular Transport; Cell Rescue, Defense, Cell Death And Aging; Ionic Homeostasis; Cellular Organization; | YLR291C | GCD7 | 437b | Protein Synthesis; Cellular Organization; |
| YMR243C | ZRC1 | 438a | Transport Facilitation; Intracellular Transport; Cell Rescue, Defense, Cell Death And Aging; Ionic Homeostasis; Cellular Organization; | YKL142W | MRP8 | 438b | Protein Synthesis; Cellular Organization; |
| YOL130W | ALR1 | 439a | Transport Facilitation; Intracellular Transport; Cell Rescue, Defense, Cell Death And Aging; Ionic Homeostasis; Cellular Organization; | YGL024W | | 439b | Unclassified Proteins; |
| YOL130W | ALR1 | 440a | Transport Facilitation; Intracellular Transport; Cell Rescue, Defense, Cell Death And Aging; Ionic Homeostasis; Cellular Organization; | YNL086W | | 440b | Unclassified Proteins; |
| YFL060C | SNO3 | 441a | Unclassified Proteins; | YMR096W | SNZ1 | 441b | Cell Growth, Cell Division And DNA Synthesis; |
| YDL012C | | 442a | Unclassified Proteins; | YDR151C | CTH1 | 442b | Cell Growth, Cell Division And DNA Synthesis; |
| YIL065C | | 443a | Unclassified Proteins; | YJR091C | JSN1 | 443b | Cell Growth, Cell Division And DNA Synthesis; |
| YLR392C | | 444a | Unclassified Proteins; | YJR091C | JSN1 | 444b | Cell Growth, Cell Division And DNA Synthesis; |
| YDR214W | | 445a | Unclassified Proteins; | YJL030W | MAD2 | 445b | Cell Growth, Cell Division And DNA Synthesis; |
| YNL127W | | 446a | Unclassified Proteins; | YKR055W | RHO4 | 446b | Cell Growth, Cell Division And DNA Synthesis; |
| YGR278W | | 447a | Unclassified Proteins; | YGR049W | SCM4 | 447b | Cell Growth, Cell Division And DNA Synthesis; |
| YMR322C | | 448a | Unclassified Proteins; | YMR096W | SNZ1 | 448b | Cell Growth, Cell Division And DNA Synthesis; |
| YBR190W | | 449a | Unclassified Proteins; | YLR117C | SYF3 | 449b | Cell Growth, Cell Division And DNA Synthesis; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YDL012C | | 450a | Unclassified Proteins; | YJL065C | | 450b | Cell Growth, Cell Division And DNA Synthesis; |
| YNR029C | | 451a | Unclassified Proteins; | YJL065C | | 451b | Cell Growth, Cell Division And DNA Synthesis; |
| YGL061C | DUO1 | 452a | Unclassified Proteins; | YER016W | BIM1 | 452b | Cell Growth, Cell Division And DNA Synthesis; Cellular Biogenesis; Cellular Organization; |
| YOR353C | | 453a | Unclassified Proteins; | YHR102W | NRKl1 | 453b | Cell Growth, Cell Division And DNA Synthesis; Cellular Biogenesis; |
| YBR141C | | 454a | Unclassified Proteins; | YGL091C | NBP35 | 454b | Cell Growth, Cell Division And DNA Synthesis; Cellular Organization; |
| YGR154C | | 455a | Unclassified Proteins; | YCR057C | PWP2 | 455b | Cell Growth, Cell Division And DNA Synthesis; Cellular Organization; |
| YGR017W | | 456a | Unclassified Proteins; | YLR403W | SFPl | 456b | Cell Growth, Cell Division And DNA Synthesis; Cellular Organization; |
| YJL048C | | 457a | Unclassified Proteins; | YKL130C | SHE2 | 457b | Cell Growth, Cell Division And DNA Synthesis; Cellular Organization; |
| YPR020W | | 458a | Unclassified Proteins; | YKL130C | SHE2 | 458b | Cell Growth, Cell Division And DNA Synthesis; Cellular Organization; |
| YDL239C | | 459a | Unclassified Proteins; | YHR184W | SSP1 | 459b | Cell Growth, Cell Division And DNA Synthesis; Cellular Organization; |
| YNL078W | | 460a | Unclassified Proteins; | YKR048C | NAP1 | 460b | Cell Growth, Cell Division And DNA Synthesis; Protein Destination; Cellular Biogenesis; Cellular Organization; |
| YDR315C | | 461a | Unclassified Proteins; | YJR117W | STE24 | 461b | Cell Growth, Cell Division And DNA Synthesis; Protein Destination; Cellular Organization; |
| YLR200W | YKE2 | 462a | Unclassified Proteins; | YMR052W | FAR3 | 462b | Cell Growth, Cell Division And DNA Synthesis; Signal Transduction; |
| YDR200C | | 463a | Unclassified Proteins; | YMR052W | FAR3 | 463b | Cell Growth, Cell Division And DNA Synthesis; Signal Transduction; |
| YDR032C | | 464a | Unclassified Proteins; | YCL032W | STE50 | 464b | Cell Growth, Cell Division And DNA Synthesis; Signal Transduction; |
| YNL127W | | 465a | Unclassified Proteins; | YAL016W | TPD3 | 465b | Cell Growth, Cell Division And DNA Synthesis; Transcription; |
| YIL065C | | 466a | Unclassified Proteins; | YLR321C | SFH1 | 466b | Cell Growth, Cell Division And DNA Synthesis; Transcription; Cellular Biogenesis; Cellular Organization; |
| YIL132C | | 467a | Unclassified Proteins; | YLR321C | SFH1 | 467b | Cell Growth, Cell Division And DNA Synthesis; Transcription; Cellular Biogenesis; Cellular Organization; |
| YGL230C | | 468a | Unclassified Proteins; | YKL110C | KTI12 | 466b | Cell Rescue, Defense, Cell Death And Aging; |
| YBL101W-A | | 469a | Unclassified Proteins; | YBL043W | ECM13 | 469b | Cellular Biogenesis; |
| YGR068C | | 470a | Unclassified Proteins; | YBL102W | SFT2 | 470b | Cellular Organization; |
| YKL090W | | 471a | Unclassified Proteins; | YPL128C | TBF1 | 471b | Cellular Organization; |
| YPR260W | | 472a | Unclassified Proteins; | YIL144W | TID3 | 472b | Cellular Organization; |
| YKL002W | | 473a | Unclassified Proteins; | YMR117C | | 473b | Cellular Organization; |
| YBR141C | | 474a | Unclassified Proteins; | YDR372C | | 474b | Cellular Organization; Unclassified Proteins; |
| YMR095C | SNO1 | 475a | Unclassified Proteins; | YNL333W | SNZ2 | 475b | Classification Not Yet Clear-Cut; |
| YFL060C | SNO3 | 476a | Unclassified Proteins; | YNL333W | SNZ2 | 476b | Classification Not Yet Clear-Cut; |
| YDL012C | | 477a | Unclassified Proteins; | YOR355W | GDS1 | 477b | Classlfication Not Yet Clear-Cut; |
| YNL091W | | 478a | Unclassified Proteins; | YOR355W | GDS1 | 478b | Classification Not Yet Clear-Cut; |
| YMR312W | | 479a | Unclassified Proteins; | YHR187W | IKI1 | 479b | Classification Not Yet Clear-Cut; |
| YMR322C | | 480a | Unclassified Proteins; | YNL333W | SNZ2 | 480b | Classification Not Yet Clear-Cut; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YMR322C | | 481a | Unclassified Proteins; | YFL059W | SNZ3 | 481b | Classification Not Yet Clear-Cut; |
| YDR071C | | 482a | Unclassified Proteins; | YBR125C | | 482b | Classification Not Yet Clear-Cut; |
| YDR482C | | 483a | Unclassified Proteins; | YGL028C | | 483b | Classification Not Yet Clear-Cut; |
| YMR102C | | 484a | Unclassified Proteins; | YNR218W | | 484b | Classification Not Yet Clear-Cut; |
| YJL112W | | 485a | Unclassified Proteins; | YLL001W | DNM1 | 485b | Intracelular Transport; Cellular Biogenesis; |
| YDR472W | | 486a | Unclassified Proteins; | YKR068C | BET3 | 486b | Intracellular Transport; Cellular Organization; |
| YDR128W | | 487a | Unclassified Proteins; | YLR208W | SEC13 | 487b | Intracellular Transport; Cellular Organization; |
| YPR105C | | 488a | Unclassified Proteins; | YGL145W | TIP20 | 488b | Intracellular Transport; Cellular Organization; |
| YAL034W-A | | 489a | Unclassified Proteins; | YGR120C | | 489b | Intracellular Transport; Cellular Organization; |
| YDR472W | | 490a | Unclassified Proteins; | YBR254C | | 490b | Intracellular Transport; Cellular Organization; |
| YER157W | | 491a | Unclassified Proteins; | YGR120C | | 491b | Intracellular Transport; Cellular Organization; |
| YNR025C | | 492a | Unclassified Proteins; | YGR120C | | 492b | Intracellular Transport; Cellular Organization; |
| YOR353C | | 493a | Unclassified Proteins; | YGR120C | | 493b | Intracellular Transport; Cellular Organization; |
| YPR105C | | 494a | Unclassified Proteins; | YGR120C | | 494b | Intracellular Transport; Cellular Organization; |
| YFL010C | | 495a | Unclassified Proteins; | YDR515W | SLF1 | 495b | Ionic Homeostasis; |
| YEL041W | | 496a | Unclassified Proteins; | YJR049C | UTR1 | 496b | Ionic Homeostasis; |
| YGR163W | GTR1 | 497a | Unclassified Proteins; | YML121W | GTR1 | 497b | Metabolism; |
| YNL311C | | 498a | Unclassified Proteins; | YKL001C | MET14 | 498b | Metabolism; |
| YOR138C | | 499a | Unclassified Proteins; | YEL062W | NPR2 | 499b | Metabolism; |
| YLL062C | | 500a | Unclassified Proteins; | YOL143C | RIB4 | 500b | Metabolism; |
| YBL101W-A | | 501a | Unclassified Proteins; | YNR229C | URE2 | 501b | Metabolism; |
| YDL012C | | 502a | Unclassified Proteins; | YFR047C | | 502b | Metabolism; |
| YDR132C | | 503a | Unclassified Proteins; | YJL218W | | 503b | Metabolism; |
| YGR294W | | 504a | Unclassified Proteins; | YHL018W | | 504b | Metabolism; |
| YIL008W | | 505a | Unclassified Proteins; | YHR111W | | 505b | Metabolism; |
| YNL311C | | 506a | Unclassified Proteins; | YIL074C | | 506b | Metabolism; |
| YFR042W | | 507a | Unclassified Proteins; | YPR159W | KRE6 | 507b | Metabolism; Cell Growth, Cell Division And DNA Synthesis; Cellular Biogenesis; Cellular Organization; |
| YML088W | | 508a | Unclassified Proteins; | YDR328C | SKP1 | 508b | Metabolism; Cell Growth, Cell Division And DNA Synthesis; Protein Destination; Cellular Organization; |
| YGR122W | | 509a | Unclassified Proteins; | YLR025W | SNF7 | 509b | Metabolism; Cell Growth, Cell Division And DNA Synthesis; Protein Destination; Cellular Organization; |
| YMR025W | | 510a | Unclassified Proteins; | YNR052C | POP2 | 510b | Metabolism; Cell Growth, Cell Division And DNA Synthesis; Transcription; Cellular Organization; |
| YML068W | | 511a | Unclassified Proteins; | YDR073W | SNF11 | 511b | Metabolism; Cell Growth, Cell Division And DNA Synthesis; Transcription; Cellular Organization; |
| YNL094W | | 512a | Unclassified Proteins; | YNL025C | SSN8 | 512b | Metabolism; Cell Growth, Cell Division And DNA Synthesis; Transcription; Cellular Organization; |
| YDR215C | | 513a | Unclassified Proteins; | YPL175W | SPT14 | 513b | Metabolism; Cellular Biogenesis; Cellular Organization; |
| YAL032C | FUN20 | 514a | Unclassified Proteins; | YLR345W | | 514b | Metabolism; Energy; |
| YLR465C | | 515a | Unclassified Proteins; | YML035C | AMD1 | 515b | Metabolism; Energy; |
| YDL012C | | 516a | Unclassified Proteins; | YIL172C | | 516b | Metabolism; Energy; |
| YAR014C | | 517a | Unclassified Proteins; | YER133W | GLC7 | 517b | Metabolism; Energy; Cell Growth, Cell Division And DNA Synthesis; Protein Synthesis; Cellular Organization; |
| YML053C | | 518a | Unclassified Proteins; | YJR009C | TDH2 | 518b | Metabolism; Energy; Cellular Organization; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YGR058W | | 519a | Unclassified Proteins; | YLR113W | HOG1 | 519b | Metabolism; Signal Transduction; Cell Rescue, Defense, Cell Death And Aging; |
| YCL046W | | 520a | Unclassified Proteins; | YGL115W | SNF4 | 520b | Metabolism; Transcription; Cell Rescue, Defense, Cell Death And Aging; Cellular Organization; |
| YPL039W | MET31 | 521a | Unclassified Proteins; | YEL009C | GCN4 | 521b | Metabolism; Transcription; Cellular Organization; |
| YGR242C | | 522a | Unclassified Proteins; | YKR099W | BAS1 | 522b | Metabolism; Transcription; Cellular Organization; |
| YDL076C | | 523a | Unclassified Proteins; | YLR098C | CHA4 | 523b | Metabolism; Transcription; Cellular Organization; |
| YDL239C | | 524a | Unclassified Proteins; | YLR098C | CHA4 | 524b | Metabolism; Transcription; Cellular Organization; |
| YHR145C | | 525a | Unclassified Proteins; | YEL009C | GCN4 | 525b | Metabolism; Transcription; Cellular Organization; |
| YDL110C | | 526a | Unclassified Proteins; | YKL015W | PUT3 | 526b | Metabolism; Transcription; Cellular Organization; |
| YGL230C | | 527a | Unclassified Proteins; | YDL210W | UGA4 | 527b | Metabolism; Transport Facilitation; Intracellular Transport; Cellular Organization; |
| YPR222W | | 528a | Unclassified Proteins; | YGR048W | UFD1 | 528b | Protein Destination; |
| YIL151C | | 529a | Unclassified Proteins; | YLR121C | YPS4 | 529b | Protein Destination; |
| YLL049W | | 530a | Unclassified Proteins; | YNR069C | | 530b | Protein Destination; |
| YNR068C | | 531a | Unclassified Proteins; | YNR069C | | 531b | Protein Destination; |
| YAR031W | | 532a | Unclassified Proteins; | YBR217W | | 532b | Protein Destination; Cellular Biogenesis; Cellular Organization; |
| YAL034W-A | | 533a | Unclassified Proteins; | YKL103C | LAP4 | 533b | Protein Destination; Cellular Organization; |
| YPL019C | | 534a | Unclassified Proteins; | YHR060W | VMA22 | 534b | Protein Destination; Cellular Organization; |
| YPR105C | | 535a | Unclassified Proteins; | YHR060W | VMA22 | 535b | Protein Destination; Cellular Organization; |
| YOL105C | WSC3 | 536a | Unclassified Proteins; | YGL153W | PEX14 | 536b | Protein Destination; Intracellular Transport; Cellular Organization; |
| YBR077C | | 537a | Unclassified Proteins; | YMR004W | MVP1 | 537b | Protein Destination; Intracellular Transport; Cellular Organization; |
| YPL151C | | 538a | Unclassified Proteins; | YOR036W | PEP12 | 538b | Protein Destination; Intracellular Transport; Cellular Organization; |
| YPR105C | | 539a | Unclassified Proteins; | YGL153W | PEX14 | 539b | Protein Destination; Intracellular Transport; Cellular Organization; |
| YDR482C | | 540a | Unclassified Proteins; | YOR276W | CAF20 | 540b | Protein Synthesis; Cellular Organization; |
| YBR270C | | 541a | Unclassified Proteins; | YKR026C | GCN3 | 541b | Protein Synthesis; Cellular Organization; |
| YER186C | | 542a | Unclassified Proteins; | YKR026C | GCN3 | 542b | Protein Synthesis; Cellular Organization; |
| YMR269W | | 543a | Unclassified Proteins; | YKR026C | GCN3 | 543b | Protein Synthesis; Cellular Organization; |
| YER082C | | 544a | Unclassified Proteins; | YKL142W | MRP8 | 544b | Protein Synthesis; Cellular Organization; |
| YMR210W | | 545a | Unclassified Proteins; | YKL142W | MRP8 | 545b | Protein Synthesis; Cellular Organization; |
| YDL063C | | 546a | Unclassified Proteins; | YPL131W | RPL5 | 546b | Protein Synthesis; Cellular Organization; |
| YLL027W | | 547a | Unclassified Proteins; | YGL189C | RPS26A | 547b | Protein Synthesis; Cellular Organization; |
| YLL027W | | 548a | Unclassified Proteins; | YER131W | RPS26B | 548b | Protein Synthesis; Cellular Organization; |
| YDR315C | | 549a | Unclassified Proteins; | YLR264W | RPS28B | 549b | Protein Synthesis; Cellular Organization; |
| YCL020W | | 550a | Unclassified Proteins; | YFL002W-A | | 550b | Retrotransposons And Plasmid Proteins; |
| YFL010C | | 551a | Unclassified Proteins; | YGR136W | | 551b | Signal Transduction; Cellular Organization; |
| YGR058W | | 552a | Unclassified Proteins; | YGR136W | | 552b | Signal Transduction; Cellular Organization; |
| YDR416W | SYF1 | 553a | Unclassified Proteins; | YBR188C | NTC20 | 553b | Transcription; |
| YDR215C | | 554a | Unclassified Proteins; | YKR024C | DBP7 | 554b | Transcription; |
| YDR132C | | 555a | Unclassified Proteins; | YHR170W | NMD3 | 555b | Transcription; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YBR270C | | 556a | Unclassified Proteins; | YIL105C | | 556b | Transcription; |
| YDL146W | | 557a | Unclassified Proteins; | YKL070W | | 557b | Transcription; |
| YDR326C | | 558a | Unclassified Proteins; | YIL105C | | 558b | Transcription; |
| YGR250C | | 559a | Unclassified Proteins; | YIR001C | | 559b | Transcription; |
| YMR068W | | 560a | Unclassified Proteins; | YIL105C | | 560b | Transcription; |
| YPR082C | DIB1 | 561a | Unclassified Proteins; | YBR055C | PRP6 | 561b | Transcription; Cellular Organization; |
| YDR313C | PIB1 | 562a | Unclassified Proteins; | YPL133C | YPL133C | 562b | Transcription; Cellular Organization; |
| YGR068C | | 563a | Unclassified Proteins; | YGL015W | CKB1 | 563b | Transcription; Cellular Organization; |
| YMR255W | | 564a | Unclassified Proteins; | YGL122C | NAB2 | 564b | Transcription; Cellular Organization; |
| YDL098C | | 565a | Unclassified Proteins; | YGR075C | PRP38 | 565b | Transcription; Cellular Organization; |
| YFL023W | | 566a | Unclassified Proteins; | YBR154C | RPB5 | 566b | Transcription; Cellular Organization; |
| YDR255C | | 567a | Unclassified Proteins; | YKL144C | RPC25 | 567b | Transcription; Cellular Organization; |
| YDR357C | | 568a | Unclassified Proteins; | YPR182W | SMX3 | 568b | Transcription; Cellular Organization; |
| YOL106W | | 569a | Unclassified Proteins; | YPR182W | SMX3 | 569b | Transcription; Cellular Organization; |
| YBR270C | | 570a | Unclassified Proteins; | YMR236W | TAF17 | 570b | Transcription; Cellular Organization; |
| YML114C | | 571a | Unclassified Proteins; | YDR167W | TAF25 | 571b | Transcription; Cellular Organization; |
| YDL063C | | 572a | Unclassified Proteins; | YDR381W | YRA1 | 572b | Transcription; Cellular Organization; |
| YNL171C | | 573a | Unclassified Proteins; | YCR106W | | 573b | Transcription; Cellular Organization; |
| YAL034W-A | | 574a | Unclassified Proteins; | YGL172W | NUP49 | 574b | Transcription; Intracellular Transport; Cellular Organization; |
| YKR011C | | 575a | Unclassified Proteins; | YGL166W | CUP2 | 575b | Transcription; Ionic Homeostasis; Cellular Organization; |
| YML006C | | 576a | Unclassified Proteins; | YGL166W | CUP2 | 576b | Transcription; Ionic Homeostasis; Cellular Organization; |
| YOR220W | | 577a | Unclassified Proteins; | YGL166W | CUP2 | 577b | Transcription; Ionic Homeostasis; Cellular Organization; |
| YHL006C | | 578a | Unclasstfied Proteins; | YNL021W | HDA1 | 578b | Transcription; Protein Destination; Cellular Organization; |
| YDL012C | | 579a | Unclassified Proteins; | YHR032W | | 579b | Transport Facilitation; Cell Rescue, Defense, Cell Death And Aging; |
| YMR075C-A | | 580a | Unclassified Proteins; | YCR023C | | 580b | Transport Facilitation; Cell Rescue, Defense, Cell Death And Aging; |
| YGR113W | DAM1 | 581a | Unclassified Proteins; | YGL061C | DUO1 | 581b | Unclassified Proteins; |
| YGL061C | DUO1 | 582a | Unclassified Proteins; | YDR016C | | 582b | Unclassified Proteins; |
| YAL036C | FUN11 | 583a | Unclassified Proteins; | YDR152W | | 583b | Unclassified Proteins; |
| YAL032C | FUN20 | 584a | Unclassified Proteins; | YPL151C | | 584b | Unclassified Proteins; |
| YDR490C | PKH1 | 585a | Unclassified Proteins; | YHR207C | | 585b | Unclassified Proteins; |
| YDR490C | PKH1 | 586a | Unclassified Proteins; | YIR044C | | 586b | Unclassified Proteins; |
| YDR490C | PKH1 | 587a | Unclassified Proteins; | YLR466W | | 587b | Unclassified Proteins; |
| YLR082C | SRL2 | 588a | Unclassified Proteins; | YLR082C | SRL2 | 588b | Unclassified Proteins; |
| YDR416W | SYF1 | 589a | Unclassified Proteins; | YJR050W | ISY1 | 589b | Unclassified Proteins; |
| YDR416W | SYF1 | 590a | Unclassified Proteins; | YCR129W | SYF2 | 590b | Unclassified Proteins; |
| YHR016C | YSC84 | 591a | Unclassified Proteins; | YLR243W | | 591b | Unclassified Proteins; |
| YHR016C | YSC84 | 592a | Unclassified Proteins; | YMR255W | | 592b | Unclassified Proteins; |
| YHL006C | | 593a | Unclassified Proteins; | YDR078C | PUN1 | 593b | Unclassified Proteins; |
| YNL056W | | 594a | Unclassified Proteins; | YNL032W | SIW14 | 594b | Unclassified Proteins; |
| YFL023W | | 595a | Unclassified Proteins; | YLR200W | YKE2 | 595b | Unclassified Proteins; |
| YAR031W | | 596a | Unclassified Proteins; | YCR030C | | 596b | Unclassified Proteins; |
| YBL101W-A | | 597a | Unclassified Proteins, | YFL002W-A | | 597b | Unclassified Proteins, |
| YBL101W-A | | 598a | Unclassified Proteins; | YJL162C | | 598b | Unclassified Proteins; |
| YBR103W | | 599a | Unclassified Proteins; | YIL112W | | 599b | Unclassified Proteins; |
| YBR228W | | 600a | Unclassified Proteins; | YLR135W | | 600b | Unclassified Proteins; |
| YDL012C | | 601a | Unclassified Proteins; | YHR140W | | 601b | Unclassified Proteins; |
| YDL071C | | 602a | Unclassified Proteins; | YDR183W | | 602b | Unclassified Proteins; |
| YDL071C | | 603a | Unclassified Proteins; | YEL068C | | 603b | Unclassified Proteins; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YDL071C | | 604a | Unclassified Proteins; | YFL017C | | 604b | Unclassified Proteins; |
| YDL071C | | 605a | Unclassified Proteins; | YGR269W | | 605b | Unclassified Proteins; |
| YDL071C | | 606a | Unclassified Proteins; | YNL155W | | 606b | Unclassified Proteins; |
| YDL089W | | 607a | Unclassified Proteins; | YDL089W | | 607b | Unclassified Proteins; |
| YDL089W | | 608a | Unclassified Proteins; | YLR324W | | 608b | Unclassified Proteins; |
| YDL089W | | 609a | Unclassified Proteins; | YMR316C-B | | 609b | Unclassified Proteins; |
| YDL110C | | 610a | Unclassified Proteins; | YOR078W | | 610b | Unclassified Proteins; |
| YDL113C | | 611a | Unclassified Proteins; | YJL036W | | 611b | Unclassified Proteins; |
| YDL133W | | 612a | Unclassified Proteins; | YDL001W | | 612b | Unclassified Proteins; |
| YDR216C | | 613a | Unclassified Proteins; | YMR025W | | 613b | Unclassified Proteins; |
| YDR239C | | 614a | Unclassified Proteins; | YOL091W | | 614b | Unclassified Proteins; |
| YDR013W | | 615a | Unclassified Proteins; | YDR489W | | 615b | Unclassified Proteins; |
| YDR032C | | 616a | Unclassified Proteins; | YDR032C | | 616b | Unclassified Proteins; |
| YDR051C | | 617a | Unclassified Proteins; | YDR051C | | 617b | Unclassified Proteins; |
| YDR070C | | 618a | Unclassified Proteins; | YFL017C | | 618b | Unclassified Proteins; |
| YDR179C | | 619a | Unclassified Proteins; | YMR025W | | 619b | Unclassified Proteins; |
| YDR200C | | 620a | Unclassified Proteins; | YNL127W | | 620b | Unclassified Proteins; |
| YDR236C | | 621a | Unclassified Proteins; | YDR398W | | 621b | Unclassified Proteins; |
| YDR267C | | 622a | Unclassified Proteins; | YHR122W | | 622b | Unclassified Proteins; |
| YDR279W | | 623a | Unclassified Proteins; | YLR154C | | 623b | Unclassified Proteins; |
| YDR315C | | 624a | Unclassified Proteins; | YLR323C | | 624b | Unclassified Proteins; |
| YDR315C | | 625a | Unclassified Proteins; | YOR078W | | 625b | Unclassified Proteins; |
| YDR326C | | 626a | Unclassified Proteins, | YER007C-A | | 626b | Unclassified Proteins, |
| YDR348C | | 627a | Unclassified Proteins; | YMR295C | | 627b | Unclassified Proteins; |
| YEL023C | | 628a | Unclassified Proteins; | YDL011C | | 628b | Unclassified Proteins; |
| YER010C | | 629a | Unclassified Proteins; | YER010C | | 629b | Unclassified Proteins; |
| YER046W | | 630a | Unclassified Proteins; | YFL017C | | 630b | Unclassified Proteins; |
| YER063W | | 631a | Unclassified Proteins; | YAL049C | | 631b | Unclassified Proteins; |
| YER106W | | 632a | Unclassified Proteins; | YCR086W | | 632b | Unclassified Proteins; |
| YFL010C | | 633a | Unclassified Proteins; | YOR197W | | 633b | Unclassified Proteins; |
| YFR043C | | 634a | Unclassified Proteins; | YDR489W | | 634b | Unclassified Proteins; |
| YGL051W | | 635a | Unclassified Proteins; | YAR033W | | 635b | Unclassified Proteins; |
| YGL198W | | 636a | Unclassified Proteins; | YGL161C | | 636b | Unclassified Proteins; |
| YGR214W | | 637a | Unclassified Proteins; | YLR435W | | 637b | Unclassified Proteins; |
| YGR230C | | 638a | Unclassified Proteins; | YOR161C | | 638b | Unclassified Proteins; |
| YGR010W | | 639a | Unclassified Proteins; | YGR010W | | 639b | Unclassified Proteins; |
| YGR017W | | 640a | Unclassified Proteins; | YLR072W | | 640b | Unclassified Proteins; |
| YGR024C | | 641a | Unclassified Proteins; | YGR024C | | 641b | Unclassified Proteins; |
| YGR058W | | 642a | Unclassified Proteins; | YGR058W | | 642b | Unclassified Proteins; |
| YGR058W | | 643a | Unclassified Proteins; | YNL047C | | 643b | Unclassified Proteins; |
| YGR173W | | 644a | Unclassified Proteins; | YDR152W | | 644b | Unclassified Proteins; |
| YIL007C | | 645a | Unclassified Proteins; | YHR185C | | 645b | Unclassified Proteins; |
| YIL082W | | 646a | Unclassified Proteins; | YGR024C | | 646b | Unclassified Proteins; |
| YIL132C | | 647a | Unclassified Proteins; | YLR322W | | 647b | Unclassified Proteins; |
| YIL132C | | 648a | Unclassified Proteins; | YLR376C | | 648b | Unclassified Proteins; |
| YIL151C | | 649a | Unclassified Proteins; | YBL051C | | 649b | Unclassified Proteins; |
| YIL151C | | 650a | Unclassified Proteins; | YDR140W | | 650b | Unclassified Proteins; |
| YJR024C | | 651a | Unclassified Proteins; | YJR024C | | 651b | Unclassified Proteins; |
| YJR072C | | 652a | Unclassified Proteins; | YLR243W | | 652b | Unclassified Proteins; |
| YJR072C | | 653a | Unclassified Proteins; | YOR262W | | 653b | Unclassified Proteins; |
| YJR125C | | 654a | Unclassified Proteins; | YOR111W | | 654b | Unclassified Proteins; |
| YJR136C | | 655a | Unclassified Proteins; | YKL033W | | 655b | Unclassified Proteins; |
| YKL090W | | 656a | Unclassified Proteins; | YGR024C | | 656b | Unclassified Proteins; |
| YKR007W | | 657a | Unclassified Proteins, | YBR077C | | 657b | Unclassified Proteins, |
| YKR022C | | 658a | Unclassified Proteins; | YBL010C | | 658b | Unclassified Proteins; |
| YKR060W | | 659a | Unclassified Proteins; | YDR179C | | 659b | Unclassified Proteins; |
| YKR083C | | 660a | Unclassified Proteins; | YKL052C | | 660b | Unclassified Proteins; |
| YLR015W | | 661a | Unclassified Proteins; | YDR469W | | 661b | Unclassified Proteins; |
| YLR065C | | 662a | Unclassified Proteins; | YDL149W | | 662b | Unclassified Proteins; |
| YLR315W | | 663a | Unclassified Proteins; | YDR383C | | 663b | Unclassified Proteins; |
| YLR328W | | 664a | Unclassified Proteins; | YGR010W | | 664b | Unclassified Proteins; |
| YLR328W | | 665a | Unclassified Proteins; | YLR328W | | 665b | Unclassified Proteins; |
| YLR424W | | 666a | Unclassified Proteins; | YKR022C | | 666b | Unclassified Proteins; |
| YML119W | | 667a | Unclassified Proteins; | YLL032C | | 667b | Unclassified Proteins; |
| YMR093W | | 668a | Unclassified Proteins; | YDR398W | | 668b | Unclassified Proteins; |
| YNL056W | | 669a | Unclassified Proteins; | YNL099C | | 669b | Unclassified Proteins; |
| YNL086W | | 670a | Unclassified Proteins; | YKL061W | | 670b | Unclassified Proteins; |
| YNL091W | | 671a | Unclassified Proteins; | YKL075C | | 671b | Unclassified Proteins; |
| YNL091W | | 672a | Unclassified Proteins; | YNL164C | | 672b | Unclassified Proteins; |
| YNL091W | | 673a | Unclassified Proteins; | YNL288W | | 673b | Unclassified Proteins; |

TABLE 3-continued

Protein Pairs Identified in the Screen.

| Binding Domain Fusion "Bait" [ORF] | Binding Domain Fusion [Gene] | Pro-Pair Ref. No. | Functional Classification (MIPS) | Activation Domain Fusion "Prey" [ORF] | Activation Domain Fusion [Gene] | Pro-Pair Ref. No. | Functional Classification (MIPS) |
|---|---|---|---|---|---|---|---|
| YNL091W | | 674a | Unclassified Proteins; | YPR229W | | 674b | Unclassified Proteins; |
| YNL094W | | 675a | Unclassified Proteins; | YAL049C | | 675b | Unclassified Proteins; |
| YNL122C | | 676a | Unclassified Proteins; | YKL061W | | 676b | Unclassified Proteins; |
| YNR004W | | 677a | Unclassified Proteins; | YPL157W | | 677b | Unclassified Proteins; |
| YNR029C | | 678a | Unclassified Proteins; | YJL064W | | 678b | Unclassified Proteins; |
| YOL070C | | 679a | Unclassified Proteins; | YNL078W | | 679b | Unclassified Proteins; |
| YOR023C | | 680a | Unclassified Proteins; | YCR082W | | 680b | Unclassified Proteins; |
| YCR138C | | 681a | Unclassified Proteins, | YGR268C | | 681b | Unclassified Proteins; |
| YOR215C | | 682a | Unclassified Proteins; | YHR115C | | 682b | Unclassified Proteins; |
| YOR264W | | 683a | Unclassified Proteins; | YCR086W | | 683b | Unclassified Proteins; |
| YOR264W | | 684a | Unclassified Proteins; | YGR058W | | 684b | Unclassified Proteins; |
| YOR353C | | 685a | Unclassified Proteins; | YOL082W | | 685b | Unclassified Proteins; |
| YPL110C | | 686a | Unclassified Proteins; | YGR024C | | 686b | Unclassified Proteins; |
| YPL192C | | 687a | Unclassified Proteins; | YPL192C | | 687b | Unclassified Proteins; |
| YPR105C | | 688a | Unclassified Proteins; | YLR315W | | 688b | Unclassified Proteins; |
| YPR105C | | 689a | Unclassified Proteins; | YMR181C | | 689b | Unclassified Proteins; |
| YPR105C | | 690a | Unclassified Proteins; | YOR164C | | 690b | Unclassified Proteins; |
| YPR105C | | 691a | Unclassified Proteins; | YOR331C | | 691b | Unclassified Proteins; |
| YPR152C | | 692a | Unclassified Proteins; | YBR194W | | 692b | Unclassified Proteins; |

In certain embodiments, the first polypeptide is labeled. In other embodiments, the second polypeptide is labeled, while in some embodiments, both the first and second polypeptides are labeled. Labeling can be performed using any art recognized method for labeling polypeptides. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes complexes of two or more polypeptides in which at least one of the polypeptides is present as a fragment of a complex-forming polypeptide according to the invention. For example, one or more polypeptides may include an amino acid sequence sufficient to bind to its corresponding polypeptide. A binding domain of a given first polypeptide can be any number of amino acids sufficient to specifically bind to, and complex with, the corresponding second polypeptide under conditions suitable for complex formation. The binding domain can be the minimal number of amino acids required to retain binding affinity, or may be a larger fragment or derivative of the polypeptides listed in Table 3, columns 1 and 4. Procedures for identifying binding domains can be readily identified by one of ordinary skill in the art and the procedures described herein. For example, nucleic acid sequences containing various portions of a "bait" protein can be tested in a yeast two hybrid screening assay in combination with a nucleic acid encoding the corresponding "prey" protein.

In certain embodiments, the "bait" polypeptides of the complex are polypeptides categorized, for example, as a "Metabolism" protein in the MIPS database. In some embodiments, the "prey" protein of the complex is also a "Metabolism" protein, while in other embodiments the "prey" protein is, for example, an "Unclassified" protein (see Table 3; e.g., ProPair 195a–310a and ProPair 195b–310b). Other MIPS categories include, e.g., "Cell Growth/Cell Division/DNA Synthesis" proteins (see Table 2).

In other embodiments, the complexes are human ortholog complexes, chimeric complexes, or specific complexes implicated in fungal pathways, as discussed in detail below.

Polypeptides forming the complexes according to the invention can be made using techniques known in the art. For example, one or more of the polypeptides in the complex can be chemically synthesized using art-recognized methods for polypeptide synthesis. These methods are common in the art, including synthesis using a peptide synthesizer. See, e.g., *Peptide Chemistry, A Practical Textbook*, Bodasnsky, Ed. Springer-Verlag, 1988; Merrifield, *Science* 232: 241–247 (1986); Barany, et al, *Intl. J. Peptide Protein Res.* 30: 705–739 (1987); Kent, *Ann. Rev. Biochem.* 57:957–989 (1988), and Kaiser, et al, *Science* 243: 187–198 (1989).

Alternatively, polypeptides can be made by expressing one or both polypeptides from a nucleic acid and allowing the complex to form from the expressed polypeptides. Any known nucleic acids that express the polypeptides, whether yeast or human (or chimerics of these polypeptides) can be used, as can vectors and cells expressing these polypeptides. Sequences of yeast ORFs and human polypeptides as referenced in Tables 3 and 7 are publicly available, e.g. at the Saccharomyces Genome Database (SGD) and GenBank (see, e.g. Hudson et al., *Genome Res*. 7: 1169–1173 (1997). If desired, the complexes can then be recovered and isolated.

Recombinant cells expressing the polypeptide, or a fragment or derivative thereof, may be obtained using methods known in the art, and individual gene product or complex may be isolated and analyzed (See, e.g., e.g., as described in Sambrook et al., eds., MOLECULAR CLONING: A LABORATORY MANUAL, 2nd Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993). This is achieved by assays that are based upon the physical and/or functional properties of the protein or complex. The assays can include, e.g., radioactive labeling of one or more of the polypeptide complex components, followed by analysis by gel electrophoresis, immunoassay, cross-linking to marker-labeled products. Polypeptide complex may be isolated and purified by standard methods known in the art (either from natural sources or recombinant host cells expressing the proteins/protein complex). These methods can include, e.g., column chromatography (e.g., ion exchange, affinity, gel exclusion, reverse-phase, high pressure, fast protein liquid, etc), differential centrifugation, differential solubility, or similar methods used for the purification of proteins.

Complexes Useful for Identifying Anti-fungal Agents

The invention further provides complexes of polypeptides useful, inter alia, in identifying agents that inhibit the growth of microorganisms such as fungi.

Human fungal infections have increased dramatically in incidence and severity in recent years. Advances in surgery and cancer treatments as well as the increasing use of broad-spectrum antimicrobials and the spread of HIV have increased the number of patients at risk for fungal infections. Most fungi are completely resistant to conventional antibacterial drugs.

The antifungal drugs presently available fall into several categories depending on their mode of action, as discussed below. Because several complexes according to the invention include proteins associated with these modes of action, the complexes can be used to identify anti-fungal agents.

Protein interactions which are useful for identifying anti-fungal agents are considered below.

(i) Interference in Nuclear Division

Griseofulvin interferes with nuclear division in fungal mitosis by disrupting the mitotic spindle and inhibiting cytoplasmic microtubule aggregation by interacting with polymerized microtubules. There is evidence that griseofulvin binds to a microtubule-associated protein in addition to binding to tubulin.

In accordance with the present invention, several interactions have presently been identified where one of the interacting partners is a microtubule or a microtubule-associated protein. Inhibiting any of these interactions could lead to the disruption of microtubules and interference in mitotic division, similar to the mode of action of griseofulvin, thereby providing a new means of inhibiting fungal activity. Accordingly, in some embodiments, the invention provides purified complexes of the proteins detailed in Table 4, below (interacting protein pairs are in bold, by row; a description of each protein follows).

TABLE 4

| Microtubule-related interactions identified | |
|---|---|
| APG7 | AUT7 |
| Apg12p-activating enzyme, involved in autophagy cytoplasm-to-vacuole protein targeting, and peroxisome degradation pathways | Forms a protein complex with Aut2p to mediate attachment of autophagosomes to microtubules. Aut7p has homology to LC3, a microtubule-associated protein from rat |
| DUO1 | BIM1 |
| Protein that interacts with Dam1p and causes cell death upon overproduction, involved in mitotic spindle function | Microtubule binding protein |
| BUB3 | MAD3 |
| Protein required for cell cycle arrest in response to loss of microtubule function | Checkpoint protein required for cell cycle arrest in response to loss of microtubule function |
| KAR4 | MUM2 |
| Regulatory protein required for pheromone induction of karyogamy genes, defective in nuclear fusion because of defect in microtubule-dependent movement of nuclei | Muddled Meiosis, mutant is sporulation defective and fails to perform premiotic DNA synthesis |
| CLN3 | MAD3 |
| G1/S-specific cyclin that interacts with Cdc28p protein kinase to control events at START | Checkpoint protein required for cell cycle arrest in response to loss of microtubule function |
| EBS1 | MAD2 |
| Protein with similarity to Est1p (Telomere elongation protein) | Spindle-assembly checkpoint protein |
| MSB2 | MAD2 |
| Protein for which overproduction suppresses bud emergence defect of cdc24 mutant, putative integral membrane protein | Spindle-assembly checkpoint protein |
| MSB2 | MAD3 |
| Protein for which overproduction suppresses bud emergence defect of cdc24 mutant, putative integral membrane protein | Checkpoint protein required for cell cycle arrest in response to loss of microtubule function |
| NUP157 | MAD2 |
| Nuclear pore protein (nucleoporin) | Spindle-assembly checkpoint protein |
| SAP4 | MAD2 |
| Sit4p-associated protein (SIT4 is a protein phosphatase) | Spindle-assembly checkpoint protein |
| SAP4 | MAD3 |
| Sit4p-associated protein (SIT4 is a protein phosphatase) | Checkpoint protein required for cell cycle arrest in response to loss of microtubule function |
| SIN4 | MAD2 |
| Component of RNA polymerase II holoenzyme/mediator complex, involved in positive and negative regulation of transcription, possibly via changes in chromatin structure | Spindle-assembly checkpoint protein |

TABLE 4-continued

Microtubule-related interactions identified

| | |
|---|---|
| SIN4 | MAD3 |
| Component of RNA polymerase II holoenzyme/mediator complex, involved in positive and negative regulation of transcription, possibly via changes in chromatin structure | Checkpoint protein required for cell cycle arrest in response to loss of microtubule function |
| YDR214W | MAD2 |
| Protein of unknown function | Spindle-assembly checkpoint protein |
| YNL218W | MAD2 |
| Protein with similarity to E coli DNA polymerase III gamma and tau subunits | Spindle-assembly checkpoint protein |
| MCM16 | MCM22 |
| Protein involved in chromosome segregation, plays a nonessential role that governs the kinetochore-microtubule mediated process of chromosome Segregation | Protein required for maintenance of chromosomes and minichromosomes |
| CYP2 | JSN1 |
| Cyclophilin (peptidylprolyl isomerase), ER or secreted isoform, plays a role in the stress response | Benomyl dependent tubulin mutant, Protein that when overexpressed can suppress the hyperstable microtubule phenotype of tub2-150 |
| SPC34 | JSN1 |
| Protein component of the spindle pole body | Benomyl dependent tubulin mutant, Protein that when overexpressed can suppress the hyperstable microtubule phenotype of tub2-150 |
| YIL065C | JSN1 |
| Protein of unknown function | Benomyl dependent tubulin mutant, Protein that when overexpressed can suppress the hyperstable microtubule phenotype of tub2-150 |
| YLR392C | JSN1 |
| Protein of unknown function | Benomyl dependent tubulin mutant, Protein that when overexpressed can suppress the hyperstable microtubule phenotype of tub2-150 |

As described above, in certain embodiments of these complexes contain the binding domains, of the polypeptides recited in Table 4, while other embodiments contain conservative variants of these polypeptides, or polypeptides which contain the polypeptides recited in Table 4.

(ii) Disruption of Ergosterol Biosynthesis

Azoles are synthetic compounds that can be classified as imidazoles (ketoconazole, clotrimazole and miconazole) or triazoles (itraconizole and fluconazole). The antifungal activity of azole drugs result from their reduction in the biosynthesis of ergosterol, the main sterol in the cell membranes of fungi. Reduction of ergosterol alters the structure of the cytoplasmic membrane as well as the function of several membrane-bound enzymes (such as those involved in nutrient transport and chitin synthesis). The azole drugs reduce ergosterol synthesis by inhibiting the fungal cytochrome p450 enzymes, specifically they inhibit the sterol 14-alpha-demethylase, a microsomal cytochrome P450-dependent enzyme system, leading to a decrease in ergosterol and an accumulation of 14-alpha-methylsterols. There is some evidence that the primary target of the azoles is the heme protein, which cocatalyzes cytochrome P-450-dependent 14-alpha-dependent 14-alpha-demethylation of lanosterol. One interaction containing a heme biosynthesis protein has been presently been identified (Table 5). Disruption of this interaction could also lead to depletion of ergosterol and accumulation of sterol precursors, including 14-alpha-methylated sterols, forming a membrane with altered structure and function. Accordingly, in some embodiments, the invention provides a purified complex of the proteins recited in Table 5, below.

TABLE 5

Heme biosynthesis protein interaction identified

| | |
|---|---|
| SED1 | HEM13 |
| Abundant cell surface glycoprotein that may contribute to cell wall integrity and stress resistance | Coproporphyrinogen III oxidase, oxygen-repressed, sixth step in heme biosynthetic pathway |

Complexes containing one or more variants of these polypeptides are within the scope of the present invention, as are polypeptides having amino acid sequences which include the polypeptides recited in Table 5.

(iii) Cell Wall Synthesis Inhibition

Fungi share many biochemical targets with other eukaryotic cells. However, the fungal cell wall is a unique organelle and contains compounds, such as mannan, chitin and glucans, that are unique to fungi. The cell wall is dynamic and essential to the viability of the fungi due to its roles in osmotic protection, transport of macromolecules, growth, conjugation and spore formation. Major disruption of the composition or organization of the cell wall deleteriously affects cell growth. A number of compounds have been discovered that inhibit the development of fungal cell walls. Two class of these antifungal drugs are echinocandins, which inhibit glucan synthesis, and nikkomycins, which inhibit chitin synthesis.

Several interactions between proteins localized to the cell wall or enzymes responsible for production of cell wall components have presently been identified. Inhibiting any of these interactions could lead to a disruption of the cell wall, hence providing new means for inhibiting fungal viability. Accordingly, in certain embodiments, the present invention provides purified complexes of the proteins detailed in Table 6, below.

TABLE 6

Cell wall-related protein interactions identified

| | |
|---|---|
| CDC11 | SPR28 |
| Septin, component of 10 nm filaments of mother-bud neck; involved in cytokinesis | Septin-related protein expressed during sporulation |
| YFR042W | KRE6 |
| Protein of unknown function | Glucan synthase subunit required for synthesis of beta-1,6-glucan, involved in cell wall beta-glucan assembly |
| YDR482C | SCW11 |
| Protein of unknown function | Soluble cell wall protein |
| SM11 | BAS1 |
| Protein involved in (1,3)-beta-glucan synthesis, possibly through regulation of cell wall glucan and chitin synthesis; Chromatin binding protein | Transcription factor regulating basal and induced activity of histidine and adenine biosynthesis genes |
| WSC3 | PEX14 |
| Protein required for maintenance of cell wall integrity and for the stress response | Peroxisomal peripheral membrane protein (peroxin) involved in import of peroxisomal matrix proteins |

Embodiments of these complexes containing the binding domains or conservative variants of these polypeptides are within the scope of the present invention, as are polypeptides which contain the polypeptides recited in Table 6.

Complexes Containing One or More Human Polypeptides

The invention also provides purified complexes of two or more human polypeptides. In some embodiments, the interacting polypeptides are human orthologs of the interacting yeast polypeptides. Human orthologs according to the invention are set out in Table 7, below.

Complexes of human ortholog binding domains, conservative variants, and polypeptides including the human orthologs recited in Table 7, are within the scope of the invention, as are labeled ortholog complexes and/or polypeptides.

TABLE 7

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yal032c | Q13573 | SKIP | Nuclear protein Skip | ylr345w | p16118 | PFKFB1 | 6-phosphofructo-2-kinase/fructose-2,6-bisphosphatase/6PF-2-K/FRU-2,6-P2ase liver isozyme |
| yal032c | Q13573 | SKIP | Nuclear protein Skip | ylr423c | q02224 | CENPE | Centromeric protein E/CENP-E protein |
| yal032c | Q13573 | SKIP | Nuclear protein Skip | ypl151c | p35606 | COPP | Beta subunit of coatomer complex |
| yal034w-a | P06468 | TPM2 | Fibroblast muscle-type tropomyosin | ygl172w | p49790 | NUP153 | Nuclear pore complex protein NUP153. |
| yal034w-a | P07951 | TPM2 | Skeletal beta-tropomyosin | ygl172w | p35658 | NUP214 | Nuclear pore complex protein NUP214/CAN protein |
| yal034w-a | P35749 | MYH11 | Myosin heavy chain, smooth muscle isoform/SMMHC [FRAGMENT] | ygl172w | p52948 | NUP98 | Nuclear pore complex protein NUP98/Nucleoporin NUP 98 |
| yal034w-a | P49454 | CENPF | CENP-F kinetochore protein | ygl172w | p23490 | LOR | Loricrin |
| yal034w-a | Q15545 | TAF2F | Transcription initiation factor TFIID 55 kD subunit | ygl172w | p09651 | HNRPA1 | Heterogenous nuclear ribonucleoprotein A1/helix-destabilizing protein/single-strand binding protein/HNRNP core protein A1 |
| yal034w-a | P06468 | TPM2 | Fibroblast muscle-type tropomyosin | ygr120c | p49454 | CENPF | CENP-F kinetochore protein |
| yal034w-a | P07951 | TPM2 | Skeletal beta-tropomyosin | ygr120c | p30622 | RSN | Restin |
| yal034w-a | P49454 | CENPF | CENP-F kinetochore protein | ygr120c | p04114 | APOB | Apoiipoprotein B |
| yar003w | P78406 | MRNP41 | mRNA-associated protein mRNP 41 | ybr110w | o14727 | APAF1 | Apoptotic protease activating factor 1/APAF-1 |
| yar003w | Q05048 | CSTF1 | Cleavage stimulation factor, 50 kDa subunit | ybr175w | p35606 | COPP | Beta subunit of coatomer complex |
| yar003w | Q09028 | RBAP48 | Chromatin assembly factor 1 P48 subunit/retinoblastoma binding protein P48 | ybr175w | q15542 | TAF2D | Transcription initiation factor TFIID 100 Kd subunit/TAFII-100/TAFII100 |
| yar003w | Q15542 | TAF2D | Transcription initiation factor TFIID 100 Kd subunit/TAFII-100/TAFII100 | ybr175w | p04901 | GNB1 | Guanine nucleotide-binding protein G(I)/G(S)/G(T) beta subunit 1 |
| yar003w | Q16576 | RBBP7 | Histone acetyl transferase type B subunit 2/retinoblastoma-binding protein | ybr175w | p43034 | PAFAH1B1 | Platelet-activating factor acetyl-hydrolase B alpha subunit |
| yar014c | P19338 | NCL | Nucleolin/protein C23 | yer133w | p37140 | PPP1CB | Serine/threonine-protein phosphatase PP1-beta catalytic subunit |
| yar014c | P23327 | HRC | Sarcoplasmic reticulum histidine-rich calcium binding protein | yer133w | p08129 | PPP1CA | Serine/threonine protein phosphatase PP1-alpha 1 catalytic subunit |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yar014c | P35663 | CYLC1 | Cyclin I | yer133w | p05323 | PPP2CA | Serine/threonine protein phosphatase PP2A-alpha, catalytic subunit |
| yar014c | P46100 | ATRX | Transcriptional regulator ATRX/X-linked helicase II/X-linked nuclear protein | yer133w | p11082 | PPP2CB | Serine/threonine protein phosphatase PP2A-beta, catalytic subunit |
| ybl101w-a | O15016 | KIAA0298 | Hypothetical protein KIAA0298 | ybl043w | q06481 | APLP2 | Amyloid-like protein 2/APPH/amyloid protein homolog |
| ybl101w-a | O15016 | KIAA0298 | Hypothetical protein KIAA0298 | yfl002w-a | q01484 | ANK2 | Ankyrin, brain variant 1/ankyrin B |
| ybl101w-a | O15016 | KIAA0298 | Hypothetical protein KIAA0298 | yjl162c | p31689 | HSJ2 | DNAJ protein homolog 2/HSJ-2 |
| ybl105c | P05127 | PRKCB | Protein kinase C-beta-2/PKC-beta-2 | yml109w | p46821 | MAP1B | Microtubule-associated protein 1B |
| ybl105c | P17252 | PRKCA | Protein kinase C alpha | yml109w | q14669 | TRIP12 | Thyroid receptor interacting protein 12/KIAA0045 |
| ybr006w | P30837 | ALDH5 | Mitochondrial aldehyde dehydrogenase X | ydr382w | p05387 | RPLP2 | 60S acidic ribosomal protein P2 |
| ybr006w | P00352 | ALDH1 | Aldehyde dehydrogenase, cytosolic/ALDH class 1/ALDHI/ALDH-E1 | ykl023w | p35579 | MYH9 | Myosin heavy chain, nonmuscle type A/cellular myosin heavy chain, type A/NMMHC-A |
| ybr006w | P05091 | ALDH2 | Aldehyde dehydrogenase, mitochondrial/class 2/ALDHI/ALDH-E2 | ykl023w | q08170 | SFRS4 | Pre-mRNA splicing factor SRp75 |
| ybr006w | P30837 | ALDH5 | Mitochondrial aldehyde dehydrogenase X | ykl023w | p35663 | CYLC1 | Cyclin I |
| ybr006w | P47895 | ALDH6 | Aldehyde dehydrogenase 6 | ykl023w | q14093 | CYLC2 | Cylicin II |
| ybr006w | P49189 | ALDH9 | Aldehyde dehydrogenase, E3 isozyme/gamma-aminobutyraldehyde dehydrogenase | ykl023w | q14203 | DCTN1 | Dynactin, 150 kD isoform [fragment] |
| ybr006w | P51649 | SSADH | Succinate sumialdehyde dehydrogenase/NAD+-dependent succinate-semi-aldehyde dehydrogenase | ykl023w | p35580 | MYH10 | Myosin heavy chain, nonmuscle type B/cellular myosin heavy chain, type B/NMMHC-B |
| ybr103w | O14727 | APAF1 | Apoptotic protease activating factor 1/APAF-1 | yil112w | p55273 | CDKN2D | Cyclin-dependent kinase 4 inhibitor D/P19INK4D |
| ybr103w | P43034 | PAFAH1B1 | Platelet-activating factor acetyl-hydrolase IB alpha subunit | yil112w | q01484 | ANK2 | Ankyrin, brain variant 1/ankyrin B |
| ybr103w | Q15269 | PWP2H | Periodic tryptophan protein 2 homolog | yil112w | q01485 | ANK2 | Brain ankyrin variant 2 |
| ybr103w | Q15542 | TAF2D | Transcription initiation factor TFIID 100 Kd subunit/TAFII-100/TAFII100 | yil112w | p20749 | BCL3 | B-cell lymphoma 3-encoded protein |
| ybr221c | P11177 | PDHB | Pyruvate dehydrogenase E1-beta subunit | ylr345w | q16875 | F26P | 6PF-2-K/FRU-2,6-P2ase brain/placenta-type isozyme/6-phosphofructo-2-kinase/fructose-2,6-bisphosphatase |
| ybr221c | P21953 | BCKDHB | 2-oxoisovalerate dehydrogenase beta subunit | ylr345w | p16118 | PFKFB1 | 6-phosphofructo-2-kinase/fructose-2,6-bisphosphatase/6PF-2-K/FRU-2,6-P2ase liver isozyme |
| ybr221c | P51854 | TKT2 | Transketolase 2 | ylr345w | q16877 | F263 | 6PF-2-K/FRU-2,6-P2ase testis-type isozyme/6-phosphofructo-2-kinase/fructose-2,6-bisphosphatasede |
| ybr244w | P07203 | GPX1 | Glutathione peroxidase | ylr117c | q14690 | KIAA0185 | RRP5 protein homolog/KIAA0185 [fragment] |
| ybr244w | P18283 | GPX2 | Glutathione peroxidase-GI. | ylr117c | q15431 | SYCP1 | Synaptonemal complex protein 1/SCP-1 protein |
| ybr270c | P30414 | NKTR | NK-tumor recognition protein/Natural-killer cells cyclophilin-related protein | yil105c | p20226 | TBP | TATA-binding protein/transcription initiation factor TFIID |
| ybr270c | P30414 | NKTR | NK-tumor recognition protein/Natural-killer cells cyclophilin-related protein | ykr026c | q14232 | ELF2B1 | Translation initiation factor eIF-2B alpha subunit |
| ybr270c | P30414 | NKTR | NK-tumor recognition protein/Natural-killer cells cyclophilin-related protein | ylr423c | q02224 | CENPE | Centromeric protein E/CENP-E protein |
| ybr270c | P30414 | NKTR | NK-tumor recognition protein/Natural-killer cells cyclophilin-related protein | Ymr236w | q16594 | TAF2G | Transcription initiation factor TFIID 31 kD subunit |
| ybr274w | P53355 | DAPK1 | Death-associated protein kinase 1/DAP-kinase 1 | ylr258w | p54840 | GYS2 | Glycogen synthase, liver |
| ybr274w | P54646 | PRKAA2 | 5'-AMP-activated protein kinase, catalytic alpha-2 chain | ylr258w | p13807 | GYS1 | Muscle glycogen synthase |
| ybr274w | P27448 | P78 | Putative serind/threonine-protein kinase P78 | Ymr255w | p46821 | MAP1B | Microtubule-associated protein 1B |
| ybr274w | P51812 | RPS6KA3 | Ribosomal protein S6 kinase II alpha 3/insulin-stimulated protein kinase 1 | Ymr255w | p29375 | RBBP2 | RBBP-2/retinoblastoma binding protein 2 |
| ybr274w | p53355 | DAPK1 | Death-associated protein kinase 1/DAP-kinase 1 | Ymr255w | q03111 | ENL | ENL protein |
| ybr274w | p54646 | PRKAA2 | 5'-AMP-activated protein kinase, catalytic alpha-2 chain | Ymr255w | p51825 | MLLT2 | AF-4 protein |
| ybr274w | q14012 | CAMK1 | Calcium/calmodulin-dependent protein kinase type I | Ymr255w | p11387 | TOP1 | Topoisomerase I |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ybr274w | q15831 | STK11 | Serine/threonine-protein kinase 11 | Ymr255w | p46939 | UTRN | Utrophin |
| ycl020w | o15016 | KIAA0298 | Hypothetical protein KIAA0298 | yfl002w-a | q01484 | ANK2 | Ankyrin, brain variant 1/ankyrin B |
| ycl024w | p15735 | PHKG2 | Phosphorylase kinase, testis/liver, gamma-2 | ykr048c | q01105 | SET | Set protein/HLA-DR associated protein II/PHAPII |
| ycl024w | p27448 | P78 | Putative serind/threonine-protein kinase P78 | ykr048c | p46060 | RANGAP1 | RanGTPase activating protein 1 |
| ycl024w | p53355 | DAPK1 | Death-associated protein kinase 1/DAP-kinase 1 | ykr048c | q99457 | NAPIL3 | Nucleosome assembly protein 1-like3 |
| ycl024w | p54646 | PRKAA2 | 5'-AMP-activated protein kinase, catalytic alpha-2 chain | ykr048c | p55209 | NAP1L1 | NAP-1/nucleosome assembly protein 1-like 1 |
| ycl024w | q13131 | PRKAA1 | 5'-AMP-activated protein kinase, catalytic alpha-1 chain | ykr048c | o15355 | PPM1C | Protein phosphatase 2C gamma isoform/PP2C-GAMMA |
| ycl024w | q14012 | CAMK1 | Calcium/calmoduim-dependent protein kinase type I | ykr048c | q01534 | TSPY | Homo sapiens testicular protein (TSPY) mRNA, complete cds. |
| ycl024w | q15831 | STK11 | Serine/threonine-protein kinase 11 | ykr048c | p19338 | NCL | Nucleolin/protein C23 |
| ydl024w | q16566 | CAMK4 | calcium/calmodulin-dependent protein kinase IV | ykr048c | q99733 | NAP1L4 | Nucleosome assembly protein 2/nudeosome assembly protein 1-like 4 |
| ycl024w | q16816 | PHKG1 | Phosphorylase B kinase gamma catalytic chain, skeletal muscle isoform | ykr048c | p21817 | RYR1 | Ryanodine receptor 1 |
| ycl059c | p46821 | MAP1B | Microtubule-associated protein 1B | ygl201c | p49736 | MCM2 | DNA replication licensing factor MCM2/KIAA0030 |
| ydl063w | q05682 | CALD1 | Caldesmon/CDM | ylr423c | q02224 | CENPE | Centromeric protein E/CENP-E protein |
| ycr009c | p15924 | DSP | Desmoplakin I and II | ybr108w | p04280 | PRB1 | Salivary proline-rich protein/clone CP3, CP4, and CP5 |
| ycr009c | p49418 | AMPH | Amphiphysin | ybr108w | p54259 | DRPLA | Atrophin-1/dentatorubral-pallidoluysian atrophy protein |
| ydl006w | o15355 | PPM1C | Protein phosphatase 2C gamma isoform/PP2C-GAMMA | ydr162c | p46108 | CRK | Proto-oncogene C-CRK |
| ydl006w | p35813 | PPM1A | Protein phosphatase 2C alpha | ydr162c | p00519 | ABL1 | Proto-oncogene tyrosine-protein kinase ABL/c-abl |
| ydl006w | p49593 | KIAA0015 | Putative protein phosphatase 2C/PP2C/KIAA0015 | ydr162c | p51451 | BLK | Tyrosine-protein kinase BLK |
| ydl012c | p20226 | TBP | TATA-binding protein/transcription initiation factor TFIID | ydr151c | o15541 | ZNF183 | zinc finger protein 183 |
| ydl012c | p51531 | SMARCA2 | Possible global transcription activator SNF2L2/BRM | ydr151c | p26651 | ZFP36 | Tristetraproline/TTP/ZFP-36 |
| ydl012c | q10571 | MN1 | Probable tumor suppressor protein MN1 | ydr151c | p47974 | BRF2 | TIS11D protein/butyrate response factor 2/EGF-response factor 2 |
| ydl012c | q93074 | KIAA0192 | Hypothetical protein KIAA0192 | ydr151c | q07352 | BRF1 | Tis11B protein/butyrate response factor 1/EGF-response factor 1 |
| ydl012c | p51531 | SMARCA2 | Possible global transcription activator SNF2L2/BRM | yfr047c | q15274 | NADC | Nicotinate-nucleotide pyrophosphorylase [carboxylating]/quinolinate phosphoribosyl transferase |
| ydl012c | p20226 | TBP | TATA-binding protein/transcription initiation factor TFIID | yor355w | q14669 | TRIP12 | Thyroid receptor interacting protein 12/KIAA0045 |
| ydl012c | p51531 | SMARCA2 | Possible global transcription activator SNF2L2/BRM | yor355w | p42568 | MLLT3 | AF-9 protein |
| ydl013w | q07283 | THH | Trichohyalin | ydr510w | p55854 | SMT3H1 | Ubiquitin-like protein SMT3A |
| ydl013w | q07283 | THH | Trichohyalin | yer116c | p38398 | BRCA1 | BREAST CANCER, TYPE 1 |
| ydl017w | p24941 | CDK2 | Cell division protein kinase 2 | ycr050c | p49368 | CCT3 | T-complex protein 1, gamma subunit |
| ydl017w | p19784 | CSNK2A2 | Casein kinase II alpha' | ydl160c | p38919 | NUK-34 | Nuk__34 mRNA for translation initiation factor |
| ydl017w | p24941 | CDK2 | Cell division protein kinase 2 | ydl160c | q13838 | BAT1 | Probably ATP-dependent RNA helicase P47 |
| ydl017w | q00526 | CDK3 | Cell division protein kinase 3 | ydl160c | p04765 | EIF4A1 | Eukaryotic initiation factor 4AI |
| ydl017w | q00534 | CDK6 | Cell division protein kinase 6/PLSTIRE for serine/threonine protein kinase. | ydl160c | q14240 | EIF4A2 | Eukaryotic initiation factor 4AII |
| ydl017w | q00536 | PCTK1 | Serine/threonine protein kinase PCTAIRE-1 | ydl160c | p26196 | DDX6 | Probable ATP-dependent RNA helicase P54 |
| ydl017w | p24941 | CDK2 | Cell division protein kinase 2 | yjl088w | p00480 | OTC | Omithine carbamoylfransferase [precursor]/OTCase/ornithine transcarbamylase |
| ydl074c | p11055 | MYH3 | Embryonic myosin heavy chain. | ylr423c | q15431 | SYCP1 | Synaptonemal complex protein 1/SCP-1 protein |
| ydl074c | p12883 | MYH7 | Myosin heavy chain, cardiac muscle beta isoform | ylr423c | p12270 | TPR | Nucleoprotein TPR |
| ydl074c | p13533 | MYH6 | Myosin heavy chain, cardiac muscle alpha isoform | ylr423c | p30622 | RSN | Restin |
| ydl074c | p13535 | MYH8 | Myosin heavy chain, perinatal skeletal muscle | ylr423c | p05787 | KRT8 | Keratin, type II cytoskeletal 8/cytokeratin 8/K8/CK8 |
| ydl074c | p15924 | DSP | Desmoplakin I and II | ylr423c | p13535 | MYH8 | Myosin heavy chain, perinatal skeletal muscle |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ydl074c | p35580 | MYH10 | Myosin heavy chain, nonmuscle type B/cellular myosin heavy chain, type B/NMMHC-B | ylr423c | p11047 | LAMC1 | Laminin gamma-1 chain [precursor]/aminin B2 chain |
| ydl074c | p49454 | CENPF | CENP-F kinetochore protein | ylr423c | p15924 | DSP | Desmoplakin I and II |
| ydl074c | q02224 | CENPE | Centromeric protein E/CENP-E protein | ylr423c | p49454 | CENPF | CENP-F kinetochore protein |
| ydl074c | q03001 | BPAG1 | Bullous 230 kDa pemphigoid antigen 1 | ylr423c | q02224 | CENPE | Centromeric protein E/CENP-E protein |
| ydl090c | p49356 | FNTB | farnesyl-protein transferase beta-subunit | ykl019w | p49354 | FNTA | Protein farnesyltransferase alpha-subunit |
| ydl090c | p53609 | PGGT1B | Geranylgeranyltransferase type I beta-subunit | ykl019w | q92696 | RABGGTA | RAB geranylgeranyl transferase alpha subunit |
| ydl097c | q13098 | GPS1 | G protein pathway suppressor 1 | yel009c | p05412 | JUN | Transcription factor AP-1/c-jun proto oncogene |
| ydl113c | p15924 | DSP | Desmoplakin I and II | yjl036w | p35580 | MYH10 | Myosin heavy chain, nonmuscle type B/cellular myosin heavy chain, type B/NMMHC-B |
| ydl113c | q02224 | CENPE | Centromeric protein E/CENP-E protein | yjl036w | p49454 | CENPF | CENP-F kinetochore protein |
| ydl113c | p15924 | DSP | Desmoplakin I and II | ylr423c | p49454 | CENPF | CENP-F kinetochore protein |
| ydl113c | q02224 | CENPE | Centromeric protein E/CENP-E protein | ylr423c | q02224 | CENPE | Centromeric protein E/CENP-E protein |
| ydl150w | p05423 | BN51T | BN51 protein | ykr025w | p39687 | PHAP1 | HLA-DR associated protein I |
| ydl150w | p06748 | NPM1 | Nucleophosmin | ykr025w | o15355 | PPM1C | Protein phosphatase 2C gamma isoform/PP2C-GAMMA |
| ydl150w | p35663 | CYLC1 | Cyclin I | ykr025w | p46100 | ATRX | Transcriptional regulator ATRX/X-linked helicase II/X-linked nuclear protein |
| ydl150w | p46100 | ATRX | Transcriptional regulator ATRX/X-linked helicase II/X-linked nuclear protein | ykr025w | p21815 | IBSP | Bone sialoprotein II [precursor]/BSPII/Cell-binding sialoprotein |
| ydl150w | p55081 | MFAP1 | Microfibrillar protein 1 | ykr025w | p19338 | NCL | Nucleolin/protein C23 |
| ydl150w | q14093 | CYLC2 | Cylicin II | ykr025w | p17480 | UBTF | Nucleolar transcription factor 1/upstream binding factor 1/UBF-1 |
| ydl154w | p20585 | MSH3 | DNA mismatch repair protein MSH3 | ygl025c | q02817 | MUC2 | Intestinal mucin 2/mucin 2 |
| ydl154w | p43246 | MSH2 | DNA mismatch repair protein MSH2 | ygl025c | q02078 | MEF2A | Myocyte-specific enhancer factor 2A |
| ydl154w | p20585 | MSH3 | DNA mismatch repair protein MSH3 | yil144w | p49454 | CENPF | CENP-F kinetochore protein |
| ydl154w | p43246 | MSH2 | DNA mismatch repair protein MSH2 | yil144w | q02224 | CENPE | Centromeric protein E/CENP-E protein |
| ydl154w | p52701 | MSH6 | DNA mismatch repair protein MSH6/G/T mismatch binding protein | yil144w | p15924 | DSP | Desmoplakin I and II |
| ydl154w | p43246 | MSH2 | DNA mismatch repair protein MSH2 | Ymr224c | p49959 | MRE11A | Double-strand break repair protein MRE11A/MRE11 homolog |
| ydl155w | p14635 | CCNB1 | G2/mitotic-specific cyclin B1 | ybr135w | p10275 | AR | Androgen receptor |
| ydl203c | q14154 | KIAA0141 | Hypothetical protein KIAA0141 | ygr058w | p28676 | GCA | Grancalcin |
| ydl203c | q14154 | KIAA0141 | Hypothetical protein KIAA0141 | yor372c | p54259 | DRPLA | Atrophin-1/dentatorubral-pallidoluysian atrophy protein |
| ydl239c | p12883 | MYH7 | Myosin heavy chain, cardiac muscle beta isoform | ylr423c | q15431 | SYCP1 | Synaptonemal complex protein 1/SCP-1 protein |
| ydl239c | p13533 | MYH6 | Myosin heavy chain, cardiac muscle alpha isoform | ylr423c | p12270 | TPR | Nucleoprotein TPR |
| ydl239c | p15924 | DSP | Desmoplakin I and II | ylr423c | p13535 | MYH8 | Myosin heavy chain, perinatal skeletal muscle |
| ydl239c | p30622 | RSN | Restin | ylr423c | p05787 | KRT8 | Keratin, type II cytoskeletal 8/cytokeratin 8/K8/CK8 |
| ydl239c | p35580 | MYH10 | Myosin heavy chain, nonmuscle type B/cellular myosin heavy chain, type B/NMMHC-B | ylr423c | p11047 | LAMC1 | Laminin gamma-1 chain [precursor]/aminin B2 chain |
| ydl239c | p49454 | CENPF | CENP-F kinetochore protein | ylr423c | p15924 | DSP | Desmoplakin I and II |
| ydl239c | q02224 | CENPE | Centromeric protein E/CENP-E protein | ylr423c | p49454 | CENPF | CENP-F kinetochore protein |
| ydl239c | q03001 | BPAG1 | Bullous 230 kDa pemphigoid antigen 1 | ylr423c | q02224 | CENPE | Centromeric protein E/CENP-E protein |
| ydl239c | q08378 | GOLGA3 | Golgin-160 | ylr423c | p30622 | RSN | Restin |
| ydl239c | p13533 | MYH6 | Myosin heavy chain, cardiac muscle alpha isoform | yol091w | q15431 | SYCP1 | Synaptonemal complex protein 1/SCP-1 protein |
| ydl239c | p15924 | DSP | Desmoplakin I and II | yol091w | p12270 | TPR | Nucleoprotein TPR |
| ydl239c | p49454 | CENPF | CENP-F kinetochore protein | yol091w | p42566 | EPS15 | Epidermal growth factor receptor substrate 15 |
| ydl239c | q02224 | CENPE | Centromeric protein E/CENP-E protein | yol091w | p49454 | CENPF | CENP-F kinetochore protein |
| ydl239c | q03001 | BPAG1 | Bullous 230 kDa pemphigoid antigen 1 | yol091w | q02224 | CENPE | Centromeric protein E/CENP-E protein |
| ydl239c | q08378 | GOLGA3 | Golgin-160 | yol091w | p35579 | MYH9 | Myosin heavy chain, nonmuscle type A/cellular myosin heavy chain, type A/NMMHC-A |
| ydl246c | p11766 | ADH5 | Class III alcohol dehydrogenase chi subunit | ydl246c | p11766 | ADH5 | Class III alcohol dehydrogenase chi subunit |
| ydl246c | q00796 | SORD | Sorbitol dehydrogenase/L-iditol-2 dehydrogenase | ydl246c | q00796 | SORD | Sorbitol dehydrogenase/L-iditol-2 dehydrogenase |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ydl246c | p11766 | ADH5 | Class III alcohol dehydrogenase chi subunit | yjr159w | p11766 | ADH5 | Class III alcohol dehydrogenase chi subunit |
| ydl246c | q00796 | SORD | Sorbitol dehydrogenase/L-iditol-2 dehydrogenase | yjr159w | q00796 | SORD | Sorbitol dehydrogenase/L-iditol-2 dehydrogenase |
| ydr002w | p07197 | NEFM | Neurofilament triplet M protein/160 Kd neurofilament protein/NF-M | ykr048c | p21817 | RYR1 | Ryanodine receptor 1 |
| ydr002w | p12036 | NEFH | Neurofilament triplet H proprotein/200 Kd neurofilament protein | ykr048c | q01105 | SET | Set protein/HLA-DR associated protein II/PHAPII |
| ydr002w | p35663 | CYLC1 | Cyclin I | ykr048c | p55209 | NAP1L1 | NAP-1/nucleosome assembly protein 1-like 1 |
| ydr002w | p43487 | RANBP1 | RAN specific GTPase-activating protein/RanBP1 | ykr048c | p46060 | RANGAP1 | RanGTPase activating protein 1 |
| ydr002w | p46821 | MAP1B | Microtubule-associated protein 1B | ykr048c | q99457 | NAP1L3 | Nucleosome assembly protein 1-like3 |
| ydr002w | p49792 | RANBP2 | Nuclear pore complex protein NUP358/nucleoporin NUP358 | ykr048c | q99733 | NAP1L4 | Nucleosome assembly protein 2/nucleosome assembly protein 1-like 4 |
| ydr002w | q92794 | MOZ | Monocytic leukemia zinc finger protein | ykr048c | q01534 | TSPY | Homo sapiens testicular protein (TSPY) mRNA, complete cds. |
| ydr061w | p21439 | MDR3 | Membrane glycoprotein P | ycr086w | p39880 | CUTL1 | CCAAT displacement protein/CDP |
| ydr077w | q02817 | MUC2 | Intestinal mucin 2/mucin 2 | ydr044w | p36551 | CPO | Coproporphytinogen III oxidase/coprogen oxidase |
| ydr099w | p42655 | YWHAE | 14-3-3 protein epsilon | ybl043w | q06481 | APLP2 | Amyloid-like protein 2/APPH/amyloid protein homolog |
| ydr099w | p42655 | YWHAE | 14-3-3 protein epsilon | ynl042w | p54259 | DRPLA | Atrophin-1/dentatorubral-pallidoluysian atrophy protein |
| ydr128w | o00628 | PTS2R | Peroxisomal targeting signal 2 receptor | ylr208w | q09028 | RBAP48 | Chromatin assembly factor 1 P48 subunit/retinoblastoma binding protein P48 |
| ydr128w | p35606 | COPP | Beta subunit of coatomer complex | ylr208w | p25388 | GNB2-RS1 | Guanine nucleotide-binding protein beta subunit-like protein 12.3 |
| ydr128w | q09028 | RBAP48 | Chromatin assembly factor 1 P48 subunit/retinoblastoma binding protein P48 | ylr208w | q16576 | RBBP7 | Histone acetyl transferase type B subunit 2/retinoblastoma-binding protein |
| ydr128w | q16576 | RBBP7 | Histone acetyl transferase type B subunit 2/retinoblastoma-binding protein | ylr208w | p43034 | PAFAH1B1 | Platelet-activating factor acetyl-hydrolase IB alpha subunit |
| ydr142c | p25388 | GNB2-RS1 | Guanine nucleotide-binding protein beta subunit-like protein 12.3 | yil160c | p55084 | HADHB | Trifunctional enzyme beta subunit, mitochondrial [precursor] |
| ydr142c | q09028 | RBAP48 | Chromatin assembly factor 1 P48 subunit/retinoblastoma binding protein P48 | yil160c | p24752 | AMLAD | ALPHA-METHYLACETOACETIC-ACIDURIA |
| ydr142c | q13216 | CKN1 | Cockayne syndrome WD-repeat protein CSA | yil160c | p42765 | THIM | 3-ketoacyl-CoA thiolase mitochondrial/mitochondrial 3-oxoacyl-CoA thiolase |
| ydr142c | q13610 | PWP1 | Periodic tryptophan protein 1 homolog/keratinocyte protein IEF SSP 9502 | yil160c | p22307 | SCP2 | Nonspecific lipid-transfer protein/sterol carrier protein X/sterol carrier protein 2 |
| ydr142c | q16576 | RBBP7 | Histone acetyl transferase type B subunit 2/retinoblastoma-binding protein | yil160c | p09110 | ACAA | 3-ketoacyl-CoA thiolase, peroxisomal/3-oxoacyl-CoA peroxisomal thiolase. |
| ydr148c | p10515 | DLAT | Dihydrolipoamide acetyltransferase component of pyruvate dehydrogenase complex/PDC-E2 | ydr510w | q93068 | SMT3H3 | Ubiquitin-like protein SMT3C |
| ydr148c | p11182 | DBT | Lipoamide acyl transferase component of branched-chain alpha-keto acid dehydrogenase complex | ydr510w | p55855 | SMT3H2 | Ubiquitin-like protein SMT3B |
| ydr148c | p17677 | GAP43 | Neuromodulin/axonal membrane protein GAP-43 | ydr510w | p55854 | SMT3H1 | Ubiquitin-like protein SMT3A |
| ydr200c | p13533 | MYHB | Myosin heavy chain, cardiac muscle alpha isoform | Ymr052w | p30622 | RSN | Restin |
| ydr200c | p49454 | CENPF | CENP-F kinetochore protein | Ymr052w | p35580 | MYH10 | Myosin heavy chain, nonmuscle type B/cellular myosin heavy chain, type B/NMMHC-B |
| ydr200c | p49454 | CENPF | CENP-F kinetochore protein | ynl127w | p20309 | CHRM3 | Muscarinic acetylcholine receptor M3 |
| ydr201w | p12270 | TPR | Nucleoprotein TPR | yil144w | p49454 | CENPF | CENP-F kinetochore protein |
| ydr201w | p30622 | RSN | Restin | yil144w | q02224 | CENPE | Centromeric protein E/CENP-E protein |
| ydr218c | p43236 | PNUTL2 | Peanut-like protein 2/Brain protein H5 | yjr076c | q14141 | KIAA0128 | Septin 2 homolog [fragment] |
| ydr218c | q14141 | KIAA0128 | Septin 2 homolog [fragment] | yjr076c | q15019 | NEDD5 | NEDD5 protein homolog/KIAA0158 |
| ydr218c | q15019 | NEDD5 | NEDD5 protein homolog/KIAA0158 | yjr076c | q16643 | DBN1 | Drebin E |
| ydr218c | q16181 | CDC10 | CDC10 protein homolog | yjr076c | q16181 | CDC10 | CDC10 protein homolog |
| ydr225w | p02261 | H2AFA | Histone H2A.1 | ykr048c | p46060 | RANGAP1 | RanGTPase activating protein 1 |
| ydr225w | p04908 | none | Histone H2A.5 | ykr048c | q99457 | NAP1L3 | Nucleosome assembly protein 1-like3 |
| ydr225w | p16104 | H2AX | Histone H2A.X | ykr048c | q99733 | NAP1L4 | Nucleosome assembly protein 2/nucleosome assembly protein 1-like 4 |
| ydr225w | p28001 | H2AFO | Histone H2A.2/H2A/O | ykr048c | p55209 | NAP1L1 | NAP-1/nucleosome assembly protein 1-like 1 |
| ydr228c | p20226 | TBP | TATA-binding protein/transcription initiation factor TFIID | ylr423c | p49454 | CENPF | CENP-F kinetochore protein |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ydr228c | p54252 | MJD1 | Machado-joseph disease protein 1 | ylr423c | q02224 | CENPE | Centromeric protein E/CENP-E protein |
| ydr228c | q10571 | MN1 | Probable tumor suppressor protein MN1 | ylr423c | p13535 | MYH8 | Myosin heavy chain, perinatal skeletal muscle |
| ydr228c | q93074 | KIAA0192 | Hypothetical protein KIAA0192 | ylr423c | p15924 | DSP | Desmoplakin I and II |
| ydr259c | p11055 | MYH3 | Embryonic myosin heavy chain. | ylr423c | p15924 | DSP | Desmoplakin I and II |
| ydr259c | p15924 | DSP | Desmoplakin I and II | ylr423c | p49454 | CENPF | CENP-F kinetochore protein |
| ydr259c | p49454 | CENPF | CENP-F kinetochore protein | ylr423c | q02224 | CENPE | Centromeric protein E/CENP-E protein |
| ydr308c | p24928 | POLR2A | DNA-directed RNA polymerase II largest subunit. | yor174w | p49321 | NASP | Nuclear autoantigenic sperm protein |
| ydr308c | q03001 | BPAG1 | Bullous 230 kDa pemphigoid antigen 1 | yor174w | p35580 | MYH10 | Myosin heavy chain, nonmuscle type B/ cellular myosin heavy chain, type B/ NMMHC-B |
| ydr311w | p32780 | BTF2 | Basic transcription factor 62 kD subunit | ygr120c | p04114 | APOB | Apolipoprotein B |
| ydr311w | p32780 | BTF2 | Basic transcription factor 62 kD subunit | ylr423c | q02224 | CENPE | Centromeric protein E/CENP-E protein |
| ydr328c | p07199 | CENP-B | Major centromere autoantigen B/ centromere protein B | yfl009w | p35606 | COPP | Beta subunit of coatomer complex |
| ydr328c | p17480 | UBTF | Nucleolar transcription factor 1/ upstream binding factor 1/UBF-1 | yfl009w | q15542 | TAF2D | Transcription initiation factor TFIID 100 Kd subunit/TAFII-100/TAFII100 |
| ydr328c | p19338 | NCL | Nucleolin/protein C23 | yfl009w | p04901 | GNB1 | Guanine nucleotide-binding protein G(I)/G(S)/G(T) beta subunit 1 |
| ydr328c | p34991 | TCEB1L | Cyclin A/CDK2-associated p19 | yfl009w | p43034 | PAFAH1B1 | Platelet-activating factoracetylhydrolase IB alpha subunit |
| ydr376w | p22570 | FDXR | NADPH:adrenodoxin oxidoreductase [precursor]/adrenodoxin reductase/ ferredosin-NADP+reductase | ycr093w | p54252 | MJD1 | Machado-joseph disease protein 1 |
| ydr376w | p22570 | FDXR | NADPH:adrenodoxin oxidoreductase [precursor]/adrenodoxin reductase/ ferredosin-NADP+reductase | ylr024c | p49321 | NASP | Nuclear autoantigenic sperm protein |
| ydr388w | p14317 | HCLS1 | Hematopoietic lineage cell specific protein | ycr009c | p15924 | DSP | Desmoplakin I and II |
| ydr388w | p49418 | AMPH | Amphiphysin | ycr009c | p49418 | AMPH | Amphiphysin |
| ydr394w | p17980 | PSMC3 | 26S protease regulatory subunit 6A/ TAT-binding protein 1/TBP-1 | ygr232w | q06547 | E4TF1B | GA binding protein beta-1 chain |
| ydr394w | p35998 | PSMC2 | 26S protease regulatory subunit 7/MSS1 protein | ygr232w | q01485 | ANK2 | Brain ankyrin variant 2 |
| ydr394w | p43686 | PSMC4 | 26S protease regulatory subunit 6B/ TAT-binding protein-7ITBP-7 | ygr232w | p53355 | DAPK1 | Death-associated protein kinase 1/DAP-kinase 1 |
| ydr394w | p47210 | PSMC5 | 26S proteasome regulatory subunit 8/ proteasome subunit p45 | ygr232w | p20749 | BCL3 | B-cell lymphoma 3-encoded protein |
| ydr394w | q03527 | PSMC1 | 26S protease (54) regulatory subunit | ygr232w | q01484 | ANK2 | Ankyrin, brain variant 1/ankyrin B |
| ydr394w | q92524 | PSMC6 | 26S protease regulatory subunit S10B/ proteasome subunit P42 | ygr232w | p42773 | CDN2C | Cyclin dependent kinase 6 inhibitor |
| ydr408c | p22102 | GART | Trifunctional purine biosynthetic protein adenosine-3 | ycr063w | p41223 | EDG2 | G10 protein homolog |
| ydr408c | p22102 | GART | Trifunctional purine biosynthetic protein adenosine-3 | yor174w | p35580 | MYH10 | Myosin heavy chain, nonmuscle type B/ cellular myosin heavy chain, type B/ NMMHC-B |
| ydr416w | q14690 | KIAA0185 | RRP5 protein homolog/KIAA0185 [fragment] | ygr129w | q02224 | CENPE | Centromeric protein E/CENP-E protein |
| ydr429c | p33240 | CSTF2 | Cleavage stimulation factor, 64 kD sub-unit | yfl017c | p08578 | SNRPE | Small nuclear ribonucleoprotein E/ snRNP-E |
| ydr439w | p13535 | MYH8 | Myosin heavy chain, perinatal skeletal muscle | ycr086w | p39880 | CUTL1 | CCAAT displacement protein/CDP |
| ydr477w | p54646 | PRKAA2 | 5'-AMP-activated protein kinase, catalytic alpha-2 chain | yer027c | p10451 | SPP1 | Osteopontin [precursor] |
| ydr482c | p42566 | EPS15 | Epidermal growth factor receptor substrate 15 | ygl028c | q02505 | MUC3 | Mucin 3 [fragments]/intestinal mucin 3 |
| ydr482c | q02224 | CENPE | Centromeric protein E/CENP-E protein | ygl028c | q02817 | MUC2 | Intestinal mucin 2/mucin 2 |
| ydr490c | p17612 | PRKACA | CAMP-dependent protein kinase catalytic subunit type alpha | ylr466w | q02505 | MUC3 | Mucin 3 [fragments]/intestinal mucin 3 |
| yer018c | p02546 | LMN1 | Lamin C | yhr193c | p50502 | HIP | Progesterone receptor-associated p48 protein |
| yer018c | p02545 | LMN1 | Lamin A/70 KD Lamin | Ymr117c | p30622 | RSN | Restin |
| yer018c | p02546 | LMN1 | Lamin C | Ymr117c | p49454 | CENPF | CENP-F kinetochore protein |
| yer018c | p35749 | MYH11 | Myosin heavy chain, smooth muscle isoform/SMMHC [FRAGMENT] | Ymr117c | p35580 | MYH10 | Myosin heavy chain, nonmuscle type B/ cellular myosin heavy chain, type B/ NMMHC-B |
| yer018c | q07283 | THH | Trichohyalin | Ymr117c | p11055 | MYH3 | Embryonic myosin heavy chain. |
| yer018c | q93074 | KIAA0192 | Hypothetical protein KIAA0192 | Ymr117c | p42566 | EPS15 | Epidermal growth factor receptor substrate 15 |
| yer023w | p32322 | PYCR1 | Pyrroline 5-carboxylate reductase | yer023w | p32322 | PYCR1 | Pyrroline 5-carboxylate reductase |
| yer082c | p11016 | GNB2 | Guanine nucleotide-binding protein beta subunit 2 | ykl142w | p07942 | LAMB1 | Laminin beta-1 chain/Laminin B1 chain |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yer102w | p09058 | RPS8 | 40S ribosomal protein S8 | ybr135w | p10275 | AR | Androgen receptor |
| yer102w | p09058 | RPS8 | 40S ribosomal protein S8 | yfl017c | p08578 | SNRPE | Small nuclear ribonucleoprotein E/snRNP-E |
| yer106w | q13416 | ORC2L | Origin recognition complex subunit 2 | ycr086w | p39880 | CUTL1 | CCAAT displacement protein/CDP |
| yer127w | p30622 | RSN | Restin | ydr299w | p19338 | NCL | Nucleolin/protein C23 |
| yer127w | p35663 | CYLC1 | Cyclin I | ydr299w | p46060 | RANGAP1 | RanGTPase activating protein 1 |
| yer127w | p35749 | MYH11 | Myosin heavy chain, smooth muscle isoform/SMMHC [FRAGMENT] | ydr299w | p07197 | NEFM | Neurofilament triplet M protein/160 Kd neurofilament protein/NF-M |
| yer127w | p46100 | ATRX | Transcriptional regulator ATRX/X-linked helicase II/X-linked nuclear protein | ydr299w | p21817 | RYR1 | Ryanodine receptor 1 |
| yer127w | q01484 | ANK2 | Ankyrin, brain variant 1/ankyrin B | ydr299w | p46100 | ATRX | Transcriptional regulator ATRX/X-linked helicase II/X-linked nuclear protein |
| yer131w | q06722 | RPS26 | Ribosomal protein S26 | ylr435w | p27797 | CALR | Calreticulin/52kD ribonuclecprotein autoantigen RO/SS-A |
| yer133w | p05323 | PPP2CA | Serine/threonine protein phosphatase PP2A-alpha, catalytic subunit | ynl233w | p35251 | RFC1 | Replication factor C large subunit/activator 1140 Kd subunit |
| yer133w | p08129 | PPP1CA | Serine/threonine protein phosphatase PP1-alpha 1 catalytic subunit | ynl233w | p35663 | CYLC1 | Cyclin I |
| yer133w | p11082 | PPP2CB | Serine/threonine protein phosphatase PP2A-beta, catalytic subunit | ynl233w | p51825 | MLLT2 | AF-4 protein |
| yer133w | p36873 | PPP1CC | Serine/threonine-protein phosphatase PP1-gamma catalytic subunit | ynl233w | p46821 | MAP1B | Microtubule-associated protein 1B |
| yer133w | p37140 | PPP1CB | Serine/threonine-protein phosphatase PP1-beta catalytic subunit | ynl233w | p35659 | DEK | Dek protein |
| yer144c | o00507 | FAF-Y | Probable ubiquitin carboxyl-terminal hydrolase FAF-Y | ybr059c | q16816 | PHKG1 | Phosphorylase B kinase gamma catalytic chain, skeletal muscle isoform |
| yer144c | p45974 | USP5 | Ubiquitin carboxyl-terminal hydrolase 5/isopeptidase T | ybr059c | p51956 | NEK3 | Serine/threonine-protein kinase NEK3 [fragment] |
| yer144c | p51784 | USP11 | Ubiquitin C-terminal hydrolase 11 | ybr059c | p49137 | MAPKAPK-2 | Map kinase-activated protein kinase 2 |
| yer144c | p54578 | USP14 | Queuine tRNA-ribosyl transferase/tRNA-guanine transglycosylase | ybr059c | p51955 | NEK2 | Serine/threonine-protein kinase NEK2 |
| yer144c | q02817 | MUC2 | Intestinal mucin 2/mucin 2 | ybr059c | p15735 | PHKG2 | Phosphorylase kinase, testis/liver, gamma-2 |
| yer144c | q92995 | USP13 | Ubiquitin carboxyl-terminal hydrolase 13/isopeptidase T-3 | ybr059c | q13177 | PAK2 | Serine/threonine-protein kinase PAK-gamma |
| yer144c | q93008 | USP9X | Probable ubiquitin carboxyl-terminal hydrolase FAF-X | ybr059c | p27448 | P78 | Putative serind/threonine-protein kinase P78 |
| yer144c | q93009 | USP7 | Ubiquitin carboxyl-terminal hydrolase 7/herpesvirus associated ubiquitin-specific protease | ybr059c | p51957 | STK2 | Serine/threonine-protein kinase NRK2 |
| yer179w | q06609 | RAD51 | DNA repair protein RAD51 | yer179w | q06609 | RAD51 | DNA repair protein RAD51 |
| yer179w | q14565 | DMC1 | Meiotic recombination protein DMC1/LIM15 homolog | yer179w | q14565 | DMC1 | Meiotic recombination protein DMC1/LIM15 homolog |
| yfl010c | p02812 | PRB2 | Salivary proline-rich protein/Clone CP7 | ygr136w | p29354 | GRB2 | Growth factor receptor-bound protein 2 |
| yfl010c | p04280 | PRB1 | Salivary proline-rich protein/clone CP3, CP4, and CP5 | ygr136w | p06241 | FYN | Proto-oncogene tyrosine-protein kinase FYN/SYN |
| yfl010c | p10161 | PRB4 | Salivary proline-rich protein PO [fragment]/allele M | ygr136w | p14317 | HCLS1 | Hematopoietic lineage cell specific protein |
| yfl010c | p10162 | PRB4 | Salivary proline-rich protein PO [fragment]/allelle K | ygr136w | p19878 | NCF2 | Neutrophil cytosol factor 2/NCF-2/neutrophil NADPH oxidase factorde 2/P67-PHOX |
| yfl010c | p17600 | SYN1 | Synapsin l/brain protein 4.1 | ygr136w | q92794 | MOZ | Monocytic leukemia zinc finger protein |
| yfl010c | p22670 | RFX1 | MHC class regulatory factor RFX1 | ygr136w | q15811 | ITSN | Intersectin/SH3 domain-containing protein SH3P17 |
| yfl010c | p23246 | PSF | PTB-associated splicing factor | ygr136w | p16333 | NCK | Cytoplasmic protein NCK |
| yfl010c | p35637 | FUS | RNA-binding protein FUS/TLS | ygr136w | p46108 | CRK | Proto-oncogene C-CRK |
| yfl010c | q92793 | CREBBP | CREB-BINDING PROTEIN | ygr136w | p07947 | YES1 | Proto-oncogene tyrosine-protein kinase YES/C-YES |
| yfl010c | q92794 | MOZ | Monocytic leukemia zinc finger protein | ygr136w | p15498 | VAV | Vav proto-oncogene |
| yfl010c | q99217 | AIH1 | AMELOGENESIS IMPERFECTA 1, HYPOPLASTIC TYPE | ygr136w | p46109 | CRKL | Crk-like protein |
| yfl010c | p02812 | PRB2 | Salivary proline-rich protein/Clone CP7 | yor197w | p02812 | PRB2 | Salivary proline-rich protein/Clone CP7 |
| yfl010c | p04280 | PRB1 | Salivary proline-rich protein/clone CP3, CP4, and CP5 | yor197w | p04280 | PRB1 | Salivary proline-rich protein/clone CP3, CP4, and CP5 |
| yfl010c | p10161 | PRB4 | Salivary proline-rich protein PO [fragment]/allele M | yor197w | p54253 | SCA1 | Ataxin-1/Spinocerebellar ataxia type 1 protein |
| yfl010c | p22670 | RFX1 | MHC class II regulatory factor RFX1 | yor197w | q09472 | EP300 | E1A-associated protein P300 |
| yfl010c | p23246 | PSF | PTB-associated splicing factor | yor197w | q93074 | KIAA0192 | Hypothetical protein KIAA0192 |
| yfl010c | p35637 | FUS | RNA-binding protein FUS/TLS | yor197w | p42858 | HD | Huntingtin/huntington's disease protein |
| yfl010c | q99217 | AIH1 | AMELOGENESIS IMPERFECTA 1, HYPOPLASTIC TYPE | yor197w | q01844 | EWSR1 | RNA-binding protein EWS |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yfl023w | q02224 | CENPE | Centromeric protein E/CENP-E protein | ybr154c | p19388 | POLR2E | DNA-directed RNA polymerase II 23 kD polypeptide/RPB25/XAP4 |
| yfl023w | p35580 | MYH10 | Myosin heavy chain, nonmuscle type B/ cellular myosin heavy chain, type B/ NMMHC-B | ylr200w | p49454 | CENPF | CENP-F kinetochore protein |
| yfl023w | p46100 | ATRX | Transcriptional regulator ATRX/X-linked helicase II/X-linked nuclear protein | ylr200w | q08379 | GOLGA2 | Golgin-95 |
| yfl023w | p48681 | NES | Nestin | ylr200w | p42566 | EPS15 | Epidermal growth factor receptor substrate 15 |
| yfl023w | q02224 | CENPE | Centromeric protein E/CENP-E protein | ylr200w | q02224 | CENPE | Centromeric protein E/CENP-E protein |
| yfr024c-a | p14317 | HCLS1 | Hematopoietic lineage cell specific protein | ybl007c | q99102 | MUC4 | Tracheo-bronchial mucin 4/mucin 4 [fragment] |
| yfr024c-a | p16333 | NCK | Cytoplasmic protein NCK | ybl007c | p16333 | NCK | Cytoplasmic protein NCK |
| yfr024c-a | p29354 | GRB2 | Growth factor receptor-bound protein 2 | ybl007c | p29354 | GRB2 | Growth factor receptor-bound protein 2 |
| yfr024c-a | p41240 | CSK | Tryrosine-protein kinase CSK | ybl007c | p06241 | FYN | Proto-oncogene tyrosine-protein kinase FYN/SYN |
| yfr024c-a | p46109 | CRKL | Crk-like protein | ybl007c | p09769 | M19722 | Human fgr proto-oncogene encoded p55-c-fgr protein complete cds. |
| yfr024c-a | p98171 | RGC1 | RHO-GAP hematopoietic protein C1 | ybl007c | q15811 | ITSN | Intersectin/SH3 domain-containing protein SH3P17 |
| yfr024c-a | q13813 | SPTA2 | Spectrin alpha chain, brain/nonerythroid alpha-spectrin | yb007c | p07947 | YES1 | Proto-oncogene tyrosine-protein kinase YES/C-YES |
| yfr024c-a | q15811 | ITSN | Intersectin/SH3 domain-containing protein SH3P17 | ybl007c | q14687 | KIAA0182 | Hypothetical protein KIAA0182 |
| yfr024c-a | p46109 | CRKL | Crk-like protein | ygr268c | q92794 | MOZ | Monocytic leukemia zinc finger protein |
| yfr047c | q15274 | NADC | Nicotinate-nucleotide pyro-phosphorylase [carboxylating]/quinolinate phosphoribosyl/transferase | yfr047c | q15274 | NADC | Nicotinate-nucleotide pyro-phosphorylase [carboxylating]/quinolinate phosphoribosyl transferase |
| ygl058w | p23567 | UBE2B | Ubiquitin-conjugating enzyme E2-17 kD | ycr066w | q00755 | PML | Probable transcription factor PML |
| ygl058w | p47986 | UBE2D3 | Ubiquitin-conjugating enzyme E2-17 kD 3 | ycr066w | p35227 | MEL18 | DNA-binding protein MEL-18/Zinc finger protein 144 |
| ygl058w | p49459 | UBE2A | Ubiquitin-conjugating enzyme E2-17 kD/HR6A | ycr066w | p15918 | RAG1 | V(D)J recombination activating protein 1 |
| ygl058w | p50550 | UBE2I | Ubiquitin conjugating enzyme E2-18 kD | ycr066w | o15541 | ZNF183 | zinc finger protein 183 |
| ygl058w | p51668 | UBE2D1 | Ubiquitin conjugating enzyme E2-17 kD | ycr066w | p35226 | BMI1 | DNA-binding protein BMI1 |
| ygl058w | p51669 | UBE2D2 | Ubiquitin conjugating enzyme E2-17 kD 2 | ycr066w | p38398 | BRCA1 | BREAST CANCER, TYPE 1 |
| ygl058w | p51965 | UBE2E1 | Ubiquitin conjugating enzyme E2-21 kD UBCH6 | ycr066w | p29591 | PML | Probable transcription factor PML |
| ygl058w | p56554 | UBE2G2 | Ubiquitin-conjugating enzyme E2 G2 | ycr066w | p29592 | PML | Probable transcription factor PML |
| ygl058w | q16781 | UBE2N | Ubiquitin conjugating enzyme E2-17 kD | ycr066w | p29590 | PML | Probable transcription factor PML |
| ygl058w | q99462 | UBE2G1 | Ubiquitin-conjugating enzyme E2 G1 | ycr066w | p29593 | PML | Probable transcription factor PML |
| ygl112c | p49848 | TAF2E | Transcription initiation factor TFIID 70 kD subunit/TAFII-70 | Ymr236w | q16594 | TAF2G | Transcription initiation factor TFIID 31 kD subunit |
| ygl112c | p49848 | TAF2E | Transcription initiation factor TFIID 70 kD subunit/TAFII-70 | Ymr255w | p51825 | MLLT2 | AF-4 protein |
| ygl115w | p54619 | PRKAG1 | 5'-AMP-activated protein kinase, gamma-1 subunit | yer027c | p10451 | SPP1 | Osteopontin [precursor] |
| ygl122c | p42858 | HD | Huntingtin/huntington's disease protein | ykr026c | q14232 | ELF2B1 | Translation initiation factor eIF-2B alpha subunit |
| ygl122c | q14814 | MEF2D | Myocyte-specific enhancer factor 2D | ykr026c | p49770 | EIF2B2 | Translation initiation factor EIF-2B beta subunit/S20iii15 |
| ygl150c | o14647 | CHD2 | Chromodomain-helicase-DNA-binding protein 2/CHD-2 | ydl002c | p17480 | UBTF | Nucleolar transcription factor 1/upstream binding factor |
| ygl150c | p19338 | NCL | Nucleolin/protein C23 | ydl002c | p36402 | TCF7 | T-cell-specific transcription factor 1/TCF-1 |
| ygl150c | p28370 | SMARCA1 | Possible global transcription activator SNF2L1 | ydl002c | q00059 | TCF6L1 | Mitochondrial transcription factor 1 |
| ygl150c | p46100 | ATRX | Transcriptional regulator ATRX/X-linked helicase II/X-linked nuclear protein | ydl002c | p26583 | HMG2 | High mobility group protein HMG2/HMG-2 |
| ygl150c | p51531 | SMARCA2 | Possible global transcription activator SNF2L2/BRM | ydl002c | q06945 | SOX4 | Transcription factor SOX-4 |
| ygl150c | p51532 | SMARCA4 | Possible global transcription activator SNF2L4/BRG-1 protein | ydl002c | q08945 | SSRP1 | Structure-specific recognition protein 1 |
| ygl150c | q03468 | CSB | Excision repair protein ERCC-6/cockayne syndrome protein CSB | ydl002c | p09429 | HMG1 | High mobility group-1 protein |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ygl150c | p46100 | ATRX | Transcriptional regulator ATRX/X-linked helicase II/X-linked nuclear protein | yor355w | q14669 | TRIP12 | Thyroid receptor interacting protein 12/KIAA0045 |
| ygl150c | q03468 | CSB | Excision repair protein ERCC-6/cockayne syndrome protein CSB | yor355w | p42568 | MLLT3 | AF-9 protein |
| ygl155w | p49356 | FNTB | farnesyl-protein transferase beta-subunit | ykl019w | p49354 | FNTA | Protein farnesyltransferase alpha-subunit |
| ygl155w | p53609 | PGGT1B | Geranylgeranyltransferase type I beta-subunit | ykl019w | q92696 | RABGGTA | RAB geranylgeranyl transferase alpha subunit |
| ygl158w | p15735 | PHKG2 | Phosphorylase kinase, testis/liver, gamma-2 | ylr113w | p53779 | MAPK10 | Mitogen-activated protein kinase 10 |
| ygl158w | p27448 | P78 | Putative serind/threonine-protein kinase P78 | ylr113w | p53778 | MAPK12 | Mitogen-activated protein kinase 12/ERK6/extracellular signal-regulated kinase 6 |
| ygl158w | p49137 | MAPKAPK-2 | Map kinase-activated protein kinase 2 | ylr113w | p27361 | MAPK3 | Mitogen-activated protein kinase 3/extracellular signal-regulated kinase 1 |
| ygl158w | p51812 | RPS6KA3 | Ribosomal protein S6 kinase II alpha 3/insulin-stimulated protein kinase 1 | ylr113w | q15759 | MAPK11 | Mitogen-activated protein kinase 11 |
| ygl158w | p53355 | DAPK1 | Death-associated protein kinase 1/DAP-kinase 1 | ylr113w | p28482 | MAPK1 | Mitogen-activated protein kinase 1/extracellular signal-regulated kinase 2 |
| ygl158w | q14012 | CAMK1 | Calcium/calmodulin-dependent protein kinase type I | ylr113w | q16539 | MAPK14 | Mitogen-activated protein kinase 14/CSBP |
| ygl158w | q16566 | CAMK4 | calcium/calmodulin-dependent protein kinase IV | ylr113w | q13164 | MAPK7 | Mitogen-activated protein kinase 7/ERK5 |
| ygl158w | q16816 | PHKG1 | Phosphorylase B kinase gamma catalytic chain, skeletal muscle isoform | ylr113w | p45984 | MAPK9 | Mitogen activated protein kinase 9 |
| ygl189c | q06722 | RPS26 | Ribosomal protein S26 | ylr435w | p27797 | CALR | Calreticulin/52kD ribonucleoprotein autoantigen RO/SS-A |
| ygl192w | p04062 | GBA | Glucosylceramidase | ybr057c | p49454 | CENPF | CENP-F kinetochore protein |
| ygl237c | p23511 | NFYA | CAAT-box DNA binding protein subunit B | ybl021c | p25208 | NFYB | CCAAT-binding Transcription factor subunit A/CAAT-box DNA binding protein subunit B |
| ygl237c | p54259 | DRPLA | Atrophin-1/dentatorubral-pallidoluysian atrophy protein | ybl021c | q01658 | DR1 | TATA binding protein-associated phosphoprotein |
| ygl242c | p20749 | BCL3 | B-cell lymphoma 3-encoded protein | ykr099w | p10244 | MYBL2 | Myb-related protein B/B-myb |
| ygl242c | p53355 | DAPK1 | Death-associated protein kinase 1/DAP-kinase 1 | ykr099w | p10242 | MYB | MYB proto-oncogene protein |
| ygl242c | q01484 | ANK2 | Ankyrin, brain variant 1/ankyrin B | ykr099w | p25054 | APC | Adenomatous polyposis coli protein |
| ygl242c | q01485 | ANK2 | Brain ankyrin variant 2 | ykr099w | p10243 | MYBL1 | Myb-related protein A/A-myb |
| ygl254w | p08151 | GLI1 | GLI protein/zinc finger protein GLI1 | ygr047c | p19338 | NCL | Nucleolin/protein C23 |
| ygl254w | p41182 | BCL6 | B-cell lymphoma 6 protein/zinc finger protein 51 | ygr047c | p51531 | SMARCA2 | Possible global transcription activator SNF2L2/BRM |
| ygl254w | p41182 | BCL6 | B-cell lymphoma 6 protein/zinc finger protein 51 | yor039w | p13862 | CSNK2B | Casein kinase II beta subunit |
| ygr010w | q92764 | KRTHA5 | Keratin, type I cuticular HA5/hair keratin, type I HA5 | ygr010w | q92764 | KRTHA5 | Keratin, type 1 cuticular HA5/hair keratin, type I HA5 |
| ygr014w | p35658 | NUP214 | Nuclear pore complex protein NUP214/CAN protein | yil144w | p15924 | DSP | Desmoplakin I and II |
| ygr014w | q02817 | MUC2 | Intestinal mucin 2/mucin 2 | yil144w | q02224 | CENPE | Centromeric protein E/CENP-E protein |
| ygr014w | q14157 | KIAA0144 | Hypothetical protein KIAA0144 | yil144w | p13533 | MYH6 | Myosin heavy chain, cardiac muscle alpha isoform |
| ygr014w | q99102 | MUC4 | Tracheo-bronchial mucin 4/mucin 4 [fragment] | yil144w | p49454 | CENPF | CENP-F kinetochore protein |
| ygr017w | p17480 | UBTF | Nucleolar transcription factor 1/upstream binding factor 1/UBF-1 | ylr403w | q92785 | REQ | Zinc-finger protein UBI-D4/apoptosis response zinc finger protein requiem |
| ygr058w | p07384 | CAPN1 | Calpain 1, large [catalytic] subunit/calcium activated neutral proteinase | ygr058w | p07384 | CAPN1 | Calpain 1, large [catalytic] subunit/calcium activated neutral proteinase |
| ygr058w | p17655 | CAPN2 | Ca2-activated neutral proteinase/calpain 2, Large [catalytic] subunit | ygr058w | p17655 | CAPN2 | Ca2-activated neutral proteinase/calpain 2, Large [catalytic] subunit |
| ygr058w | p20807 | CAPN3 | Calpain P94, large [catalytic] subunit/CANP | ygr058w | p20807 | CAPN3 | Calpain P94, large [catalytic] subunit/CANP |
| ygr058w | p28676 | GCA | Grancalcin | ygr058w | p28676 | GCA | Grancalcin |
| ygr058w | p30626 | SR1 | Sorcin | ygr058w | p30626 | SRI | Sorcin |
| ygr058w | p07384 | CAPN1 | Calpain 1, large [catalytic] subunit/calcium activated neutral proteinase | ygr136w | p46108 | CRK | Proto-oncogene C-CRK |
| ygr058w | p17655 | CAPN2 | Ca2-activated neutral proteinase/calpain 2, Large [catalytic] subunit | ygr136w | p06241 | FYN | Proto-oncogene tyrosine-protein kinase FYN/SYN |
| ygr058w | p20807 | CAPN3 | Calpain P94, large [catalytic] subunit/CANP | ygr136w | p29354 | GRB2 | Growth factor receptor-bound protein 2 |
| ygr058w | p28676 | GCA | Grancalcin | ygr136w | p46109 | CRKL | Crk-like protein |
| ygr058w | p30626 | SRI | Sorcin | ygr136w | p14317 | HCLS1 | Hematopoietic lineage cell specific protein |
| ygr058w | p07384 | CAPN1 | Calpain 1, large [catalytic] subunit/calcium activated neutral proteinase | ylr113w | q13164 | MAPK7 | Mitogen-activated protein kinase 7/ERK5 |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ygr058w | p17655 | CAPN2 | Ca2-activated neutral proteinase/calpain 2, Large [catalytic] subunit | ylr113w | p53778 | MAPK12 | Mitogen-activated protein kinase 12/ERK6/extracellular signal-regulated kinase 6 |
| ygr058w | p20807 | CAPN3 | Calpain P94, large [catalytic] subunit/CANP | ylr113w | p45984 | MAPK9 | Mitogen activated protein kinase 9 |
| ygr058w | p28676 | GCA | Grancalcin | ylr113w | p28482 | MAPK1 | Mitogen-activated protein kinase 1/extracellular signal-regulated kinase 2 |
| ygr058w | p30626 | SRI | Sorcin | ylr113w | p53779 | MAPK10 | Mitogen-activated protein kinase 10 |
| ygr058w | p07384 | CAPN1 | Calpain 1, large [catatytic] subunit/calcium activated neutral proteinase | ynl047c | q92636 | NSMAF | Protein fan/factor asociated with n-smase activation |
| ygr058w | p28676 | GCA | Grancalcin | ynl047c | q99418 | ARNO | ARF nucleotide-binding site opener/ARNO protein/ARF exchange factor |
| ygr108w | p14635 | CCNB1 | G2/mitotic-specific cyclin B1 | ybr135w | p10275 | AR | Androgen receptor |
| ygr119c | p23490 | LOR | Loricrin | ygl172w | p35658 | NUP214 | Nuclear pore complex protein NUP214/CAN protein |
| ygr119c | p35637 | FUS | RNA-binding protein FUS/TLS | ygl172w | p49790 | NUP153 | Nuclear pore complex protein NUP153. |
| ygr119c | p35658 | NUP214 | Nuclear pore complex protein NUP214/CAN protein | ygl172w | p09651 | HNRPA1 | Heterogenous nuclear ribonucleoprotein A1/helix-destabilizing protein/single-strand binding protein/HNRNP core protein A1 |
| ygr119c | p37198 | NUP62 | Nuclear pore glycoprotein P62 | ygl172w | p23490 | LOR | Loricrin |
| ygr119c | p49790 | NUP153 | Nuclear pore complex protein NUP153. | ygl172w | p52948 | NUP98 | Nuclear pore complex protein NUP98/Nucleoporin NUP 98 |
| ygr119c | p52948 | NUP98 | Nuclear pore complex protein NUP98/Nucleoporin NUP 98 | ygl172w | p13645 | KRT10 | Keratin, type I cytoskeletal 10 |
| ygr119c | p23490 | LOR | Loricrin | yjl041w | q14093 | CYLC2 | Cylicin II |
| ygr119c | p35637 | FUS | RNA-binding protein FUS/TLS | yjl041w | p35663 | CYLC1 | Cyclin I |
| ygr119c | p35658 | NUP214 | Nuclear pore complex protein NUP214/CAN protein | yjl041w | p35658 | NUP214 | Nuclear pore complex protein NUP214/CAN protein |
| ygr119c | p37198 | NUP62 | Nuclear pore glycoprotein P62 | yjl041w | p37198 | NUP62 | Nuclear pore glycoprotein P62 |
| ygr119c | p49790 | NUP153 | Nuclear pore complex protein NUP153. | yjl041w | p49790 | NUP153 | Nuclear pore complex protein NUP153. |
| ygr119c | p52948 | NUP98 | Nuclear pore complex protein NUP98/Nucleoporin NUP 98 | yjl041w | p52948 | NUP98 | Nuclear pore complex protein NUP98/Nucleoporin NUP 98 |
| ygr119c | p23490 | LOR | Loricrin | ylr423c | p15924 | DSP | Desmoplakin I and II |
| ygr119c | p35637 | FUS | RNA-binding protein FUS/TLS | ylr423c | p49454 | CENPF | CENP-F kinetochore protein |
| ygr119c | p35658 | NUP214 | Nuclear pore complex protein NUP214/CAN protein | ylr423c | p30622 | RSN | Restin |
| ygr119c | p37198 | NUP62 | Nuclear pore glycoprotein P62 | ylr423c | q02224 | CENPE | Centromeric protein E/CENP-E protein |
| ygr119c | p49790 | NUP153 | Nuclear pore complex protein NUP153. | ylr423c | p13535 | MYH8 | Myosin heavy chain, perinatal skeletal muscle |
| ygr119c | p52948 | NUP98 | Nuclear pore complex protein NUP98/Nucleoporin NUP 98 | ylr423c | p12270 | TPR | Nucleoprotein TPR |
| ygr119c | p37198 | NUP62 | Nuclear pore glycoprotein P62 | Ymr236w | q16594 | TAF2G | Transcription initiation factor TFIID 31 kD subunit |
| ygr144w | q16134 | ETFDH | Electron transfer flavoprotein-ubiquinone oxidereductase | ygr144w | q16134 | ETFDH | Electron transfer flavoprotein-ubiquinone oxidereductase |
| ygr155w | p35520 | CBS | Cystathionine beta-synthase | ycr086w | p39880 | CUTL1 | CCAAT displacement protein/CDP |
| ygr229c | p46100 | ATRX | Transcriptional regulator ATRX/X-linked helicase II/X-linked nuclear protein | ykr099w | p10243 | MYBL1 | Myb-related protein A/A-myb |
| ygr229c | p46821 | MAP1B | Microtubule-associated protein 1B | ykr099w | p25054 | APC | Adenomatous polyposis coli protein |
| ygr229c | q05682 | CALD1 | Caldesmon/CDM | ykr099w | p10242 | MYB | MYB proto-oncogene protein |
| ygr229c | q07283 | THH | Trichohyalin | ykr099w | p10244 | MYBL2 | Myb-related protein B/B-myb |
| ygr250c | p11940 | PABPL1 | PolyA binding protein 1 | yir001c | p26378 | ELAVL4 | Paraneoplastic encephalomyelitis antigen 3 |
| ygr250c | p26378 | ELAVL4 | Paraneoplastic encephalomyelitis antigen 3 | yir001c | q01844 | EWSR1 | RNA-binding protein EWS |
| ygr250c | p29558 | RBMS1 | Single-stranded DNA binding protein | yir001c | p35637 | FUS | RNA-binding protein FUS/TLS |
| ygr250c | p33240 | CSTF2 | Cleavage stimulation factor, 64 kD | yir001c | p33240 | CSTF2 | Cleavage stimulation factor, 64 kD subunit |
| ygr250c | p38159 | HNRPG | Heterogeneous nuclear ribonucleoprotein G/HNRNP G/glycoprotein P43 | yir001c | q01085 | TIAL1 | Nucleolysin TIAR |
| ygr250c | p98179 | RBM3 | Putative RNA binding protein 3 | yir001c | p11940 | PABPL1 | PolyA binding protein 1 |
| ygr250c | q01085 | TIAL1 | Nucleolysin TIAR | yir001c | p08621 | SNRP70 | U1 small nuclear ribonucleoprotein 70kD |
| ygr250c | q15427 | SAP49 | Spliceosome associated protein 49/SAP49 | yir001c | p98179 | RBM3 | Putative RNA binding protein 3 |
| ygr267c | p30793 | GCH1 | GTP cyclohydrolase | ygr267c | p30793 | GCH1 | GTP cyclohydrolase I |
| yhl004w | p08865 | LAMR1 | Colon carcinoma laminin-binding protein | ylr423c | q02224 | CENPE | Centromeric protein E/CENP-E protein |
| yhl018w | p80095 | PCBD | Pterin-4-alpha-carbinolamine dehydratase | yhl018w | p80095 | PCBD | PTERIN-4-ALPHA-CARBINOL-AMINE DEHYDRATASE |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yhl019c | p20172 | CLAPM1 | Clathrin coat assembly protein AP50/KIAA0109 gene | ykl135c | p21851 | CLAPB1 | Beta adaptin |
| yhl019c | p53677 | P47B | Clathrin coat assembly protein AP47 homolog 2 | ykl135c | q10567 | ADTB1 | Beta-adaptin 1 |
| yhl027w | p08047 | SP1 | Transcription factor SP1 [fragment] | yjl056c | p52745 | ZNF36 | Zinc finger protein 36/zinc finger protein KOX18 |
| yhl027w | p08151 | GLI1 | GLI protein/zinc finger protein GLI1 | yjl056c | p52740 | ZNF132 | Zinc finger protein 132 |
| yhl027w | p10070 | GLI2 | Tax helper protein 2/zinc finger protein GLI2 | yjl056c | p52736 | ZNF133 | Zinc finger protein 133 |
| yhl027w | p10071 | GLI3 | Zinc finger protein GLI3 | yjl056c | p52742 | ZNF135 | Zinc finger protein 135 |
| yhl027w | p11161 | EGR2 | Early growth response protein 2/EGR-2 | yjl056c | q15072 | ZNF146 | Zinc finger protein OZF |
| yhl027w | p18146 | EGR1 | Early growth response protein 1 | yjl056c | q16600 | ZNF239 | Zinc finger protein 239/HOK-2 |
| yhl027w | p19544 | WT1 | Wilms' tumor protwin/WT33 | yjl056c | p17032 | ZNF37A | Zinc finger protein 37A [fragment] |
| yhl027w | p28160 | ZNF43 | Zinc finger protein 43/Zinnc protein HTF6 | yjl056c | q13360 | ZNF177 | Zinc finger protein 177 |
| yhl027w | q02446 | SP4 | Transcription factor SP4/SPR-1 | yjl056c | p51786 | ZNF157 | Zinc finger protein 157 |
| yhl027w | q05215 | EGR4 | Early growth response protein 4 | yjl056c | q06730 | ZNF33A | Zinc finger protein 33A/KIAA0065 |
| yhl027w | q06889 | EGR3 | Early growth response protein 3 | yjl056c | q05516 | ZNF145 | Zinc finger protein PLZF/zinc finger protein 145 |
| yhr016c | p06241 | FYN | Proto-oncogene tyrosine-protein kinase FYN/SYN | Ymr255w | q03111 | ENL | ENL protein |
| yhr016c | p14317 | HCLS1 | Hematopoietic lineage cell specific protein | Ymr255w | p29375 | RBBP2 | RBBP-2/retinoblastoma binding protein 2 |
| yhr016c | p16333 | NCK | Cytoplasmic protein NCK | Ymr255w | p11387 | TOP1 | Topoisomerase I |
| yhr016c | p29354 | GRB2 | Growth factor receptor-bound protein 2 | Ymr255w | p46821 | MAP1B | Microtubule-associated protein 1B |
| yhr016c | p41240 | CSK | Tryosine-protein kinase CSK | Ymr255w | p51825 | MLLT2 | AF-4 protein |
| yhr016c | q13813 | SPTA2 | Spectrin alpha chain, brain/nonerythroid alpha-spectrin | Ymr255w | o14647 | CHD2 | Chromodomain-helicase-DNA-binding priten 2/CHD-2 |
| yhr016c | q15811 | ITSN | Intersectin/SH3 domain-containing protein SH3P17 | Ymr255w | p46939 | UTRN | Utrophin |
| yhr039c | p30837 | ALDH5 | Mitochondrial aldehyde dehydrogenase X | ydr480w | p17931 | LGALS3 | Galectin-3/IgE-binding protein |
| yhr060w | p25789 | PSMA4 | Proteasome subunit C9 | ylr447c | q02547 | ATP6E | Vacuolar ATP synthase subunit AC39 |
| yhr084w | p24928 | POLR2A | DNA-directed RNA potymerase II largest subunit. | ydr480w | p17931 | LGALS3 | Galectin-3/IgE-binding protein |
| yhr108w | q03001 | BPAG1 | Bullous 230 kDa pemphigoid antigen 1 | ylr423c | q02224 | CENPE | Centromeric protein E/CENP-E protein |
| yhr111w | p22314 | UBE1 | Ubiquitin activating enzyme E1 | yhr111w | p22314 | UBE1 | Ubiquitin activating enzyme E1 |
| yhr111w | p41226 | UBE1L | Ubiquitin-activating enzyme E1 homolog | yhr111w | p41226 | UBE1L | Ubiquitin-activating enzyme E1 homolog |
| yhr114w | p07332 | FES | C-FES/proto-oncogene tyrosine-protein kinase FES/FPS | ylr423c | p49454 | CENPF | CENP-F kinetochore protein |
| yhr114w | p12270 | TPR | Nucleoprotein TPR | ylr423c | p05787 | KRT8 | Keratin, type II cytoskeletal 8/cytokeratin 8/K8/CK8 |
| yhr114w | p12883 | MYH7 | Myosin heavy chain, cardiac muscle beta isoform | ylr423c | p13535 | MYH8 | Myosin heavy chain, perinatal skeletal muscle |
| yhr114w | p14317 | HCLS1 | Hematopoietic lineage cell specific protein | ylr423c | p15924 | DSP | Desmoplakin I and II |
| yhr114w | p16333 | NCK | Cytoplasmic protein NCK | ylr423c | p30622 | RSN | Restin |
| yhr114w | p16591 | FER | Tyrosine kinase FER | ylr423c | q02224 | CENPE | Centromeric protein E/CENP-E protein |
| yhr114w | p98171 | RGC1 | RHO-GAP hematopoietic protein C1 | ylr423c | p12270 | TPR | Nucleoprotein TPR |
| yhr114w | q14247 | CTTN | SRC substrate cortactin/amplaxin | ylr423c | p11047 | LAMC1 | Laminin gamma-1 chain [precursor]/laminin B2 chain |
| yhr114w | q15811 | ITSN | Intersectin/SH3 domain-containing protein SH3P17 | ylr423c | q15431 | SYCP1 | Synaptonemal complex protein 1/SCP-1 protein |
| yhr143w-a | p53803 | POLR2K | DNA-directed RNA polymerases I, II, III 7.0 kD polypeptide | ylr423c | q02224 | CENPE | Centromeric protein E/CENP-E protein |
| yhr171w | p22314 | UBE1 | Ubiquitin activating enzyme E1 | ynr007c | p19338 | NCL | Nucleolin/protein C23 |
| yhr204w | p33908 | MA12 | Mannosyl-oligosaccharide alpha-1,2-mannosidase | ygl030w | p04645 | RPL30 | Ribosomal protein L30 |
| yil013c | p45844 | ABCG1 | White protein homolog | ydr174w | p09429 | HMG1 | High mobility group-1 protein |
| yil074c | p56545 | CTBP2 | C-terminal binding protein 2 | yer081w | p56545 | CTBP2 | C-terminal binding protein 2 |
| yil074c | q13363 | CTBP1 | C-terminal binding protein 1 | yer081w | q13363 | CTBP1 | C-terminal binding protein 1 |
| yil074c | p56545 | CTBP2 | C-terminal binding protein 2 | yil074c | p56545 | CTBP2 | C-terminal binding protein 2 |
| yil074c | q13363 | CTBP1 | C-terminal binding protein 1 | yil074c | q13363 | CTBP1 | C-terminal binding protein 1 |
| yil105c | p20226 | TBP | TATA-binding protein/transcription initiation factor TFIID | yer179w | q14565 | DMC1 | Meiotic recombination protein DMC1/LIM15 homolog |
| yil105c | q93074 | KIAA0192 | Hypothetical protein KIAA0192 | yer179w | q06609 | RAD51 | DNA repair protein RAD51 |
| yil105c | p20226 | TBP | TATA-binding protein/transcription initiation factor TFIID | ynl047c | q99418 | ARNO | ARF nucleotide-binding site opener/ARNO protein/ARF exchange factor |
| yil105c | q93074 | KIAA0192 | Hypothetical protein KIAA0192 | ynl047c | q92636 | NSMAF | Protein fan/factor associated with n-smase activation |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yir005w | p33240 | CSTF2 | Cleavage stimulation factor, 64 kD subunit | ygl174w | p35663 | CYLC1 | Cyclin I |
| yjl036w | p08670 | VIM | Vimentin | ylr423c | p30622 | RSN | Restin |
| yjl036w | p12882 | MYSS | Myosin heavy chain skeletal muscle, light meromyosin region | ylr423c | p15924 | DSP | Desmoplakin I and II |
| yjl036w | p35580 | MYH10 | Myosin heavy chain, nonmuscle type B/ cellular myosin heavy chain, type B/ NMMHC-B | ylr423c | p49454 | CENPF | CENP-F kinetochore protein |
| yjl036w | p35749 | MYH11 | Myosin heavy chain, smooth muscle isoform/SMMHC [FRAGMENT] | ylr423c | p12270 | TPR | Nucleoprotein TPR |
| yjl036w | p48681 | NES | Nestin | ylr423c | p13535 | MYH8 | Myosin heavy chain, perinatal skeletal muscle |
| yjl036w | p49454 | CENPF | CENP-F kinetochore protein | ylr423c | q02224 | CENPE | Centromeric protein E/CENP-E protein |
| yjl036w | q15036 | KIAA0064 | Hypothetical protein KIAA0064 | ylr423c | q15431 | SYCP1 | Synaptonemal complex protein 1/SCP-1 protein |
| yjl092w | p35580 | MYH10 | Myosin heavy chain, nonmuscle type B/ cellular myosin heavy chain, type B/ NMMHC-B | ydr510w | p55854 | SMT3H1 | Ubiquitin-like protein SMT3A |
| yjl092w | p35580 | MYH10 | Myosin heavy chain, nonmuscle type B/ cellular myosin heavy chain, type B/ NMMHC-B | yor355w | p42568 | MLLT3 | AF-9 protein |
| yjl110c | p23769 | GATA2 | Endothelial transcription factor GATA-2 | ynl021w | q13547 | HDAC1 | Histone deacetylase 1/HD1 |
| yjl110c | p23771 | GATA3 | Trans-acting T-cell specific transcription factor GATA-3 | ynl021w | q92769 | HDAC2 | Histone deacetylase 2/HD2 |
| yjl110c | p43694 | GATA4 | Transcription factor GATA-4 | ynl021w | o15379 | DHAC3 | Histone deacetylase 3 |
| yjl110c | q92908 | GATA6 | Transcription factor GATA-6 | ynl021w | p56524 | KIAA0288 | Hypothetical protein KIAA0288 |
| yjl112w | p11016 | GNB2 | Guanine nucleotide-binding protein beta subunit 2 | yll001w | q05193 | DNM1 | Dynamin-1 |
| yjl112w | p43034 | PAFAH1B1 | Platelet-activating factor acetyl-hydrolase IB alpha subunit | yll001w | p20591 | MX1 | Interferon-regulated resistance GTP-binding protein MXA/interferon-induced protein P78 |
| yjl112w | q12788 | SAZD | WD-repeat protein SAZD | yll001w | p50570 | DNM2 | Dynamin-2 |
| yjl112w | q15542 | TAF2D | Transcription initiation factor TFIID 100 Kd subunit/TAFII-100/TAFII100 | yll001w | p20592 | MX2 | Interferon-regulated resistance GTP-binding protein MXB |
| yjl137c | p46976 | GYG | Glycogenin-1 | yjl137c | p46976 | GYG | Glycogenin-1 |
| ykl028w | p07199 | CENP-B | Major centromere autoantigen B/ centromere protein B | ydr311w | p32780 | BTF2 | Basic transcription factor 62kD subunit |
| ykl028w | p07199 | CENP-B | Major centromere autoantigen B/ centromere protein B | ykr062w | p29084 | GTF2E2 | Transcription factor IIE beta subunit |
| ykl067w | o00746 | NME4 | Nucleoside-diphosphate kinase | ykl067w | o00746 | NME4 | Nucleoside diphosphate kinase, mitochondrial |
| ykl067w | p15531 | NME1 | Nucleoside-diphosphate kinase A | ykl067w | p15531 | NME1 | Nucleoside diphosphate kinase A |
| ykl067w | p22392 | NME2 | Nucleoside diphosphate kinase B/NDP kinase B/nm23-H2 | ykl067w | p22392 | NME2 | Nucleoside diphosphate kinase B/NDP kinase B/nm23-H2 |
| ykl142w | p07942 | LAMB1 | Laminin beta-1 chain/Laminin B1 chain | ykl142w | p07942 | LAMB1 | Laminin beta-1 chain/Laminin B1 chain |
| ykl142w | p07942 | LAMB1 | Laminin beta-1 chain/Laminin B1 chain | Ymr165c | p51825 | MLLT2 | AF-4 protein |
| ykl166c | p14619 | PRKG1 | Type 1 beta cGMP-dependent protein kinase | yil033c | p10644 | PRKAR1A | cAMP-dependent protein kinase regulatory subunit type I-alpha |
| ykl166c | p17612 | PRKACA | cAMP-dependent protein kinase catalytic subunit type alpha | yil033c | q16281 | CNCG3 | CNG3/cyclic nucleotide-gated cation channel 3 [fragment] |
| ykl166c | p22694 | PRKACB | Testis-specific cAMP-dependent protein kinase catalytic subunit C-beta isoform | yil033c | q14028 | CNG4 | Cyclic-nucleotide-gated cation channel 4 |
| ykl166c | p23443 | RPS6KB1 | P70 ribosomal S6 kinase alpha-II | yil033c | p29973 | CNCG1 | cGMP-gated cation channel protein/ cyclic nucleotide gated channel, photoreceptor/cyclic-nucleotide-gated cation channel1/CNG channel 1/CNG1/CNG-1 |
| ykl166c | p24723 | PRKCH | Protein kinase C, ETA type/protein-kinase C-L | yil033c | p31321 | PRKAR1B | cAMP-dependent protein kinase regulatory subunit RI-beta |
| ykl166c | p31749 | AKT1 | RAC-alpha serine/threonine kinase | yil033c | p13861 | PRKAR2A | cAMP-dependent protein kinase type II-alpha regulatory chain |
| ykl166c | p31751 | AKT2 | RAC-beta serine/threonine kinase | yil033c | p31323 | PRKAR2B | cAMP-dependent protein kinase subunit RII-beta |
| ykl166c | p51812 | RPS6KA3 | Ribosomal protein 56 kinase II alpha 3/insulin-stimulated protein kinase 1 | yil033c | p14619 | PRKG1 | Type I beta cGMP-dependent protein kinase |
| ykr026c | p49770 | EIF2B2 | Translation initiation factor EIF-2B beta subunit/S20iii15 | ykr026c | p49770 | EIF2B2 | Translation initiation factor EIF-2B beta subunit/S20iii15 |
| ykr026c | q14232 | ELF2B1 | Translation initiation factor eIF-2B alpha subunit | ykr026c | q14232 | ELF2B1 | Translation initiation factor eIF-2B alpha subunit |
| ykr037c | p42566 | EPS15 | Epidermal growth factor receptor substrate 15 | ydr201w | p30622 | RSN | Restin |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ykr083c | p09429 | HMG1 | High mobility group-1 protein | ykl052c | p19338 | NCL | Nucleolin/protein C23 |
| ykr083c | p17480 | UBTF | Nucleolar transcription factor 1/ upstream binding factor 1/UBF-1 | ykl052c | q92794 | MOZ | Monocytic leukemia zinc finger protein |
| yll046c | p33240 | CSTF2 | Cleavage stimulation factor, 64 kD subunit | yfr047c | q15274 | NADC | Nicotinate-nucleotide pyrophosphorylase [carboxylating]/ quinolinate phosphoribosyl transferase |
| ylr200w | p49454 | CENPF | CENP-F kinetochore protein | Ymr052c | p30622 | RSN | Restin |
| ylr200w | q02224 | CENPE | Centromeric protein E/CENP-E protein | Ymr052w | p35560 | MYH10 | Myosin heavy chain, nonmuscle type B/ cellulary myosin heavy chain, type B/ NMMHC-B |
| ylr216c | p05092 | CYPA | Peptidyl-prolyl cis-trans isomerase A/cyclophilin A | ylr037w | p36969 | GPX4 | Phospholpid hydroperoxide glutathione peroxidase/PHGPX |
| ylr216c | p23284 | PPIB | Peptidyl-proyl CIS-trans isomerase B [precursor]/cyclophilin B | ylr037w | p18283 | GPX2 | Glutathione peroxidase-GI. |
| ylr216c | p30405 | CYP3 | Peptidyl-prolyl CIS-Trans isomerase/ cyclophilin | ylr037w | p12079 | GPRP | Glutathione peroxidase-related protein 1 |
| ylr216c | p45877 | PPIC | Peptidyl-prolyl cis-trans isomerase C/ cyclophilin C | ylr037w | p22352 | GPX3 | Plasma glutathione peroxidase |
| ylr216c | q08752 | PPID | 40 kD peptidyl-prolyl CIS-TRANS isomerase/cyclophilin-40 mRNA, complete cds. | ylr037w | p07203 | GPX1 | Glutathione peroxidase |
| ylr229c | p21181 | CDC42 | G25K GTP-binding protein | ydl135c | p52565 | ARHGDIA | Rho GDP-dissociation inhibitor 1. |
| ylr229c | p25763 | CDC42 | GTP-binding protein G25K, placental isoform | ydl135c | p52566 | ARHGD1B | Rho GDP-dissociation inhibitor 2 |
| ylr245c | p32320 | CDA | Cytidine deaminase | ylr245c | p32320 | CDA | Cytidine deaminase - |
| ylr305c | p42336 | PIK3CA | Phosphatidylinositol 3-kinase catalytic subunit, alpha isoform | yor355w | q14669 | TRIP12 | Thyroid receptor interacting protein 12/ KIAA0045 |
| ylr305c | p42345 | FRAP | FKBP-rapamycin associated protein | yor355w | p42568 | MLLT3 | AF-9 protein |
| ylr423c | p15924 | DSP | Desmoplakin I and II | ygr120c | p30622 | RSN | Restin |
| ylr423c | p49454 | CENPF | CENP-F kinetochore protein | ygr120c | p49454 | CENPF | CENP-F kinetochore protein |
| ylr423c | q02224 | CENPE | Centromeric protein E/CENP-E protein | ygr120c | p04114 | APOB | Apolipoprotein B |
| ylr423c | p05787 | KRT8 | Keratin, type II cytoskeletal 8/ cytokeratin 8/K8/CK8 | ylr423c | p05787 | KRT8 | Keratin, type II cytoskeletal 8/ cytokeratin 8/K8/CK8 |
| ylr423c | p11047 | LAMC1 | Laminin gamma-1 chain [precursor]/ laminin B2 chain | ylr423c | p11047 | LAMC1 | Laminin gamma-1 chain [precursor]/ laminin B2 chain |
| ylr423c | p12270 | TPR | Nucleoprotein TPR | ylr423c | p12270 | TPR | Nucleoprotein TPR |
| ylr423c | p13535 | MYH8 | Myosin heavy chain, perinatal skeletal muscle | ylr423c | p13535 | MYH8 | Myosin heavy chain, perinatal skeletal muscle |
| ylr423c | p15924 | DSP | Desmoplakin I and II | ylr423c | p15924 | DSP | Desmoplakin I and II |
| ylr423c | p30622 | RSN | Restin | ylr423c | p30622 | RSN | Restin |
| ylr423c | p49454 | CENPF | CENP-F kinetochore protein | ylr423c | p49454 | CENPF | CENP-F kinetochore protein |
| ylr423c | q02224 | CENPE | Centromeric protein E/CENP-E protein | ylr423c | q02224 | CENPE | Centromeric protein E/CENP-E protein |
| ylr423c | q15431 | SYCP1 | Synaptonemal complex protein 1/SCP-1 protein | ylr423c | q15431 | SYCP1 | Synaptonemal complex protein 1/SCP-1 protein |
| ylr424w | p49454 | CENPF | CENP-F kinetochore protein | ykr022c | p19454 | CENPF | CENP-F kinetochore protein |
| ylr424w | p52756 | LUCA15 | Putative tumor suppressor LUCA15 | ykr022c | p13535 | MYH8 | Myosin heavy chain, perinatal skeletal muscle |
| ylr424w | p98175 | DXS8237E | DXS8237E protein | ykr022c | p35580 | MYH10 | Myosin heavy chain, nonmuscle type B/ cellulary myosin heavy chain, type B/ NMMHC-B |
| ylr429w | p31146 | CORO1 | Coronin-like Protein p57 | ydr328c | p07199 | CENP-B | Major centromere autoantigen B/ centromere protein B |
| ylr429w | p43034 | PAFAH1B1 | Platelet-activating factor acetyl-hydrolase IB alpha subunit | ydr328c | p34991 | TCEB1L | Cyclin A/CDK2-associated p19 |
| ylr429w | p46821 | MAP1B | Microtubule-associated protein 1B | ydr328c | p17480 | UBTF | Nucleolartranscription factor 1/ upstream binding factor 1/UBF-1 |
| ylr429w | q16576 | RBBP7 | Histone acetyl transferase type B subunit 2/retinoblastoma-binding protein | ydr328c | p19338 | NCL | Nucleolin/protein C23 |
| ylr432w | p12268 | IMPDH2 | Inosine monophosphate dehydrogenase 2 | ydr167w | q12962 | TAF2H | Transcription initiation factor TFIID 30 Kd subunit/TAFII-30/TAFII30 |
| ylr432w | p12268 | IMPDH2 | Inosine monophosphate dehydrogenase 2 | ykr026c | q14232 | ELF2B1 | Translation initiation factor eIF-2B alpha subunit |
| ylr432w | p20839 | IMPDH1 | Inosine-5'-monophosphate dehydrogenase 1/IMPDH-I/IMPD | ykr026c | p49770 | EIF2B2 | Translation initiation factor EIF-2B beta subunit/S20iii15 |
| ylr433c | p05323 | PPP2CA | Serine/threonine protein phosphatase PP2A-alpha, catalytic subunit | ynl047c | q99418 | ARNO | ARF nucleotide-binding site opener/ ARNO protein/ARF exchange factor |
| ylr433c | q08209 | PPP3CA | Serine/threonine protein phosphatase 2B catalytic subunit. Alpha isoform / calmodulin-dependent calcineurin A subunit, alpha subunit | ynl047c | q92636 | NSMAF | Protein fan/factor asociated with n-smase activation |
| ylr438w | p04181 | OAT | Ornithine aminotransferase | ygr010w | q92764 | KRTHA5 | Keratin, type I cuticular HA5/hair keratin, type I HA5 |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ylr438w | p04181 | OAT | Ornithine aminotransferase | yhl025w | p20226 | TBP | TATA-binding protein/transcription initiation factor TFIID |
| yml015c | p52655 | GTF2A1 | Transcription initiation factor IIA alpha and beta chains/TFIIA-42 | ydr167w | q12962 | TAF2H | Transcription initiation factor TFIID 30 Kd subunit/TAFII-30/TAFII30 |
| yml015c | p52655 | GTF2A1 | Transcription initiation factor IIA alpha and beta chains/TFIIA-42 | ydr174w | p09429 | HMG1 | High mobility group-1 protein |
| yml015c | q15544 | TAF2I | Transcription initiation factor TFIID 28 kD subunit | ydr174w | p26583 | HMG2 | High mobility group protein HMG2/HMG-2 |
| yml088w | p46100 | ATRX | Transcriptional regulator ATRX/X-linked helicase II/X-linked nuclear protein | ydr328c | p07199 | CENP-B | Major centromere autoantigen B/centromere protein B |
| yml094w | p49454 | CENPF | CENP-F kinetochore protein | ylr200w | q02224 | CENPE | Centromeric protein E/CENP-E protein |
| yml094w | q99471 | MM-1 | C-myc binding protein MM-1 | ylr200w | p49454 | CENPF | CENP-F kinetochore protein |
| yml114c | q02832 | BLSA | B-lymphocyte antigen/B-lymphocyte surface antigen | ydr167w | q12962 | TAF2H | Transcription initiation factor TFIID 30 Kd subunit/TAFII-30/TAFII30 |
| ymr032w | p02533 | KRT14 | Keratin, type I cytoskeletal 14 | ylr423c | p49454 | CENPF | CENP-F kinetochore protein |
| ymr032w | p13533 | MYH6 | Myosin heavy chain, cardiac muscle alpha isoform | ylr423c | q02224 | CENPE | Centromeric protein E/CENP-E protein |
| ymr052w | p30622 | RSN | Restin | yfr008w | p12270 | TPR | Nucleoprotein TPR |
| ymr052w | p35580 | MYH10 | Myosin heavy chain, nonmuscle type B/cellular myosin heavy chain, type B/NMMHC-B | yfr008w | q02224 | CENPE | Centromeric protein E/CENP-E protein |
| ymr068w | p20749 | BCL3 | B-cell lymphoma 3-encoded protein | yil105c | q10571 | MN1 | Probable tumor suppressor protein MN1 |
| ymr068w | q01484 | ANK2 | Ankyrin, brain variant 1/ankyrin B | yil105c | p20226 | TBP | TATA-binding protein/transcription initiation factor TFIID |
| ymr068w | q01485 | ANK2 | Brain ankyrin variant 2 | yil105c | q93074 | KIAA0192 | Hypothetical protein KIAA0192 |
| ymr077c | p12270 | TPR | Nucleoprotein TPR | ykl052c | p19338 | NCL | Nucleolin/protein C23 |
| ymr077c | p35579 | MYH9 | Myosin heavy chain, nonmuscle type A/cellular myosin heavy chain, type A/NMMHC-A | ykl052c | q92794 | MOZ | Monocytic leukemia zinc finger protein |
| ymr091c | p07199 | CENP-B | Major centromere autoantigen B/centromere protein B | yfr037c | q15431 | SYCP1 | Synaptonemal complex protein 1/SCP-1 protein |
| ymr093w | o14727 | APAF1 | Apoptotic protease activating factor 1 APAF-1 | ydr398w | p17480 | UBTF | Nucleolin/transcription factor 1/upstream binding factor 1/UBF-1 |
| ymr093w | p25388 | GNB2-RS1 | Guanine nucleotide-binding protein beta subunit-like protein 12.3 | ydr398w | p07199 | CENP-B | Major centromere autoantigen B/centromere protein B |
| ymr093w | p35606 | COPP | Beta subunit of coatomer complex | ydr398w | p27824 | CANX | Calnexin/IP90 |
| ymr093w | q13610 | PWP1 | Periodic tryptophan protein 1 homolog/keratinocyte protein IEF SSP 9502 | ydr398w | p39687 | PHAP1 | HLA-DR associated protein |
| ymr093w | q15542 | TAF2D | Transcription initiation factor TFIID 100 kD subunit/TAFII-100/TAFII100 | ydr398w | q01105 | SET | Set protein/HLA-DR associated protein II/PHAPII |
| ymr102c | p25388 | GNB2-RS1 | Guanine nucleotide-binding protein beta subunit-like protein 12.3 | ynl218w | p35249 | RFC4 | Activator 137 kD subunit/repiication factor C, 37-kDa subunit |
| ymr102c | p43034 | PAFAH1B1 | Platelet-activating factor acetyl-hydrolase IB alpha subunit | ynl218w | p35250 | RFC2 | Activator 140 kD subunit/repiication factor C, 40 kDa subunit |
| ymr102c | p53621 | COPA | Coatomer alpha subunit | ynl218w | p40937 | RFC5 | Activator 1 36 kD subunit/replication factor C, 36-kDa subunit |
| ymr102c | q13610 | PWP1 | Periodic tryptophan protein 1 homolog/keratinocyte protein IEF SSP 9502 | ynl218w | p35251 | RFC1 | Replication factor C large subunit/activator 1140 Kd subunit |
| ymr210w | p08910 | PHS1-2 | PHS1-2 with ORF homologous to membrane receptor proteins | ykl142w | p07942 | LAMB1 | Laminin beta-1 chain/Laminin B1 chain |
| ymr212c | q14156 | KIAA0143 | Hypothetical protein KIAA0143 | ylr423c | q02224 | CENPE | Centromeric protein E/CENP-E protein |
| ymr255w | o14647 | CHD2 | Chromodomain-helicase-DNA-binding protein 2/CHD-2 | ygl122c | q92794 | MOZ | Monocytic leukemia zinc finger protein |
| ymr255w | p11387 | TOP1 | Topoisomerase I | ygl122c | q93074 | KIAA0192 | Hypothetical protein KIAA0192 |
| ymr255w | p29375 | RBBP2 | RBBP-2/retinoblastoma binding protein 2 | ygl122c | p20226 | TBP | TATA-binding protein/transcription initiation factor TFIID |
| ymr255w | p46821 | MAP1B | Microtubule-associated protein 1B | ygl122c | p51531 | SMARCA2 | Possible global transcription activator SNF2L2/BRM |
| ymr255w | p46939 | UTRN | Utrophin | ygl122c | q10571 | MN1 | Probable tumor suppressor protein MN1 |
| ymr255w | p51825 | MLLT2 | AF-4 protein | ygl122c | p42858 | HD | Huntingtin/huntington's disease protein |
| ymr255w | q03111 | ENL | ENL protein | ygl122c | q14814 | MEF2D | Myocyte-specific enhancer factor 2D |
| ymr267w | q15181 | PP | Inorganic pyrophosphatase [fragment]/Ppase | ykr026c | q14232 | ELF2B1 | Translation initiation factor eIF-2B alpha subunit |
| ymr269w | p35663 | CYLC1 | Cyclin | ykr026c | q14232 | ELF2B1 | Translation initiation factor eIF-2B alpha subunit |
| ymr269w | q14093 | CYLC2 | Cylicin II | ykr026c | p49770 | EIF2B2 | Translation initiation factor EIF-2B beta subunit/S20iii15 |
| ymr309c | p17480 | UBTF | Nucleolar transcription factor 1/upstream binding factor 1/UBF-1 | ynl047c | q92636 | NSMAF | Protein fan/factor asociated with n-smase activation |
| ymr309c | p35580 | MYH10 | Myosin heavy chain, nonmuscle type B/cellular myosin heavy chain, type B/NMMHC-B | ynl047c | q99418 | ARNO | ARF nucleotide-binding site opener/ARNO protein/ARF exchange factor |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ymr309c | p35580 | MYH10 | Myosin heavy chain, nonmuscle type B/ cellular myosin heavy chain, type B/ NMMHC-B | ynl244c | p41567 | SUI1 | Protein translation factor SUI1 homolog/sui1iso1 |
| ynl023c | p35555 | FBN1 | Fibrillin 1 [precursor] | Ymr224c | p49959 | MRE11A | Double-strand break repair protein MRE11A/MRE11 homolog |
| ynl078w | p18583 | SON | Son protein/son3 | ykr048c | p55209 | NAP1L1 | NAP-1/nucleosome assembly protein 1-like 1 |
| ynl091w | q02832 | BLSA | B-lymphocyte antigen/B-lymphocyte surface antigen | ynl164c | q13190 | STX5A | Syntaxin 5 |
| ynl091w | p46821 | MAP1B | Microtubule-associated protein 1B | yor355w | q14669 | TRIP12 | Thyroid receptor interacting protein 12/KIAA0045 |
| ynl091w | q02832 | BLSA | B-lymphocyte antigen/B-lymphocyte surface antigen | yor355w | p42568 | MLLT3 | AF-9 protein |
| ynl091w | p23327 | HRC | Sarcoplasmic reticulum histidine-rich calcium binding protein | yp1229w | p20265 | POU3F2 | Nervous-system specific octamer-binding transcription factor N-Oct 3/N-Oct 5a/N-Oct 5b |
| ynl091w | p35579 | MYH9 | Myosin heavy chain, nonmuscle type A/ cellular myosin heavy chain, type A/ NMMHC-A | yp1229w | p51531 | SMARCA2 | Possible global transcription activator SNF2L2/BRM |
| ynl091w | p35749 | MYH11 | Myosin heavy chain, smooth muscle isoform/SMMHC [FRAGMENT] | yp1229w | q93074 | KIAA0192 | Hypothetica protein KIAA0192 |
| ynl091w | p45379 | TNNT2 | Troponin T, cardiacmuscle isoforms | yp1229w | q01826 | SATB1 | DNA binding protein SATB1 |
| ynl091w | p46100 | ATRX | Transcriptional regulator ATRX/X-linked helicase II/X-linked nuclear protein | yp1229w | p54252 | MJD1 | Machado-joseph disease protein 1 |
| ynl091w | p46821 | MAP1B | Microtubule-associated protein 1B | yp1229w | p42858 | HD | Huntingtin/huntington's disease protein |
| ynl091w | q02832 | BLSA | B-ymphocyte antigen/B-lymphocyte surface antigen | yp1229w | p10275 | AR | Androgen receptor |
| ynl091w | q05682 | CALD1 | Caldesmon/CDM | yp1229w | q10571 | MN1 | Probable tumor suppressor protein MN1 |
| ynl091w | q07283 | THH | Trichohyalin | yp1220w | p20226 | TBP | TATA-binding protein/transcription initiation factor TFIID |
| ynl091w | q15696 | U2AF1-RS2 | U2 small nuclear ribonucleoprotein auxiliary factor 35 kD subunit related-protein 2 | yp1229w | p54253 | SCA1 | Ataxin-1/Spinocerebellar ataxia type 1 protein |
| ynl127w | p20309 | CHRM3 | Muscarinic acetylcholine receptor M3 | yal016w | p30153 | PPP2R1A | Protein phosphatase PP2A, 65Kd regulator subunit alpha-isotype |
| ynl127w | p20309 | CHRM3 | Muscarinic acetylcholine receptor M3 | ykr055w | p21181 | CDC42 | G25K GTP-binding protein |
| ynl154c | p48729 | CSNK1A1 | Casein kinase I, alpha isoform/CK1-alpha/CK1 | ycl054w | q05682 | CALD1 | Caldesmon/CDM |
| ynl154c | p48730 | CSNK1D | Casein kinase I delta isoform | ycl054w | p35663 | CYLC1 | Cyclin I |
| ynl154c | p49674 | CSNK1E | Casein kinase I epsilon | ycl054w | p12883 | MYH7 | MYOSIN, CARDIAC, HEAVY CHAIN, BETA |
| ynl154c | p51812 | RPS6KA3 | Ribosomal protein S6 kinase II alpha 3/insulin-stimulated protein kinase 1 | ycl054w | p19338 | NCL | Nucleolin/protein C23 |
| ynl154c | p78368 | CSNK1G2 | Casein kinase I, gamma 2 isoform | ycl054w | p35579 | MYH9 | Myosin heavy chain, nonmuscle type A/ cellular myosin heavy chain, type A/ NMMHC-A |
| ynl154c | p48730 | CSNK1D | Casein kinase I delta isoform | ycr011c | p45844 | ABCG1 | White protein homolog |
| ynl154c | p48729 | CSNK1A1 | Casein kinase I, alpha isoform/CK1-alpha/CK1 | ykl204w | p10163 | PRB4 | PROLINE-RICH PROTEIN, BstNI SUBFAMILY, 4 |
| ynl154c | p48730 | CSNK1D | Casein kinase I delta isoform | ykl204w | p48634 | BAT2 | Large proline-rich protein BAT2/ HLA-B-associated transcript 2 |
| ynl154c | p49674 | CSNK1E | Casein kinase I epsilon | ykl204w | p54259 | DRPLA | Atrophin-1/dentatorubral-pallidoluysian atrophy protein |
| ynl154c | p51812 | RPS6KA3 | Ribosomal protein S6 kinase II alpha 3/insulin-stimulated protein kinase 1 | ykl204w | p04280 | PRB1 | Salivary proline-rich protein/clone CP3, CP4, and CP5 |
| ynl154c | p78368 | CSNK1G2 | Casein kinase I, gamma 2 isoform | ykl204w | p02812 | PRB2 | Salivary proline-rich protein/Clone CP7 |
| ynl154c | p48730 | CSNK1D | Casein kinase I delta isoform | Ymr267w | q15181 | PP | Inorganic pyrophosphatase [fragment]/ Ppase |
| ynl154c | p48730 | CSNK1D | Casein kinase I delta isoform | yor355w | p42568 | MLLT3 | AF-9 protein |
| ynl154c | p49674 | CSNK1E | Casein kinase I epsilon | yor355w | q14669 | TRIP12 | Thyroid receptor interacting protein 12/ KIAA0045 |
| ynl189w | p35222 | CTNNB1 | Beta-catenin. | ybr252w | p33316 | DUT | Deoxyuridine triphosphatase nucleotidohydrolase |
| ynl180w | p52294 | KPNA1 | Importin alpha-1 subunit/SRP1-beta/ nucleoprotein interactor 1 | ybr252w | p10265 | PRT | Retrovirus-related protease |
| ynl180w | o00505 | KPNA3 | Karyopherin alpha 3 | yhl009c | p17861 | XBP1 | X box binding protein-1/XBP-1 |
| ynl180w | o00629 | QIP1 | Karyopherin alpha 4/Qip1 | yhl009c | q15431 | SYCP1 | Synaptonemal complex protein 1/SCP-1 protein |
| ynl180w | p35222 | CTNNB1 | Beta-catenin. | yhl009c | p25054 | APC | Adenomatous polyposis coli protein |
| ynl189w | p52292 | KPNA2 | Importin alpha-2 subunit/SRP1-alpha | yhl009c | p12270 | TPR | Nucleoprotein TPR |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ynl189w | p52294 | KPNA1 | Importin alpha-1 subunit/SRP1-beta/nucleoprotein interactor 1 | yhl009c | q02224 | CENPE | Centromeric protein E/CENP-E protein |
| ynl189w | p35222 | CTNNB1 | Beta-catenin. | yjr159w | p11766 | ADH5 | Class III alcohol dehydrogenase chi subunit |
| ynl189w | p52294 | KPNA1 | Importin alpha-1 subunit/SRP1-beta/nucleoprotein interactor 1 | yjr159w | q00796 | SORD | Sorbitol dehydrogenase/L-iditol-2 dehydrogenase |
| ynl189w | p35222 | CTNNB1 | Beta-catenin. | ylr303w | p32929 | CTH | Cystathionine gamma-lyase |
| ynl189w | o00505 | KPNA3 | Karyopherin alpha 3 | yml020w | p32119 | TDPX1 | Thioredoxin peroxidase 1/thioredoxin-dependent peroxide reductase 1/thiol-specific antioxidant protein/TSA/PRP/natural killer cell enhancing factor B/NKEF-B |
| ynl189w | o00629 | QIP1 | Karyopherin alpha 4/Qip1 | yml020w | q13162 | AOE372 | Thioredoxin peroxidase AO372/antioxidant enzyme AOE372 |
| ynl189w | p35222 | CTNNB1 | Beta-catenin. | yml028w | q06830 | TDPX2 | Thioredoxin peroxidase 2/proliferation-associated gene (pag). |
| ynl189w | p52292 | KPNA2 | Importin alpha-2 subunit/SRP1-alpha | yml020w | p30041 | AOP2 | Antioxidant protein 2 |
| ynl189w | p52294 | KPNA1 | Importin alpha-1 subunit/SRP1-beta/nucleoprotein interactor 1 | yml020w | p30048 | AOP1 | Mitochondrial thioredoxin-dependent peroxide reductase/antioxidant protein 1 |
| ynl189w | o00505 | KPNA3 | Karyopherin alpha 3 | Ymr226c | p15428 | PGDH1 | 15-Hydroxyprostaglandin dehydrogenase [NAD(+)]/PGDH |
| ynl189w | p35222 | CTNNB1 | Beta-catenin. | Ymr226c | q02338 | BDH | D-beta-hydroxybutyrate dehydrogenase/3-hydroxybutyrate dehydrogenase |
| ynl189w | p52292 | KPNA2 | Importin alpha-2 subunit/SRP1-alpha | Ymr226c | q92781 | RDH1 | 11-cis retinol dehydrogenase |
| ynl189w | p52294 | KPNA1 | Importin alpha-1 subunit/SRP1-beta/nucleoprotein interactor 1 | Ymr226c | p14061 | E2DH | Estradiol 17 beta-dehydrogenase 1/17-beta-HSD 1 |
| ynl189w | p35222 | CTNNB1 | Beta-catenin. | yol058w | p00966 | ASS | Argininosuccinate synthase/citrulline-aspartate ligase |
| ynl189w | p35222 | CTNNB1 | Beta-catenin. | ypl111w | p78540 | ARG2 | Arginase II/non-hepatic arginase |
| ynl189w | p52294 | KPNA1 | Importin alpha-1 subunit/SRP1-beta/nucleoprotein interactor 1 | ypl111w | p05089 | ARG1 | Arginase 1 |
| ynl218w | q00341 | HBP | High density lipoprotein binding protein | ykl142w | p07942 | LAMB1 | Laminin beta-1 chain/Laminin B1 chain |
| ynl218w | p35249 | RFC4 | Activator 137 kD subunit/replication factor C, 37-kDa subunit | ylr423c | p49454 | CENPF | CENP-F kinetochore protein |
| ynl218w | p35250 | RFC2 | Activator 140 kD subunit/replication factor C, 40 kDa subunit | ylr423c | p15924 | DSP | Desmoplakin I and II |
| ynl218w | p35251 | RFC1 | Replication factor C large subunit/activator 1140 Kd subunit | ylr423c | p13535 | MYH8 | Myosin heavy chain, perinatal skeletal muscle |
| ynl218w | p40937 | RFC5 | Activator 136 kD subunit/replication factor C, 36-kDa subunit | ylr423c | q02224 | CENPE | Centromeric protein E/CENP-E protein |
| ynl218w | p35249 | RFC4 | Activator 137 kD subunit/replication factor C, 37-kDa subunit | ynl218w | p35249 | RFC4 | Activator 137 kD subunit/replication factor C, 37-kDa subunit |
| ynl218w | p35250 | RFC2 | Activator 140 kD subunit/replication factor C, 40 kDa subunit | ynl218w | p35250 | RFC2 | Activator 140 kD subunit/replication factor C, 40 kDa subunit |
| ynl218w | p35251 | RFC1 | Replication factor C large subunit/activator 1140 Kd subunit | ynl218w | p35251 | RFC1 | Replication factor C large subunit/activator 1140 Kd subunit |
| ynl218w | p40937 | RFC5 | Activator 136 kD subunit/replication factor C, 36-kDa subunit | ynl218w | p40937 | RFCS | Activator 1136 kD subunit/replication factor C, 36-kDa subunit |
| ynl287w | p21851 | CLAPB1 | Beta adaptin | ybr281c | p31146 | CORO1 | Coroninlike Protein P57 |
| ynl287w | q10567 | ADTB1 | Beta-adaptin 1 | ybr281c | p35606 | COPP | Beta subunit of coatomer complex |
| ynr006w | p12036 | NEFH | Neurofilament triplet H proprotein/200 Kd neurofilament protein | yhl002w | q15811 | ITSN | Intersectin/SH3 domain-containing protein protein SH3P17 |
| ynr006w | p26358 | DNMT | DNA/cytosine-5)0methyl transferase/DNA methyltransferase/DNA metase/MCMT/M.HSAI | yhl002w | q14247 | CTTN | SRC substrate cortactin/amplaxin |
| ynr006w | p46100 | ATRX | Transcriptional regulator ATRX/X-linked helicase II/X-linked nuclear protein | yhl002w | p19174 | PLCG1 | 1-phosphatidylinositol-4,5-bisphosphate phosphodiesterase gamma 1/phospholipase C-gamma 1 |
| ynr006w | p80303 | NEFA | DNA binding protein NEFA | yhl002w | p16333 | NCK | Cytoplasmic protein NCK |
| ynr006w | p98174 | FGD1 | Putative RHO/RAC guanine nucleotide exchange factor/faciogenital dyspiasia protein | yhl002w | p14317 | HCLS1 | Hematopoietic lineage cell specific protein |
| ynr006w | q02224 | CENPE | Centromeric protein E/CENP-E protein | yhl002w | p29354 | GRB2 | Growth factor receptor-bound protein 2 |
| ynr006w | q07283 | THH | Trichohyalin | yhl002w | p98171 | RGC1 | RHO-GAP hematopoietic protein C1 |
| ynr006w | q13438 | OS9 | Protein OS-9 precurosor | yhl002w | p46109 | CRKL | Crk-like protein |
| ynr006w | q92794 | MOZ | Monocytic leukemia zinc finger protein | yhl002w | p14813 | SPTA2 | Spectrin alpha chain, brain/nonerythroid alpha-spectrin |
| yol034w | p11055 | MYH3 | Embryonic myosin heavy chain. | Ymr117c | p04264 | KRT1 | Keratin, type II cytoskeletal 1/cytokeratin 1/K1/CK1/67Kd cytokeratin/hair alpha protein |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yol034w | p12883 | MYH7 | Myosin heavy chain, cardiac muscle beta isoform | Ymr117c | p30622 | RSN | Restin |
| yol034w | p13533 | MYH6 | Myosin heavy chain, cardiac muscle alpha isoform | Ymr117c | p35580 | MYH10 | Myosin heavy chain, nonmuscle type B/ cellular myosin heavy chain, type B/ NMMHC-B |
| yol034w | p15924 | DSP | Desmoplakin I and II | Ymr117c | p11055 | MYH3 | Embryonic myosin heavy chain. |
| yol034w | p49454 | CENPF | CENP-F kinetochore protein | Ymr117c | p42566 | EPS15 | Epidermal growth factor receptor substrate 15 |
| yol034w | q02224 | CENPE | Centromeric protein E/CENP-E protein | Ymr117c | p49454 | CENPF | CENP-F kinetochore protein |
| yol059w | p21695 | GPD1 | L-glycerol-3-phosphate dehydrogenase [NAD+] | yfl017c | p08578 | SNRPE | Small nuclear ribonucleoprotein E/ snRNP-E |
| yol061w | p09329 | PRPS1 | Phosphoribosyl pyrophosphate synthetase I/ribosephosphate pyrophosphokinase I | yer099c | p09329 | PRPS1 | Phosphoribosyl pyrophosphate synthetase I/ribosephosphate pyrophosphokinase 1 |
| yol061w | p11908 | PRPS2 | Phosphoriobosyl pyrophosphate synthetase subunit II | yer099c | p11908 | PRPS2 | Phosphoribosyl pyrophosphate synthetase subunit II |
| yol061w | p21108 | PRPS3 | Phosphoribosyl pyrophosphate synthetase subunit III | yer099c | p21108 | PRPS3 | Phosphoribosyl pyrophosphate synthetase subunit III |
| yol069w | p15924 | DSP | Desmoplakin I and II | yer099c | p21108 | PRPS3 | Phosphoribosyl pyrophosphate synthetase subunit III |
| yol069w | p49454 | CENPF | CENP-F kinetochore protein | yer099c | p11908 | PRPS2 | Phosphoribosyl pyrophosphate synthetase subunit II |
| yol069w | q02224 | CENPE | Centromeric protein E/CENP-E protein | yer099c | p09329 | PRPS1 | PHOSPHORIBOSYLPYROPHOSPHATE SYNTHETASE I |
| yol069w | p12270 | TPR | Nucleoprotein TPR | ylr423c | p05787 | KRT8 | Keratin, type II cytoskeletal 8/ cytokeratin 8/K8/CK8 |
| yol069w | p12883 | MYH7 | Myosin heavy chain, cardiac muscle beta isoform | ylr423c | p30622 | RSN | Restin |
| yol069w | p13533 | MYH6 | Myosin heavy chain, cardiac muscle alpha isoform | ylr423c | p13535 | MYH8 | Myosin heavy chain, perinatal skeletal muscle |
| yol069w | p13535 | MYH8 | Myosin heavy chain, perinatal skeletal muscle | ylr423c | q15431 | SYCP1 | Synaptonemal complex protein 1/SCP-1 protein |
| yol069w | p15924 | DSP | Desmoplakin I and II | ylr423c | p15924 | DSP | Oesmoplakin I and II |
| yol069w | p30622 | RSN | Restin | ylrA23c | p11047 | LAMC1 | Laminin gamma-1 chain [precursor]/ aminin B2 chain |
| yol069w | p35580 | MYH10 | Myosin heavy chain, nonmuscle type B/ cellular myosin heavy chain, type B/ NMMHC-B | ylr423c | p12270 | TPR | Nucleoprotein TPR |
| yol069w | p49454 | CENPF | CENP-F kinetochore protein | ylr423c | p49454 | CENPF | CENP-F kinetochore protein |
| yol069w | q02224 | CENPE | Centromeric protein E/CENP-E protein | ylr423c | q02224 | CENPE | Centromeric protein E/CENP-E protein |
| yol088c | p13667 | ERP72 | Protein disulfide isomerase related protein/ERP72 | yhr091c | p54136 | RARS | ArgRS/arginyl-tRNA synthetase |
| yol105c | q02505 | MUC3 | Mucin 3 [fragments]/intestinal mucin 3 | ygl153w | q02224 | CENPE | Centromeric protein E/CENP-E protein |
| yol105c | q99102 | MUC4 | Tracheo-bronchial mucin 4/mucin 4 [fragment] | ygl153w | q03001 | BPAG1 | Bullous 230 kDa pemphigoid antigen 1 |
| yol108c | p98171 | RGC1 | RHO-GAP hematopoietic protein C1 | ykl017c | p38935 | IGHMBP2 | DNA-binding protein SMBP2 |
| yol108c | p98171 | RGC1 | RHO-GAP hematopoietic protein C1 | ykl135c | q10567 | ADTB1 | Beta-adaptin 1 |
| yol108c | p98171 | RGC1 | RHO-GAP hematopoietic proteir C1 | Ymr317w | q02817 | MUC2 | Intestinal mucin 2/mucin 2 |
| yol111c | p11441 | GDX | Ubiquitin-like protein GDX | yor007c | p50502 | HIP | Progesterone receptor-associated p48 protein |
| yol111c | p54725 | RAD23A | UV excision repair protein protein RAD23 homolog A/HHR23A | yor007c | p30260 | CDC27 | Protein CDC27HS/cell division cycle protein 27 homolog |
| yol111c | p54727 | D21090 | UV excision repair protein protein RAD23 homolog B/XP-C repair complementing protein (p58/HHR23B), complete cds. | yor007c | q08752 | PPID | 40 kD peptidyl-prolyl CIS-TRANS isomerase/cyclophilin-40 mRNA, complete cds. |
| yol123w | p07029 | UP2 | Heterogeneous nuclear ribonucleo-protein UP2 | ygl122c | p20226 | TBP | TATA-binding protein/transcription initiation factor TFIID |
| yol123w | p09651 | HNRPA1 | Heterogenous nuclear ribonucleo-protein A1/helix-destabilizing protein/single-strand binding protein/HNRNP core protein A1 | ygl122c | q10571 | MN1 | Probable tumor suppressor protein MN1 |
| yol123w | p11940 | PABPL1 | PolyA binding protein 1 | ygl122c | q14814 | MEF2D | Myocyte-specific enhancer factor 2D |
| yol123w | p22626 | HNRPA2B1 | Heterogeneous nuclear ribonucleo-proteins A2/B1 | ygl122c | p51531 | SMARCA2 | Possible global transcription activator SNF2L2/BRM |
| yol123w | p26378 | ELAVL4 | Paraneoplasticencephalomyelitis antigen 3 | ygl122c | FA2858 | HD | Huntingtin/huntington's disease protein |
| yol123w | p38159 | HNRPG | Heterogeneous nuclear ribonucleo-protein G/HNRNP G/glycoprotein P43 | ygl122c | q92794 | MOZ | Monocytic leukemia zinc finger protein |
| yol123w | q15427 | SAP49 | Spliceosome associated protein 49/ SAP49 | ygl122c | q93074 | KIAA0192 | Hypothetical protein KIAA0192 |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| yol130w | p46821 | MAP1B | Microtubule-associated protein 1B | ygl025c | q02078 | MEF2A | Myocyte-specific enhancer factor 2D |
| yol130w | q04724 | TLE1 | Transducin-like enhancer protein | ygl025c | q02817 | MUC2 | Intestinal mucin 2/mucin 2 |
| yol130w | p46821 | MAP1B | Microtubule-associated protein 1B | ylr291c | q14232 | ELF2B1 | Translation initiation factor eIF-2B alpha subunit |
| yol130w | q04724 | TLE1 | Transducin-like enhancer protein | ylr291c | p49770 | EIF2B2 | Translation initiation factor EIF-2B beta subunit/S20iii15 |
| yor061w | p24941 | CDK2 | Cell division protein kinase 2 | yor030w | p13862 | CSNK2B | Casein kinase II beta subunit |
| yor128c | p22234 | PAICS | ADE2 showing homologies to SAICAR synthetase and AIR carboxylase of the purine pathway | ycr066w | p35226 | BMI1 | DNA-binding protein BMI1 |
| yor128c | p22234 | PAICS | ADE2 showing homologies to SAICAR synthetase and AIR carboxylase of the purine pathway | ycr067c | p42568 | MLLT3 | AF-9 protein |
| yor128c | p22234 | PAICS | ADE2 showing homologies to SAICAR synthetase and AIR carboxylase of the purine pathway | yor128c | p22234 | PAICS | ADE2 showing homologies to SAICAR synthetase and AIR carboxylase of the purine pathway |
| yor132w | q00839 | HNRNPU | Heterogenous nuclear ribonucleoprotein U/scaffold attachment factor A | yor060w | q12840 | KIF5C | Neuronal kinesin heavy chain |
| yor269w | p25388 | GNB2-RS1 | Guanine nucleotide-binding protein beta subunit-like protein 12.3 | ylr254c | p49454 | CENPF | CENP-F kinetochore protein |
| yor260w | p35606 | COPP | Beta subunit of coatomer complex | ylr254c | q02224 | CENPE | Centromeric protein E/CENP-E protein |
| yor269w | p43034 | PAFAH1B1 | Platelet-activating factor acetyl-hydrolase IB alpha subunit | ylr254c | p13533 | MYH6 | Myosin heavy chain, cardiac muscle alpha isoform |
| yor303w | p31327 | CPS1 | Carbamoyl-phosphate synthase [ammonia], mitochondrial [precursor] | yor039w | p13862 | CSNK2B | Casein kinase II beta subunit |
| yor348c | p52569 | SLC7A2 | Low-affinity cationic amino acid transporter-2/CAT-2 | ycr045c | p29144 | TTP2 | Tripeptidyl-peptidase II |
| yor348c | p52569 | SLC7A2 | Low-affinity cationic amino acid transporter-2/CAT-2 | yjl084c | q03164 | MLL | Zinc finger protein HRX |
| yor348c | p52569 | SLC7A2 | Low-affinity cationic amino acid transporter-2/CAT-2 | Ymr228w | q01082 | SPTB2 | Beta-spectrin chain, brain |
| yor353c | p22792 | CPN2 | Carboxypeptidase N | ygr120c | p49454 | CENPF | CENP-F kinetochore protein |
| yor353c | p35858 | IGFALS | IGF binding protein complex acid-labile | ygr120c | p04114 | APOB | Apolipoprotein B |
| yor353c | q06828 | FMOD | Fibromodulin | ygr120c | p30622 | RSN | Restin |
| yor353c | p07585 | DCN | Bone proteoglycan II [precursor]/PG40 | yhr102w | q13177 | PAK2 | Serine/threonine-protein kinase PAK-gamma |
| yor353c | p22792 | CPN2 | Carboxypeptidase N | yhr102w | q02750 | PRKMK1 | Dual specificity mitogen-activated protein kinase kinase 1 |
| yor353c | p23515 | OMG | Oligodendrocyte-myelin glycoprotein | yhr102w | q13153 | PAK1 | Serine/threonine-protein kinase PAK-alpha |
| yor353c | p35858 | IGFALS | IGF binding protein complex acid-labile | yhr102w | q99759 | MAP3K3 | Mitogen-activated protein kinase kinase kinase 3/MEK kinase 3 |
| yor353c | q06828 | FMOD | Fibromodulin | yhr102w | p45985 | MAP2K4 | Dual specificity mitogen-activated protein kinase kinase 4 |
| yor353c | q14392 | GARP | Garp protein/Garpin | yhr102w | q13163 | MAP2K5 | Dual specificity mitogen-activated protein kinase kinase 5 |
| y0r353c | q99102 | MUC4 | Tracheo-bronchial mucin 4/mucin 4 [fragment] | yhr102w | p51955 | NEK2 | Serine/threonine-protein kinase NEK2 |
| yor362c | p25786 | PSMA1 | Proteasome subunit C2. | yfl017c | p08578 | SNRPE | Small nuclear ribonucleoprotein E/snRNP-E |
| yor375c | p00367 | GLUD1 | Glutamate dehydrogenase 1 | yjl124c | p14678 | SNRPB | Small nuclear ribonucleoprotein associated proteins B and B' |
| yor375c | p49448 | GLUD2 | Glutamate dehydrogenase 2 | yjl124c | p14648 | SNRPN | Small nuclear ribonucleoprotein associated protein N |
| ypl049c | p51825 | MLLT2 | AF-4 protein | ydr480w | p17931 | LGALS3 | Galectin-3/IgE-binding protein |
| ypl059w | p35754 | GLRX | Glutaredoxin. | yil105c | p20226 | TBP | TATA-binding protein/transcription initiation factor TFIID |
| ypl059w | p35754 | GLRX | Glutaredoxin. | ynl047c | q99418 | ARNO | ARF nucleotide-binding site opener/ARNO protein/ARF exchange factor |
| ypl140c | p45985 | MAP2K4 | Dual specificity mitogen-activated protein kinase kinase 4 | yhr030c | q15759 | MAPK11 | Mitogen-activated protein kinase 11 |
| ypl140c | p46734 | MAP2K3 | Dual specificity mitogen-activated protein kinase kinase 3/MAP kinase kinase 3 | yhr030c | p53778 | MAPK12 | Mitogen-activated protein kinase 12/ERK6/extracellular signal-regulated kinase 6 |
| ypl140c | p52564 | MAP2K6 | Dual specificity mitogen-activated protein kinas kinase 6 | yhr030c | p27361 | MAPK3 | Mitogen-activated protein kinase 3/extracellular signal-regulated kinase 1 |
| ypl140c | q02750 | PRKMK1 | Dual specificity mitogen-activated protein kinase kinase 1 | yhr030c | q13164 | MAPK7 | Mitogen-activated protein kinase 7/ERK5 |
| ypl140c | q13163 | MAP2KS | Dual specificity mitogen-activated protein kinase kinase 5 | yhr030c | q16539 | MAPK14 | Mitogen-activated protein kinase 14/CSBP |
| ypl140c | q99759 | MAP3K3 | Mitogen-activated protein kinase kinase kinase 3/MEK kinase 3 | yhr030c | p28482 | MAPK1 | Mitogen-activated protein kinase 1/extracellular signal-regulated kinase 2 |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ypl151c | p35606 | COPP | Beta subunit of coatomer complex | yor036w | q02224 | CENPE | Centromeric protein E/CENP-E protein |
| ypl151c | p43034 | PAFAH1B1 | Platelet-activating factor acetyl-hydrolase IB alpha subunit | yor036w | p49454 | CENPF | CENP-F kinetochore protein |
| ypl151c | q15542 | TAF2D | Transcription initiation factor TFIID 100 Kd subunit/TAFII-100/TAFII100 | yor036w | p35580 | MYH10 | Myosin heavy chain, nonmuscle type B/ cellular myosin heavy chain, type B/ NMMHC-B |
| ypl174c | p49454 | CENPF | CENP-F kinetochore protein | yhr129c | p42024 | ACTR1A | Alpha-centractin |
| ypl174c | q02224 | CENPE | Centromeric protein E/CENP-E protein | yhr129c | p42025 | ACTR1B | Beta-centractin |
| ypl174c | p11055 | MYH3 | Embryonic myosin heavy chain. | yil144w | p11055 | MYH3 | Embryonic myosin heavy chain. |
| ypl174c | p12882 | MYSS | Myosin heavy chain skeletal muscle, light meromyosin regl0n | yil144w | p30622 | RSN | Restin |
| ypl174c | p12883 | MYH7 | Myosin heavy chain, cardiac muscle beta isoform | yil144w | p12883 | MYH7 | Myosin heavy chain, cardiac muscle beta isoform |
| ypl174c | p13533 | MYH6 | Myosin heavy chain, cardiac muscle alpha isoform | yil144w | p13533 | MYH6 | Myosin heavy chain, cardiac muscle alpha isoform |
| ypl174c | p30622 | RSN | Restin | yil144w | p35579 | MYH9 | Myosin heavy chain, nonmuscle type A/ cellular myosin heavy chain, type A/ NMMHC-A |
| ypl174c | p35580 | MYH10 | Myosin heavy chain, nonmuscle type B/ cellular myosin heavy chain, type B/ NMMHC-B | yil144w | p13535 | MYH8 | Myosin heavy chain, perinatal skeletal muscle |
| ypl174c | p49454 | CENPF | CENP-F kinetochore protein | yil144w | p49454 | CENPF | CENP-F kinetochore protein |
| ypl174c | q02224 | CENPE | Centromeric protein E/CENP-E protein | yil144w | q02224 | CENPE | Centromeric protein E/CENP-E protein |
| ypl174c | q14203 | DCTN1 | Dynactin, 150 kD isoform [fragment] | yil144w | p15924 | DSP | Desmoplakin I and II |
| ypl174c | p11055 | MYH3 | Embryonic myosin heavy chain. | ylr423c | p12270 | TPR | Nucleoprotein TPR |
| ypl174c | p12882 | MYSS | Myosin heavy chain skeletal muscle, light meromyosin region | ylr423c | p11047 | LAMC1 | Laminin gamma-1 chain [precursor]/ laminin B2 chain |
| ypl174c | p12883 | MYH7 | Myosin heavy chain, cardiac muscle beta isoform | ylr423c | p30622 | RSN | Restin |
| ypl174c | p13533 | MYH6 | Myosin heavy chain, cardiac muscle alpha isoform | ylr423c | p13535 | MYH8 | Myosin heavy chain, perinatal skeletal muscle |
| ypl174c | p30622 | RSN | Restin | ylr423c | p05787 | KRT8 | Keratin, type II cytoskeletal 8/ cytokeratin 8/K8/CK8 |
| ypl174c | p35580 | MYH10 | Myosin heavy chain, nonmuscle type B/ cellular myosin heavy chain, type B/ NMMHC-B | ylr423c | q15431 | SYCP1 | Synaptonemal complex protein 1/SCP-1 protein |
| ypl174c | p49454 | CENPF | CENP-F kinetochore protein | ylr423c | p49454 | CENPF | CENP-F kinetochore protein |
| ypl174c | q02224 | CENPE | Centromeric protein E/CENP-E protein | ylr423c | q02224 | CENPE | Centromeric protein E/CENP-E protein |
| ypl174c | q14203 | DCTN1 | Dynactin, 150 kD isoform [fragment] | ylr423c | p15924 | DSP | Desmoplakin I and II |
| ypl259c | p53677 | P47B | Clathrin coat assembly protein AP47 homolog 2 | ykl135c | q10567 | ADTB1 | Beta-adaptin 1 |
| ypl259c | p53680 | CLAPS2 | Clathrin coat assembly protein AP17/ clathrin coat associated protein AP17 | ykl135c | p21851 | CLAPB1 | Beta adaptin |
| ypl260w | p12270 | TPR | Nucleoprotein TPR | yil144w | p12883 | MYH7 | Myosin heavy chain, cardiac muscle beta isoform |
| ypl260w | p17661 | DES | Desmin | yil144w | p30622 | RSN | Restin |
| ypl260w | p33176 | KNS1 | Kinesin heavy chain | yil144w | p15924 | DSP | Desmoplakin I and II |
| ypl260w | p49454 | CENPF | CENP-F kinetochore protein | yil144w | p49454 | CENPF | CENP-F kinetochore protein |
| ypl260w | q02224 | CENPE | Centromeric protein E/CENP-E protein | yil144w | q02224 | CENPE | Centromeric protein E/CENP-E protein |
| ypl260w | q15032 | KIAA0029 | Hypothetical protein KIAA0029 | yil144w | p13535 | MYH8 | Myosin heavy chain, perinatal skeletal muscle |
| ypl260w | q15431 | SYCP1 | Synaptonemal complex protein 1/SCP-1 protein | yil144w | p11055 | MYH3 | Embryonic myosin heavy chain. |
| ypl260w | q16787 | LAMA3 | Laminin alpha-3 chain | yil144w | p13533 | MYH6 | Myosin heavy chain, cardiac muscle alpha isoform |
| ypr018w | p35241 | RDX | Radixin | ybr195c | o00628 | PTS2R | Peroxisomal targeting signal 2 receptor |
| ypr018w | p35580 | MYH10 | Myosin heavy chain, nonmuscle type B/ cellular myosin heavy chain, type B/ NMMHC-B | ybr195c | p04901 | GNB1 | Guanine nucleotide-binding protein G(I)/G(S)/G(T) beta subunit 1 |
| ypr018w | p46821 | MAP1B | Microtubule-associated protein 1B | ybr195c | q09028 | RBAP48 | Chromatin assembly factor 1 P48 subunit/retinoblastoma binding protein P48 |
| ypr018w | q02832 | BLSA | B-lymphocyte antigen/B-lymphocyte surface antigen | ybr195c | p11016 | GNB2 | Guanine nucleotide-binding protein beta subunit 2 |
| ypr018w | q14203 | DCTN1 | Dynactin, 150 kD isoform [fragment] | ybr195c | q16576 | RBBP7 | Histone acetyl transferase type B subunit 2/retinoblastoma-binding protein |
| ypr018w | q16643 | DBN1 | Drebin E | ybr195c | p16520 | GNB3 | Guanine nucleotide-binding protein G(I)/G(S)/G(T) beta subunit 3 |
| ypr048w | p29475 | NOS1 | Nitric oxide synthase/neuronal NOS | yor355w | p42568 | MLLT3 | AF-9 protein |
| ypr048w | p35228 | NOS2 | Inducible nitric oxide synthase | y0r355w | q14669 | TRIP12 | Thyroid receptor interacting protein 12/ KIAA0045 |

TABLE 7-continued

Human ortholog protein interactions

| Yeast accno (bait) | Human ortholog accno | Human ortholog name | Human ortholog description | Yeast accno (prey) | Human ortholog accno | Human ortholog name | Human ortholog description |
|---|---|---|---|---|---|---|---|
| ypr054w | p28482 | MAPK1 | Mitogen-activated protein kinase 1/ extracellular signal-regulated kinase 2 | yfl029c | p24941 | CDK2 | Cell division protein kinase 2 |
| ypr054w | p53778 | MAPK12 | Mitogen-activated protein kinase 12/ERKB/extracellular signal-regulated kinase 6 | yfl029c | p50613 | CDK7 | Cell division protein kinase 7/CAK/ CDK-activating kinase |
| ypr054w | p53779 | MAPK10 | Mitogen-activated protein kinase 10 | yfl029c | p49540 | GSK3A | Glycogen synthase kinase-3 alpha |
| ypr054w | q13164 | MAPK7 | Mitogen-activated protein kinase 7/ ERKS | yfl029c | q00526 | CDK3 | Cell division protein kinase 3 |
| ypr054w | q15759 | MAPK11 | Mitogen-activated protein kinase 11 | yfl029c | p49841 | GSK3B | Glycogen synthase kinase-3 beta |
| ypr054w | q16539 | MAPK14 | Mitogen-activated protein kinase 14/ CSBP | yfl029c | q00535 | CDK5 | Cell division protein kinase 5/TAU protein kinase II catalytic subunit/TPKII catalytic subunit |
| ypr105c | p07197 | NEFM | Neurofilament triplet M protein/160 Kd neurofilament protein/NF-M | ygl14sw | p35749 | MYH11 | Myosin heavy chain, smooth muscle isoform/SMMHC [FRAGMENT] |
| ypr105c | p07197 | NEFM | Neurofilament triplet M protein/160 Kd neurofilament protein/NF-M | ygl153w | q03001 | BPAG1 | Bullous 230 kDa pemphigoid antigen 1 |
| ypr105c | p07197 | NEFM | Neurofilament triplet M protein/160 Kd neurofilament protein/NF-M | ygr120c | p04114 | APOB | Apolipoprotein B |
| ypr105c | p07197 | NEFM | Neurofilament triplet M protein/160 Kd neurofilament protein/NF-M | yhr060w | p25789 | PSMA4 | Proteasome subunit C9 |
| ypr110c | p19387 | POLR2C | DNA-directed RNA polymerase II 33Kd subunit/RPB33 | ylr238w | p49454 | CENPF | CENP-F kinetochore protein |
| ypr110c | p19387 | POLR2C | DNA-directed RNA polymerase II 33Kd subunit/RPB33 | ynl113w | q06481 | APLP2 | Amyloid-like protein 2/APPH/amyloid protein homolog |
| ypr119w | p14635 | CCNB1 | G2/mitotic-specific cyclin B1 | ybr135w | p33551 | CKS1 | Cyclin-dependent kinases regulatory subunit 1 |
| ypr119w | p20248 | CCNA | G2/mitotic-specific cyclin A. | ybr135w | p10275 | AR | Androgen receptor |
| ypr119w | p14635 | CCNB1 | G2/mitotic-specific cyclin B1 | ydr412w | p36777 | LONN | Lon protease-like protein |
| ypr119w | p20248 | CCNA | G2/mitotic-specific cyclin A. | ydr412w | p36776 | LONM | Mitochondrial LON protease homolog [precursor] |
| ypr119w | p14635 | CCNB1 | G2/mitotic-specific cyclin B1 | yhr035w | q15437 | SEC23B | Protein transprot protein Sec23 B isoform |
| ypr119w | p20248 | CCNA | G2/mitotic-specific cyclin A. | yhr035w | q15436 | SEC23A | Protein transprot protein Sec23 A isoform |
| ypr119w | p14635 | CCNB1 | G2/mitotic-specific cyclin B1 | ynl135c | q00688 | FKBP3 | Rapamycin-selective 25 Kd immuno-philin |
| ypr119w | p20248 | CCNA | G2/mitotic-specific cyclin A. | ynl135c | p26885 | FKBP2 | FK506-binding protein/FKBp-13 |
| ypr173c | q03527 | PSMC1 | 26S protease (54) regulatory subunit | ylr025w | p14314 | PRKCSH | Protein kinase C substrate, 80 kD protein, heavy chain/80K-H protein |
| ypr173c | q13608 | PEX6 | Peroxisome assembly factor-2/ peroxisomal-type ATPase 1 | ylr025w | q14203 | DCTN1 | Dynactin, 150 kD isoform [fragment] |
| ypr185w | p20226 | TBP | TATA-binding protein/transcription initiation factor TFIID | ygl180w | p22694 | PRKACB | Testis-specific cAMP-dependent protein kinase catalytic subunit C-beta isoform |
| ypr185w | p51531 | SMARCA2 | Possible global transcription activator SNF2L2/BRM | ygl180w | p17612 | PRKACA | cAMP-dependent protein kinase catalytic subunit type alpha |
| ypr185w | p54252 | MJD1 | Machado-joseph disease protein 1 | ygl180w | p54646 | PRKAA2 | 5'-AMP-activated protein kinase, catalytic alpha-2 chain |
| ypr185w | q10571 | MN1 | Probable tumor suppressor protein MN1 | ygl180w | q04759 | PRKCQ | Protein kinase C-theta type |
| ypr185w | q93074 | KIM0192 | Hypothetical protein KIAA0192 | ygl180w | p27448 | P78 | Putative serind/threonine-protein kinase P78 |
| ypr185w | p20226 | TBP | TATA-binding protein/transcription initiation factor TFIID | ygr120c | p30622 | RSN | Restin |
| ypr185w | p51531 | SMARCA2 | Possible global transcription activator SNF2L2/BRM | ygr120c | p49454 | CENPF | CENP-F kinetochore protein |
| ypr185w | p54252 | MJD1 | Machado-joseph disease protein 1 | ygr120c | p04114 | APOB | Apolipoprotein B |
| ypr185w | p20226 | TBP | TATA-binding protein/transcription initiation factor TFIID | ygr253c | p25788 | PSMA3 | Proteasome subunit C8 |
| ypr185w | p51531 | SMARCA2 | Possible global transcription activator SNF2L2/BRM | ygr253c | p25787 | PSMA2 | Proteasome subunit C3 |
| ypr185w | p54252 | MJD1 | Machado-joseph disease protein 1 | ygr253c | p25786 | PSMA1 | Proteasome subunit C2. |
| ypr185w | q10571 | MN1 | Probable tumor suppressor protein MN1 | ygr253c | p34062 | PSMA6 | Proteasome iota chain/PROS-27 |
| ypr185w | q93074 | KIAA0192 | Hypothetical protein KIAA0192 | ygr253c | p25789 | PSMA4 | Proteasome subunit C9 |
| ypr185w | p20226 | TBP | TATA-binding protein/transcription initiation factor TFIID | ylr423c | p15924 | DSP | Desmoplakin I and II |
| ypr185w | p51531 | SMARCA2 | Possible global transcription activator SNF2L2/BRM | ylr423c | p49454 | CENPF | CENP-F kinetochore protein |
| ypr185w | p54252 | MJD1 | Machado-joseph disease protein 1 | ylr423c | q02224 | CENPE | Centromeric protein E/CENP-E protein |
| ypr185w | q10571 | MN1 | Probable tumor suppressor protein MN1 | ylr423c | p30622 | RSN | Restin |
| ypr185w | q93074 | KIAA0192 | Hypothetical protein KIAA0192 | ylr423c | p13535 | MYH8 | Myosin heavy chain, perinatal skeletal muscle |

The human polypeptides disclosed in Table 7 are related as orthologs to yeast polypeptides that interact to form complexes according to the invention. Table 7 reflects this relationship and specifies a yeast accession number for a given human ortholog. In particular, Table 7 includes in column 1 the yeast accession number for the yeast "bait" sequence corresponding to the indicated human ortholog. Columns 2–4 provide the accession number of the human ortholog, the name of the human ortholog, and a description of the human ortholog, respectively, of the yeast "bait sequence". Column 5 of Table 7 provides the yeast accession number of the yeast "prey" sequence. Columns 6–8 provide the accession number of the human ortholog, the name of the human ortholog, and a description of the human ortholog, respectively, of the yeast "prey sequence".

The Yeast and Human Ortholog Accession Numbers (ACCNO) listed in Table 7 are shown with their corresponding Sequence Identification Numbers (SEQIDNO) in Table 8.

TABLE 8

| ACCNO | SEQIDNO |
|---|---|
| YAL016W | 1 |
| YAL032C | 2 |
| YAL034W-A | 3 |
| YAL036C | 4 |
| YAL040C | 5 |
| YAL049C | 6 |
| YAR003W | 7 |
| YAR014C | 8 |
| YAR031W | 9 |
| YAR033W | 10 |
| YAR066W | 11 |
| YBL007C | 12 |
| YBL010C | 13 |
| YBL014C | 14 |
| YBL021C | 15 |
| YBL025W | 16 |
| YBL042C | 17 |
| YBL043W | 18 |
| YBL051C | 19 |
| YBL078C | 20 |
| YBL101W-A | 21 |
| YBL102W | 22 |
| YBL105C | 23 |
| YBR006W | 24 |
| YBR040W | 25 |
| YBR052C | 26 |
| YBR055C | 27 |
| YBR057C | 28 |
| YBR059C | 29 |
| YBR077C | 30 |
| YBR094W | 31 |
| YBR103W | 32 |
| YBR108W | 33 |
| YBR125C | 34 |
| YBR133C | 35 |
| YBR134W | 36 |
| YBR135W | 37 |
| YBR14TC | 38 |
| YBR154C | 39 |
| YBR170C | 40 |
| YBR175W | 41 |
| YBR176W | 42 |
| YBR184W | 43 |
| YBR188C | 44 |
| YBR190W | 45 |
| YBR193C | 46 |
| YBR194W | 47 |
| YBR195C | 48 |
| YBR196C | 49 |
| YBR205W | 50 |
| YBR217W | 51 |
| YBR221C | 52 |
| YBR228W | 53 |
| YBR237W | 54 |
| YBR244W | 55 |
| YBR252W | 56 |
| YBR253W | 57 |
| YBR254C | 58 |
| YBR270C | 59 |
| YBR274W | 60 |
| YBR281C | 61 |
| YCL020W | 62 |
| YCL024W | 63 |
| YCL032W | 64 |
| YCL040W | 65 |
| YCL046W | 66 |
| YCL054W | 67 |
| YCL055W | 68 |
| YCL059C | 69 |
| YCR004C | 70 |
| YCR009C | 71 |
| YCR011C | 72 |
| YCR020C-A | 73 |
| YCR022C | 74 |
| YCR023C | 75 |
| YCR027C | 76 |
| YCR030C | 77 |
| YCR045C | 78 |
| YCR050C | 79 |
| YCR057C | 80 |
| YCR059C | 81 |
| YCR063W | 82 |
| YCR066W | 83 |
| YCR067C | 84 |
| YCR082W | 85 |
| YCR086W | 86 |
| YCR093W | 87 |
| YCR106W | 88 |
| YDL001W | 89 |
| YDL002C | 90 |
| YDL006W | 91 |
| YDL011C | 92 |
| YDL012C | 93 |
| YDL013W | 94 |
| YDL017W | 95 |
| YDL063C | 96 |
| YDL065C | 97 |
| YDL071C | 98 |
| YDL076C | 99 |
| YDL088C | 100 |
| YDL089W | 101 |
| YDL090C | 102 |
| YDL097C | 103 |
| YDL098C | 104 |
| YDL110C | 105 |
| YDL111C | 106 |
| YDL113C | 107 |
| YDL127W | 108 |
| YDL133W | 109 |
| YDL135C | 110 |
| YDL144C | 111 |
| YDL146W | 112 |
| YDL149W | 113 |
| YDL150W | 114 |
| YDL154W | 115 |
| YDL155W | 116 |
| YDL160C | 117 |
| YDL165W | 118 |
| YDL203C | 119 |
| YDL210W | 120 |
| YDL212W | 121 |
| YDL215C | 122 |
| YDL216C | 123 |
| YDL236W | 124 |
| YDL239C | 125 |
| YDL246C | 126 |
| YDR001C | 127 |
| YDR002W | 128 |
| YDR013W | 129 |
| YDR016C | 130 |

TABLE 8-continued

| ACCNO | SEQIDNO |
|---|---|
| YDR017C | 131 |
| YDR020C | 132 |
| YDR026C | 133 |
| YDR032C | 134 |
| YDR044W | 135 |
| YDR051C | 136 |
| YDR054C | 137 |
| YDR061W | 138 |
| YDR070C | 139 |
| YDR071C | 140 |
| YDR073W | 141 |
| YDR074W | 142 |
| YDR076W | 143 |
| YDR077W | 144 |
| YDR078C | 145 |
| YDR084C | 146 |
| YDR088C | 147 |
| YDR098C | 148 |
| YDR099W | 149 |
| YDR106W | 150 |
| YDR108W | 151 |
| YDR110W | 152 |
| YDR115W | 153 |
| YDR122W | 154 |
| YDR123C | 155 |
| YDR128W | 156 |
| YDR132C | 157 |
| YDR140W | 158 |
| YDR142C | 159 |
| YDR145W | 160 |
| YDR146C | 161 |
| YDR148C | 162 |
| YDR151C | 163 |
| YDR152W | 164 |
| YDR162C | 165 |
| YDR167W | 166 |
| YDR174W | 167 |
| YDR179C | 168 |
| YDR183W | 169 |
| YDR200C | 170 |
| YDR201W | 171 |
| YDR206W | 172 |
| YDR207C | 173 |
| YDR214W | 174 |
| YDR215C | 175 |
| YDR218C | 176 |
| YDR225W | 177 |
| YDR236C | 178 |
| YDR255C | 179 |
| YDR267C | 180 |
| YDR273W | 181 |
| YDR279W | 182 |
| YDR292C | 183 |
| YDR299W | 184 |
| YDR308C | 185 |
| YDR311W | 186 |
| YDR313C | 187 |
| YDR315C | 188 |
| YDR326C | 189 |
| YDR328C | 190 |
| YDR335W | 191 |
| YDR348C | 192 |
| YDR357C | 193 |
| YDR372C | 194 |
| YDR376W | 195 |
| YDR381W | 196 |
| YDR382W | 197 |
| YDR383C | 198 |
| YDR386W | 199 |
| YDR388W | 200 |
| YDR394W | 201 |
| YDR398W | 202 |
| YDR400W | 203 |
| YDR408C | 204 |
| YDR412W | 205 |
| YDR416W | 206 |
| YDR429C | 207 |
| YDR439W | 208 |
| YDR448W | 209 |
| YDR469W | 210 |
| YDR472W | 211 |
| YDR477W | 212 |
| YDR480W | 213 |
| YDR482C | 214 |
| YDR489W | 215 |
| YDR490C | 216 |
| YDR503C | 217 |
| YDR508C | 218 |
| YDR510W | 219 |
| YDR515W | 220 |
| YEL009C | 221 |
| YEL015W | 222 |
| YEL023C | 223 |
| YEL041W | 224 |
| YEL053C | 225 |
| YEL060C | 226 |
| YEL062W | 227 |
| YEL068C | 228 |
| YER007C-A | 229 |
| YER010C | 230 |
| YER016W | 231 |
| YER018C | 232 |
| YER019C-A | 233 |
| YER021W | 234 |
| YER023W | 235 |
| YER027C | 236 |
| YER046W | 237 |
| YER052C | 238 |
| YER059W | 239 |
| YER062C | 240 |
| YER063W | 241 |
| YER065C | 242 |
| YER079W | 243 |
| YER081W | 244 |
| YER082C | 245 |
| YER092W | 246 |
| YER095W | 247 |
| YER099C | 248 |
| YER102W | 249 |
| YER105C | 250 |
| YER106W | 251 |
| YER116C | 252 |
| YER126C | 253 |
| YER127W | 254 |
| YER131W | 255 |
| YER133W | 256 |
| YER144C | 257 |
| YER157W | 258 |
| YER174C | 259 |
| YER179W | 260 |
| YER180C | 261 |
| YER186C | 262 |
| YFL002W-A | 263 |
| YFL009W | 264 |
| YFL010C | 265 |
| YFL017C | 266 |
| YFL023W | 267 |
| YFL029C | 268 |
| YFL035C | 269 |
| YFL056C | 270 |
| YFL059W | 271 |
| YFL060C | 272 |
| YFL061W | 273 |
| YFR002W | 274 |
| YFR008W | 275 |
| YFR024C-A | 276 |
| YFR033C | 277 |
| YFR037C | 278 |
| YFR042W | 279 |
| YFR043C | 280 |
| YFR047C | 281 |
| YFR052W | 282 |
| YFR057W | 283 |
| YGL015C | 284 |

TABLE 8-continued

| ACCNO | SEQIDNO |
|---|---|
| YGL019W | 285 |
| YGL024W | 286 |
| YGL025C | 287 |
| YGL026C | 288 |
| YGL028C | 289 |
| YGL030W | 290 |
| YGL051W | 291 |
| YGL058W | 292 |
| YGL061C | 293 |
| YGL071W | 294 |
| YGL091C | 295 |
| YGL112C | 296 |
| YGL115W | 297 |
| YGL116W | 298 |
| YGL122C | 299 |
| YGL126W | 300 |
| YGL127C | 301 |
| YGL134W | 302 |
| YGL145W | 303 |
| YGL150C | 304 |
| YGL153W | 305 |
| YGL154C | 306 |
| YGL155W | 307 |
| YGL158W | 308 |
| YGL161C | 309 |
| YGL166W | 310 |
| YGL170C | 311 |
| YGL172W | 312 |
| YGL174W | 313 |
| YGL175C | 314 |
| YGL180W | 315 |
| YGL189C | 316 |
| YGL192W | 317 |
| YGL198W | 318 |
| YGL201C | 319 |
| YGL208W | 320 |
| YGL214W | 321 |
| YGL221C | 322 |
| YGL229C | 323 |
| YGL230C | 324 |
| YGL237C | 325 |
| YGL238W | 326 |
| YGL242C | 327 |
| YGL254W | 328 |
| YGR010W | 329 |
| YGR014W | 330 |
| YGR017W | 331 |
| YGR024C | 332 |
| YGR046W | 333 |
| YGR047C | 334 |
| YGR048W | 335 |
| YGR049W | 336 |
| YGR057C | 337 |
| YGR058W | 338 |
| YGR061C | 339 |
| YGR068C | 340 |
| YGR075C | 341 |
| YGR099W | 342 |
| YGR104C | 343 |
| YGR108W | 344 |
| YGR113W | 345 |
| YGR117C | 346 |
| YGR119C | 347 |
| YGR120C | 348 |
| YGR122W | 349 |
| YGR129W | 350 |
| YGR136W | 351 |
| YGR144W | 352 |
| YGR154C | 353 |
| YGR155W | 354 |
| YGR158C | 355 |
| YGR163W | 356 |
| YGR173W | 357 |
| YGR213C | 358 |
| YGR229C | 359 |
| YGR232W | 360 |
| YGR234W | 361 |

TABLE 8-continued

| ACCNO | SEQIDNO |
|---|---|
| YGR239C | 362 |
| YGR250C | 363 |
| YGR252W | 364 |
| YGR253C | 365 |
| YGR267C | 366 |
| YGR268C | 367 |
| YGR269W | 368 |
| YGR278W | 369 |
| YGR294W | 370 |
| YHL002W | 371 |
| YHL006C | 372 |
| YHL009C | 373 |
| YHL018W | 374 |
| YHL019C | 375 |
| YHL025W | 376 |
| YHL027W | 377 |
| YHL042W | 378 |
| YHL046C | 379 |
| YHR014W | 380 |
| YHR016C | 381 |
| YHR030C | 382 |
| YHR032W | 383 |
| YHR035W | 384 |
| YHR039C | 385 |
| YHR057C | 386 |
| YHR060W | 387 |
| YHR084W | 388 |
| YHR091C | 389 |
| YHR102W | 390 |
| YHR111W | 391 |
| YHR115C | 392 |
| YHR122W | 393 |
| YHR128W | 394 |
| YHR129C | 395 |
| YHR134W | 396 |
| YHR140W | 397 |
| YHR145C | 398 |
| YHR158C | 399 |
| YHR160C | 400 |
| YHR170W | 401 |
| YHR171W | 402 |
| YHR184W | 403 |
| YHR185C | 404 |
| YHR187W | 405 |
| YHR193C | 406 |
| YHR204W | 407 |
| YHR207C | 408 |
| YHR215W | 409 |
| YIL007C | 410 |
| YIL008W | 411 |
| YIL011W | 412 |
| YIL013C | 413 |
| YIL033C | 414 |
| YIL065C | 415 |
| YIL074C | 416 |
| YIL082W | 417 |
| YIL105C | 418 |
| YIL112W | 419 |
| YIL132C | 420 |
| YIL144W | 421 |
| YIL150C | 422 |
| YIL151C | 423 |
| YIL160C | 424 |
| YIL163C | 425 |
| YIL172C | 426 |
| YIR001C | 427 |
| YIR005W | 428 |
| YIR018W | 429 |
| YIR024C | 430 |
| YIR032C | 431 |
| YIR037W | 432 |
| YIR044C | 433 |
| YJL001W | 434 |
| YJL013C | 435 |
| YJL025W | 436 |
| YJL030W | 437 |
| YJL036W | 438 |

TABLE 8-continued

| ACCNO | SEQIDNO |
|---|---|
| YJL041W | 439 |
| YJL048C | 440 |
| YJL056C | 441 |
| YJL057C | 442 |
| YJL064W | 443 |
| YJL065C | 444 |
| YJL084C | 445 |
| YJL088W | 446 |
| YJL092W | 447 |
| YJL110C | 448 |
| YJL112W | 449 |
| YJL124C | 450 |
| YJL137C | 451 |
| YJL154C | 452 |
| YJL160C | 453 |
| YJL162C | 454 |
| YJL178C | 455 |
| YJL184W | 456 |
| YJL185C | 457 |
| YJL211C | 458 |
| YJL218W | 459 |
| YJR009C | 460 |
| YJR024C | 461 |
| YJR034W | 462 |
| YJR049C | 463 |
| YJR050W | 464 |
| YJR072C | 465 |
| YJR074W | 466 |
| YJR076C | 467 |
| YJR086W | 468 |
| YJR091C | 469 |
| YJR093C | 470 |
| YJR094C | 471 |
| YJR117W | 472 |
| YJR122W | 473 |
| YJR125C | 474 |
| YJR133W | 475 |
| YJR135C | 476 |
| YJR136C | 477 |
| YJR159W | 478 |
| YKL001C | 479 |
| YKL002W | 480 |
| YKL012W | 481 |
| YKL015W | 482 |
| YKL017C | 483 |
| YKL019W | 484 |
| YKL023W | 485 |
| YKL028W | 486 |
| YKL033W | 487 |
| YKL039W | 488 |
| YKL052C | 489 |
| YKL061W | 490 |
| YKL067W | 491 |
| YKL070W | 492 |
| YKL075C | 493 |
| YKL090W | 494 |
| YKL103C | 495 |
| YKL110C | 496 |
| YKL130C | 497 |
| YKL135C | 498 |
| YKL142W | 499 |
| YKL144C | 500 |
| YKL166C | 501 |
| YKL183W | 502 |
| YKL204W | 503 |
| YKR007W | 504 |
| YKR011C | 505 |
| YKR022C | 506 |
| YKR024C | 507 |
| YKR025W | 508 |
| YKR026C | 509 |
| YKR037C | 510 |
| YKR048C | 511 |
| YKR055W | 512 |
| YKR060W | 513 |
| YKR062W | 514 |
| YKR068C | 515 |

TABLE 8-continued

| ACCNO | SEQIDNO |
|---|---|
| YKR083C | 516 |
| YKR096W | 517 |
| YKR099W | 518 |
| YKR104W | 519 |
| YLL001W | 520 |
| YLL027W | 521 |
| YLL028W | 522 |
| YLL032C | 523 |
| YLL046C | 524 |
| YLL049W | 525 |
| YLL057C | 526 |
| YLL062C | 527 |
| YLR015W | 528 |
| YLR025W | 529 |
| YLR046C | 530 |
| YLR049C | 531 |
| YLR065C | 532 |
| YLR071C | 533 |
| YLR072W | 534 |
| YLR082C | 535 |
| YLR098C | 536 |
| YLR102C | 537 |
| YLR113W | 538 |
| YLR117C | 539 |
| YLR121C | 540 |
| YLR135W | 541 |
| YLR150W | 542 |
| YLR154C | 543 |
| YLR190W | 544 |
| YLR200W | 545 |
| YLR208W | 546 |
| YLR215C | 547 |
| YLR216C | 548 |
| YLR229C | 549 |
| YLR238W | 550 |
| YLR243W | 551 |
| YLR245C | 552 |
| YLR254C | 553 |
| YLR258W | 554 |
| YLR264W | 555 |
| YLR270W | 556 |
| YLR275W | 557 |
| YLR284C | 558 |
| YLR288C | 559 |
| YLR291C | 560 |
| YLR293C | 561 |
| YLR294C | 562 |
| YLR303W | 563 |
| YLR305C | 564 |
| YLR312C | 565 |
| YLR315W | 566 |
| YLR319C | 567 |
| YLR321C | 568 |
| YLR322W | 569 |
| YLR323C | 570 |
| YLR324W | 571 |
| YLR328W | 572 |
| YLR345W | 573 |
| YLR352W | 574 |
| YLR362W | 575 |
| YLR376C | 576 |
| YLR386W | 577 |
| YLR390W | 578 |
| YLR392C | 579 |
| YLR403W | 580 |
| YLR417W | 581 |
| YLR424W | 582 |
| YLR429W | 583 |
| YLR432W | 584 |
| YLR433C | 585 |
| YLR435W | 586 |
| YLR438W | 587 |
| YLR447C | 588 |
| YLR465C | 589 |
| YLR466W | 590 |
| YML006C | 591 |
| YML015C | 592 |

TABLE 8-continued

| ACCNO | SEQIDNO |
|---|---|
| YML028W | 593 |
| YML031W | 594 |
| YML032C-A | 595 |
| YML035C | 596 |
| YML053C | 597 |
| YML068W | 598 |
| YML088W | 599 |
| YML094W | 600 |
| YML099C | 601 |
| YML109W | 602 |
| YML114C | 603 |
| YML119W | 604 |
| YML121W | 605 |
| YMR004W | 606 |
| YMR025W | 607 |
| YMR039C | 608 |
| YMR052W | 609 |
| YMR068W | 610 |
| YMR075C-A | 611 |
| YMR077C | 612 |
| YMR079W | 613 |
| YMR091C | 614 |
| YMR092C | 615 |
| YMR093W | 616 |
| YMR095C | 617 |
| YMR096W | 618 |
| YMR102C | 619 |
| YMR112C | 620 |
| YMR117C | 621 |
| YMR129W | 622 |
| YMR139W | 623 |
| YMR153W | 624 |
| YMR159C | 625 |
| YMR163C | 626 |
| YMR165C | 627 |
| YMR180C | 628 |
| YMR181C | 629 |
| YMR201C | 630 |
| YMR210W | 631 |
| YMR224C | 632 |
| YMR226C | 633 |
| YMR228W | 634 |
| YMR233W | 635 |
| YMR236W | 636 |
| YMR243C | 637 |
| YMR255W | 638 |
| YMR267W | 639 |
| YMR269W | 640 |
| YMR270C | 641 |
| YMR295C | 642 |
| YMR309C | 643 |
| YMR312W | 644 |
| YMR314W | 645 |
| YMR316C-B | 646 |
| YMR317W | 647 |
| YMR322C | 648 |
| YNL021W | 649 |
| YNL023C | 650 |
| YNL025C | 651 |
| YNL032W | 652 |
| YNL042W | 653 |
| YNL047C | 654 |
| YNL056W | 655 |
| YNL078W | 656 |
| YNL086W | 657 |
| YNL091W | 658 |
| YNL093W | 659 |
| YNL094W | 660 |
| YNL099C | 661 |
| YNL104C | 662 |
| YNL113W | 663 |
| YNL118C | 664 |
| YNL122C | 665 |
| YNL127W | 666 |
| YNL135C | 667 |
| YNL154C | 668 |
| YNL155W | 669 |
| YNL164C | 670 |
| YNL171C | 671 |
| YNL189W | 672 |
| YNL199C | 673 |
| YNL201C | 674 |
| YNL210W | 675 |
| YNL218W | 676 |
| YNL229C | 677 |
| YNL233W | 678 |
| YNL236W | 679 |
| YNL244C | 680 |
| YNL279W | 681 |
| YNL287W | 682 |
| YNL288W | 683 |
| YNL311C | 684 |
| YNL314W | 685 |
| YNL333W | 686 |
| YNR004W | 687 |
| YNR005C | 688 |
| YNR006W | 689 |
| YNR007C | 690 |
| YNR010W | 691 |
| YNR012W | 692 |
| YNR022C | 693 |
| YNR025C | 694 |
| YNR029C | 695 |
| YNR048W | 696 |
| YNR052C | 697 |
| YNR068C | 698 |
| YNR069C | 699 |
| YOL006C | 700 |
| YOL034W | 701 |
| YOL036W | 702 |
| YOL058W | 703 |
| YOL059W | 704 |
| YOL061W | 705 |
| YOL069W | 706 |
| YOL070C | 707 |
| YOL082W | 708 |
| YOL083W | 709 |
| YOL088C | 710 |
| YOL091W | 711 |
| YOL105C | 712 |
| YOL106W | 713 |
| YOL108C | 714 |
| YOL111C | 715 |
| YOL123W | 716 |
| YOL130W | 717 |
| YOL135C | 718 |
| YOL139C | 719 |
| YOL143C | 720 |
| YOL149W | 721 |
| YOR006C | 722 |
| YOR007C | 723 |
| YOR023C | 724 |
| YOR025W | 725 |
| YOR026W | 726 |
| YOR036W | 727 |
| YOR039W | 728 |
| YOR047C | 729 |
| YOR061W | 730 |
| YOR062C | 731 |
| YOR069W | 732 |
| YOR078W | 733 |
| YOR111W | 734 |
| YOR115C | 735 |
| YOR127W | 736 |
| YOR128C | 737 |
| YOR132W | 738 |
| YOR138C | 739 |
| YOR159C | 740 |
| YOR161C | 741 |
| YOR164C | 742 |
| YOR174W | 743 |
| YOR180C | 744 |
| YOR185C | 745 |
| YOR197W | 746 |

TABLE 8-continued

| ACCNO | SEQIDNO |
|---|---|
| YOR202W | 747 |
| YOR210W | 748 |
| YOR212W | 749 |
| YOR215C | 750 |
| YOR220W | 751 |
| YOR226C | 752 |
| YOR262W | 753 |
| YOR264W | 754 |
| YOR269W | 755 |
| YOR276W | 756 |
| YOR284W | 757 |
| YOR303W | 758 |
| YOR331C | 759 |
| YOR348C | 760 |
| YOR353C | 761 |
| YOR355W | 762 |
| YOR358W | 763 |
| YOR362C | 764 |
| YOR368W | 765 |
| YOR372C | 766 |
| YOR375C | 767 |
| YPL002C | 768 |
| YPL003W | 769 |
| YPL019C | 770 |
| YPL031C | 771 |
| YPL039W | 772 |
| YPL049C | 773 |
| YPL059W | 774 |
| YPL070W | 775 |
| YPL088W | 776 |
| YPL110C | 777 |
| YPL111W | 778 |
| YPL128C | 779 |
| YPL131W | 780 |
| YPL133C | 781 |
| YPL140C | 782 |
| YPL149W | 783 |
| YPL151C | 784 |
| YPL157W | 785 |
| YPL161C | 786 |
| YPL174C | 787 |
| YPL175W | 788 |
| YPL192C | 789 |
| YPL201C | 790 |
| YPL204W | 791 |
| YPL211W | 792 |
| YPL214C | 793 |
| YPL222W | 794 |
| YPL229W | 795 |
| YPL259C | 796 |
| YPL260W | 797 |
| YPR018W | 798 |
| YPR020W | 799 |
| YPR040W | 800 |
| YPR046W | 801 |
| YPR048W | 802 |
| YPR051W | 803 |
| YPR054W | 804 |
| YPR062W | 805 |
| YPR066W | 806 |
| YPR070W | 807 |
| YPR082C | 808 |
| YPR105C | 809 |
| YPR107C | 810 |
| YPR110C | 811 |
| YPR115W | 812 |
| YPR119W | 813 |
| YPR152C | 814 |
| YPR159W | 815 |
| YPR173C | 816 |
| YPR182W | 817 |
| YPR185W | 818 |
| O00505 | 819 |
| O00507 | 820 |
| O00628 | 821 |
| O00629 | 822 |
| O00746 | 823 |

TABLE 8-continued

| ACCNO | SEQIDNO |
|---|---|
| O14647 | 824 |
| O14727 | 825 |
| O15016 | 826 |
| O15355 | 827 |
| O15379 | 828 |
| O15541 | 829 |
| O43236 | 830 |
| P00352 | 831 |
| P00367 | 832 |
| P00480 | 833 |
| P00519 | 834 |
| P00966 | 835 |
| P02261 | 836 |
| P02533 | 837 |
| P02545 | 838 |
| P02546 | 839 |
| P02812 | 840 |
| P04062 | 841 |
| P04114 | 842 |
| P04181 | 843 |
| P04264 | 844 |
| P04280 | 845 |
| P04645 | 846 |
| P04765 | 847 |
| P04901 | 848 |
| P04908 | 849 |
| P05089 | 850 |
| P05091 | 851 |
| P05092 | 852 |
| P05127 | 853 |
| P05323 | 854 |
| P05387 | 855 |
| P05412 | 856 |
| P05423 | 857 |
| P05787 | 858 |
| P06241 | 859 |
| P06468 | 860 |
| P06748 | 861 |
| P07029 | 862 |
| P07197 | 863 |
| P07199 | 864 |
| P07203 | 865 |
| P07332 | 866 |
| P07384 | 867 |
| P07585 | 868 |
| P07942 | 869 |
| P07947 | 870 |
| P07951 | 871 |
| P08047 | 872 |
| P08129 | 873 |
| P08151 | 874 |
| P08578 | 875 |
| P08621 | 876 |
| P08670 | 877 |
| P08865 | 878 |
| P08910 | 879 |
| P09058 | 880 |
| P09110 | 881 |
| P09329 | 882 |
| P09429 | 883 |
| P09651 | 884 |
| P09769 | 885 |
| P10070 | 886 |
| P10071 | 887 |
| P10161 | 888 |
| P10162 | 889 |
| P10163 | 890 |
| P10242 | 891 |
| P10243 | 892 |
| P10244 | 893 |
| P10265 | 894 |
| P10275 | 895 |
| P10451 | 896 |
| P10515 | 897 |
| P10644 | 898 |
| P11016 | 899 |
| P11047 | 900 |

TABLE 8-continued

| ACCNO | SEQIDNO |
|---|---|
| P11055 | 901 |
| P11082 | 902 |
| P11161 | 903 |
| P11177 | 904 |
| P11182 | 905 |
| P11387 | 906 |
| P11441 | 907 |
| P11766 | 908 |
| P11908 | 909 |
| P11940 | 910 |
| P12036 | 911 |
| P12079 | 912 |
| P12268 | 913 |
| P12270 | 914 |
| P12882 | 915 |
| P12883 | 916 |
| P13533 | 917 |
| P13535 | 918 |
| P13645 | 919 |
| P13667 | 920 |
| P13807 | 921 |
| P13861 | 922 |
| P13862 | 923 |
| P14061 | 924 |
| P14314 | 925 |
| P14317 | 926 |
| P14619 | 927 |
| P14635 | 928 |
| P14648 | 929 |
| P14678 | 930 |
| P15428 | 931 |
| P15498 | 932 |
| P15531 | 933 |
| P15735 | 934 |
| P15918 | 935 |
| P15924 | 936 |
| P16104 | 937 |
| P16118 | 938 |
| P16333 | 939 |
| P16520 | 940 |
| P16591 | 941 |
| P17032 | 942 |
| P17252 | 943 |
| P17480 | 944 |
| P17600 | 945 |
| P17612 | 946 |
| P17655 | 947 |
| P17661 | 948 |
| P17677 | 949 |
| P17861 | 950 |
| P17931 | 951 |
| P17980 | 952 |
| P18146 | 953 |
| P18283 | 954 |
| P18583 | 955 |
| P19174 | 956 |
| P19338 | 957 |
| P19387 | 958 |
| P19388 | 959 |
| P19544 | 960 |
| P19784 | 961 |
| P19678 | 962 |
| P20172 | 963 |
| P20226 | 964 |
| P20248 | 965 |
| P20265 | 966 |
| P20309 | 967 |
| P20585 | 968 |
| P20591 | 969 |
| P20592 | 970 |
| P20749 | 971 |
| P20807 | 972 |
| P20839 | 973 |
| P21108 | 974 |
| P21181 | 975 |
| P21439 | 976 |
| P21695 | 977 |
| P21815 | 978 |
| P21817 | 979 |
| P21851 | 980 |
| P21953 | 981 |
| P22102 | 982 |
| P22234 | 983 |
| P22307 | 984 |
| P22314 | 985 |
| P22352 | 986 |
| P22392 | 987 |
| P22570 | 988 |
| P22626 | 989 |
| P22670 | 990 |
| P22694 | 991 |
| P22792 | 992 |
| P23246 | 993 |
| P23284 | 994 |
| P23327 | 995 |
| P23443 | 996 |
| P23490 | 997 |
| P23511 | 998 |
| P23515 | 999 |
| P23567 | 1000 |
| P23769 | 1001 |
| P23771 | 1002 |
| P24723 | 1003 |
| P24752 | 1004 |
| P24928 | 1005 |
| P24941 | 1006 |
| P25054 | 1007 |
| P25208 | 1008 |
| P25388 | 1009 |
| P25763 | 1010 |
| P25786 | 1011 |
| P25787 | 1012 |
| P25788 | 1013 |
| P25789 | 1014 |
| P26196 | 1015 |
| P26358 | 1016 |
| P26378 | 1017 |
| P26583 | 1018 |
| P26651 | 1019 |
| P26885 | 1020 |
| P27361 | 1021 |
| P27448 | 1022 |
| P27797 | 1023 |
| P27824 | 1024 |
| P28001 | 1025 |
| P28160 | 1026 |
| P28370 | 1027 |
| P28482 | 1028 |
| P28676 | 1029 |
| P29084 | 1030 |
| P29144 | 1031 |
| P29354 | 1032 |
| P29375 | 1033 |
| P29475 | 1034 |
| P29558 | 1035 |
| P29590 | 1036 |
| P29591 | 1036 |
| P29592 | 1036 |
| P29593 | 1036 |
| P29973 | 1037 |
| P30041 | 1038 |
| P30048 | 1039 |
| P30153 | 1040 |
| P30260 | 1041 |
| P30405 | 1042 |
| P30414 | 1043 |
| P30622 | 1044 |
| P30626 | 1045 |
| P30793 | 1046 |
| P30837 | 1047 |
| P31146 | 1048 |
| P31321 | 1049 |
| P31323 | 1050 |
| P31327 | 1051 |

TABLE 8-continued

| ACCNO | SEQIDNO |
|---|---|
| P31689 | 1052 |
| P31749 | 1053 |
| P31751 | 1054 |
| P32119 | 1055 |
| P32320 | 1056 |
| P32322 | 1057 |
| P32780 | 1058 |
| P32929 | 1059 |
| P33176 | 1060 |
| P33240 | 1061 |
| P33316 | 1062 |
| P33551 | 1063 |
| P33908 | 1064 |
| P34062 | 1065 |
| P34991 | 1066 |
| P35222 | 1067 |
| P35226 | 1068 |
| P35227 | 1069 |
| P35228 | 1070 |
| P35241 | 1071 |
| P35249 | 1072 |
| P35250 | 1073 |
| P35251 | 1074 |
| P35520 | 1075 |
| P35555 | 1076 |
| P35579 | 1077 |
| P35580 | 1078 |
| P35606 | 1079 |
| P35637 | 1080 |
| P35658 | 1081 |
| P35659 | 1082 |
| P35663 | 1083 |
| P35749 | 1084 |
| P35754 | 1085 |
| P35813 | 1086 |
| P35858 | 1087 |
| P35998 | 1088 |
| P36402 | 1089 |
| P36551 | 1090 |
| P36776 | 1091 |
| P36777 | 1092 |
| P36873 | 1093 |
| P36969 | 1094 |
| P37140 | 1095 |
| P37198 | 1096 |
| P38159 | 1097 |
| P38398 | 1098 |
| P38919 | 1099 |
| P38935 | 1100 |
| P39687 | 1101 |
| P39880 | 1102 |
| P40937 | 1103 |
| P41182 | 1104 |
| P41223 | 1105 |
| P41226 | 1106 |
| P41240 | 1107 |
| P41567 | 1108 |
| P42024 | 1109 |
| P42025 | 1110 |
| P42336 | 1111 |
| P42345 | 1112 |
| P42566 | 1113 |
| P42568 | 1114 |
| P42655 | 1115 |
| P42765 | 1116 |
| P42773 | 1117 |
| P42858 | 1118 |
| P43034 | 1119 |
| P43246 | 1120 |
| P43487 | 1121 |
| P43686 | 1122 |
| P43694 | 1123 |
| P45379 | 1124 |
| P45844 | 1125 |
| P45877 | 1126 |
| P45974 | 1127 |
| P45984 | 1128 |
| P45985 | 1129 |
| P46060 | 1130 |
| P46100 | 1131 |
| P46108 | 1132 |
| P46109 | 1133 |
| P46734 | 1134 |
| P46821 | 1135 |
| P46939 | 1136 |
| P46976 | 1137 |
| P47210 | 1138 |
| P47895 | 1139 |
| P47974 | 1140 |
| P47986 | 1141 |
| P48634 | 1142 |
| P48681 | 1143 |
| P48729 | 1144 |
| P48730 | 1145 |
| P49137 | 1146 |
| P49189 | 1147 |
| P49321 | 1148 |
| P49354 | 1149 |
| P49356 | 1150 |
| P49368 | 1151 |
| P49418 | 1152 |
| P49448 | 1153 |
| P49454 | 1154 |
| P49459 | 1155 |
| P49593 | 1156 |
| P49674 | 1157 |
| P49736 | 1158 |
| P49770 | 1159 |
| P49790 | 1160 |
| P49792 | 1161 |
| P49840 | 1162 |
| P49841 | 1163 |
| P49848 | 1164 |
| P49959 | 1165 |
| P50502 | 1166 |
| P50550 | 1167 |
| P50570 | 1168 |
| P50613 | 1169 |
| P51451 | 1170 |
| P51531 | 1171 |
| P51532 | 1172 |
| P51649 | 1173 |
| P51668 | 1174 |
| P51669 | 1175 |
| P51784 | 1176 |
| P51786 | 1177 |
| P51812 | 1178 |
| P51825 | 1179 |
| P51854 | 1180 |
| P51955 | 1181 |
| P51956 | 1182 |
| P51957 | 1183 |
| P51965 | 1184 |
| P52292 | 1185 |
| P52294 | 1186 |
| P52564 | 1187 |
| P52565 | 1188 |
| P52566 | 1189 |
| P52569 | 1190 |
| P52655 | 1191 |
| P52701 | 1192 |
| P52736 | 1193 |
| P52740 | 1194 |
| P52742 | 1195 |
| P52745 | 1386 |
| P52756 | 1196 |
| P52948 | 1197 |
| P53355 | 1198 |
| P53609 | 1199 |
| P53621 | 1200 |
| P53677 | 1201 |
| P53680 | 1202 |
| P53778 | 1203 |
| P53779 | 1204 |

TABLE 8-continued

| ACCNO | SEQIDNO |
|---|---|
| P53803 | 1205 |
| P54136 | 1206 |
| P54252 | 1207 |
| P54253 | 1208 |
| P54259 | 1209 |
| P54578 | 1210 |
| P54619 | 1211 |
| P54646 | 1212 |
| P54725 | 1213 |
| P54727 | 1214 |
| P54840 | 1215 |
| P55081 | 1216 |
| P55084 | 1217 |
| P55209 | 1218 |
| P55273 | 1219 |
| P55854 | 1220 |
| P55855 | 1221 |
| P56524 | 1222 |
| P56545 | 1223 |
| P56554 | 1224 |
| P78368 | 1225 |
| P78406 | 1226 |
| P78540 | 1227 |
| P80095 | 1228 |
| P80303 | 1229 |
| P98171 | 1230 |
| P98174 | 1231 |
| P98175 | 1232 |
| P98179 | 1233 |
| Q00059 | 1234 |
| Q00341 | 1235 |
| Q00526 | 1236 |
| Q00534 | 1237 |
| Q00535 | 1238 |
| Q00536 | 1239 |
| Q00688 | 1240 |
| Q00755 | 1036 |
| Q00796 | 1241 |
| Q00839 | 1242 |
| Q01082 | 1243 |
| Q01085 | 1244 |
| Q01105 | 1245 |
| Q01484 | 1246 |
| Q01485 | 1246 |
| Q01534 | 1247 |
| Q01658 | 1248 |
| Q01826 | 1249 |
| Q01844 | 1250 |
| Q02078 | 1251 |
| Q02224 | 1252 |
| Q02338 | 1253 |
| Q02446 | 1254 |
| Q02505 | 1255 |
| Q02547 | 1256 |
| Q02750 | 1257 |
| Q02817 | 1258 |
| Q02832 | 1259 |
| Q03001 | 1260 |
| Q03111 | 1261 |
| Q03164 | 1262 |
| Q03468 | 1263 |
| Q03527 | 1264 |
| Q04724 | 1265 |
| Q04759 | 1266 |
| Q05048 | 1267 |
| Q05193 | 1268 |
| Q05215 | 1269 |
| Q05516 | 1270 |
| Q05682 | 1271 |
| Q06481 | 1272 |
| Q06547 | 1273 |
| Q06609 | 1274 |
| Q06722 | 1387 |
| Q06730 | 1275 |
| Q06828 | 1276 |
| Q06830 | 1277 |
| Q06889 | 1278 |
| Q06945 | 1279 |
| Q07283 | 1280 |
| Q07352 | 1281 |
| Q08170 | 1282 |
| Q08209 | 1283 |
| Q08378 | 1284 |
| Q08379 | 1285 |
| Q08752 | 1286 |
| Q08945 | 1287 |
| Q09028 | 1288 |
| Q09472 | 1289 |
| Q10567 | 1290 |
| Q10571 | 1291 |
| Q12788 | 1292 |
| Q12840 | 1293 |
| Q12962 | 1294 |
| Q13098 | 1295 |
| Q13131 | 1296 |
| Q13153 | 1297 |
| Q13162 | 1298 |
| Q13163 | 1299 |
| Q13164 | 1300 |
| Q13177 | 1301 |
| Q13190 | 1302 |
| Q13216 | 1303 |
| Q13360 | 1304 |
| Q13363 | 1305 |
| Q13416 | 1306 |
| Q13438 | 1307 |
| Q13547 | 1308 |
| Q13573 | 1309 |
| Q13608 | 1310 |
| Q13610 | 1311 |
| Q13813 | 1312 |
| Q13838 | 1313 |
| Q14012 | 1314 |
| Q14028 | 1315 |
| Q14093 | 1316 |
| Q14141 | 1317 |
| Q14154 | 1318 |
| Q14156 | 1319 |
| Q14157 | 1320 |
| Q14203 | 1321 |
| Q14232 | 1322 |
| Q14240 | 1323 |
| Q14247 | 1324 |
| Q14392 | 1325 |
| Q14565 | 1326 |
| Q14669 | 1327 |
| Q14687 | 1328 |
| Q14690 | 1329 |
| Q14814 | 1330 |
| Q15019 | 1331 |
| Q15032 | 1332 |
| Q15036 | 1333 |
| Q15072 | 1334 |
| Q15181 | 1335 |
| Q15269 | 1336 |
| Q15274 | 1337 |
| Q15427 | 1338 |
| Q15431 | 1339 |
| Q15436 | 1340 |
| Q15437 | 1341 |
| Q15542 | 1342 |
| Q15544 | 1343 |
| Q15545 | 1344 |
| O15696 | 1345 |
| Q15759 | 1346 |
| Q15811 | 1347 |
| Q15831 | 1348 |
| Q16134 | 1349 |
| Q16181 | 1350 |
| Q16281 | 1351 |
| Q16539 | 1352 |
| Q16566 | 1353 |
| Q16576 | 1354 |
| Q16594 | 1355 |

TABLE 8-continued

| ACCNO | SEQIDNO |
|---|---|
| Q16600 | 1356 |
| Q16643 | 1357 |
| Q16781 | 1358 |
| Q16787 | 1359 |
| Q16816 | 1360 |
| Q16875 | 1361 |
| Q16877 | 1362 |
| Q92524 | 1363 |
| Q92636 | 1364 |
| Q92696 | 1365 |
| Q92764 | 1366 |
| Q92769 | 1367 |
| Q92781 | 1368 |
| Q92785 | 1369 |
| Q92793 | 1370 |
| Q92794 | 1371 |
| Q92908 | 1372 |
| Q92995 | 1373 |
| Q93008 | 1374 |
| Q93009 | 1375 |
| Q93068 | 1376 |
| Q93074 | 1377 |
| Q99102 | 1378 |
| Q99217 | 1379 |
| Q99418 | 1380 |
| Q99457 | 1381 |
| Q99462 | 1382 |
| Q99471 | 1383 |
| Q99733 | 1384 |
| Q99759 | 1385 |

In certain embodiments, one of the ortholog polypeptides includes a "bait" polypeptide selected from the polypeptides recited in Table 7, column 2, and the other ortholog polypeptide includes a "prey" protein selected from the polypeptides recited in Table 7, column 6. The yeast orthologs of these proteins are set out in columns 1 and 4 of Table 7, respectively. In some embodiments the first and second polypeptides of the complex are the polypeptides enumerated in Table 7. In some embodiments a first polypeptide is a "bait" polypeptide and a second polypeptide is "target" polypeptide, while in other embodiments the first polypeptide is a "target" polypeptide and the second is a "bait" polypeptide. Conservative variants of either polypeptide which retain binding specificity are within the scope of the invention, as are labeled forms of the complexes, as described above.

In other embodiments, the polypeptides are the binding domains of the "bait" and "prey" polypeptides listed in Table 7. A binding domain of a given first polypeptide may be any number of amino acids sufficient to specifically bind to, and complex with, the corresponding second polypeptide under conditions suitable for complex formation. A binding domain may be the minimal number of amino acids required to retain binding affinity, or may be a larger fragment or derivative of the polypeptides listed in Table 7, columns 2 and 6.

In certain embodiments, the "bait" polypeptides of the ortholog complex are polypeptides categorized, for example, as a "Metabolism" protein in the MIPS database. In some embodiments, the "prey" protein of the complex is also a "Metabolism" protein, while in other embodiments the "prey" protein is, for example, an "Unclassified" protein (see Table 7). Other exemplary MIPS categories include, e.g., "Cell Growth/Cell Division/DNA Synthesis" proteins (see Table 2).

In a further aspect, the invention provides chimeric polypeptide complex that includes at least one yeast polypeptide and at least one human ortholog of the corresponding interacting yeast polypeptide. In one embodiment, there is provided a purified chimeric complex including a yeast "bait" polypeptide selected from the polypeptides recited in Table 7, column 1 and a human ortholog of the corresponding yeast "prey" polypeptide; the human ortholog is selected from the polypeptides recited in Table 7, column 6 (while the corresponding yeast "prey" proteins are recited in column 5). For example, with reference to Table 7, first row, in one embodiment, a chimeric protein containing YAL032C and P16118 is provided (P16118 is the human ortholog of corresponding yeast "prey" protein YLR345W).

In other embodiments, the complex contains a human ortholog of a yeast "bait" protein and a yeast "prey" protein. The yeast "prey" protein is selected from the polypeptides recited in Table 7, column 5, and the human ortholog of the corresponding yeast "bait" protein is selected from the polypeptides recited in Table 7, column 2 (while the corresponding yeast "bait" proteins themselves are recited in column 1). For example, with reference to Table 7, first row, in one embodiment, a chimeric protein containing Q13573 and YLR345W is provided (Q13573 is the human ortholog of corresponding yeast "bait" protein YAL032C).

In certain embodiments the first and second polypeptides of the chimeric complex are the polypeptides recited in Table 7, columns 1 and 6, or columns 2 and 5, respectively, while in other embodiments, the polypeptides of the chimeric complex contain the polypeptides recited in Table 7. Conservative variants of either polypeptide which retain binding specificity are within the scope of the invention, as are labeled forms of the chimeric complexes, and chimeric complexes of binding domains, as described above.

Chimeric Polypeptides, DNA, Vectors and Recombinant Cells

In a further aspect, the invention provides a chimeric polypeptide that includes sequences of two interacting proteins according to the invention. The interacting proteins can be, e.g., the interacting protein pairs disclosed in Tables 3–7, herein. Also included are chimeric polypeptides including multimers, i.e., sequences from two or more pairs of interacting proteins. An example of such a chimeric polypeptide is a polypeptide that includes amino acid sequences from ProPair 1a and 1b, and from ProPair 2a and 2b. The chimeric polypeptide includes a region of a first protein covalently linked, e.g. via peptide bond, to a region of a second protein. In certain embodiments, the second protein is a species ortholog of the first protein. In some embodiments, the chimeric polypeptide contains regions of first and second proteins from yeast, where the proteins are selected from the "bait" and corresponding "prey" proteins recited in Table 3, columns 1 and 4, respectively. In other embodiments, the chimeric polypeptide contains regions of first and second human ortholog proteins, where the proteins are selected from the "bait" and corresponding "prey" proteins recited in Table 7, columns 2 and 6, respectively (the yeast orthologs of these proteins are recited in columns 1 and 5, respectively). In still other embodiments, the chimeric polypeptide contains regions of a first protein from yeast, and a second human ortholog protein, where the yeast proteins are selected from the "bait" and corresponding "prey" proteins recited in Table 7, columns 1 and 5, respectively, while the human ortholog proteins are selected from the "bait" and corresponding "prey" proteins recited in Table 7, columns 2 and 6, respectively.

In some embodiments, the chimeric polypeptide(s) of the complex include(s) six or more amino acids of a first protein covalently linked to six or more amino acids of a second protein. In other embodiments, the chimeric polypeptide includes at least one binding domain of a first or second protein.

Preferably, the chimeric polypeptide includes a region of amino acids of the first polypeptide able to bind to a second polypeptide. Alternatively, or in addition, the chimeric polypeptide includes a region of amino acids of the second polypeptide able to bind to the first polypeptide.

Nucleic acid encoding the chimeric polypeptide, as well as vectors and cells containing these nucleic acids, are within the scope of the present invention. The chimeric polypeptides can be constructed by expressing nucleic acids encoding chimeric polypeptides using recombinant methods, described above, then recovering the chimeric polypeptides, or by chemically synthesizing the chimeric polypeptides. Host-vector systems that can be used to express chimeric polypeptides include, e.g.: (i) mammalian cell systems which are infected with vaccinia virus, adenovirus; (ii) insect cell systems infected with baculovirus; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

The expression of the specific proteins may be controlled by any promoter/enhancer known in the art including, e.g.: (i) the SV40 early promoter (see e.g., Bernoist & Chambon, *Nature* 290: 304–310 (1981)); (ii) the promoter contained within the 3'-terminus long terminal repeat of Rous Sarcoma Virus (see e.g., Yamamoto, et al., *Cell* 22: 787–797 (1980)); (iii) the Herpesvirus thymidine kinase promoter (see e.g., Wagner, et al., *Proc. Natl. Acad. Sci. USA* 78: 1441–1445 (1981)); (iv) the regulatory sequences of the metallothionein gene (see e.g., Brinster, et al., *Nature* 296: 39–42 (1982)); (v) prokaryotic expression vectors such as the β-lactamase promoter (see e.g., Villa-Kamaroff, et al., *Proc. Natl. Acad. Sci. USA* 75: 3727–3731 (1978)); (vi) the tac promoter (see e.g., DeBoer, et al., *Proc. Natl. Acad. Sci. USA* 80: 21–25 (1983)).

Plant promoter/enhancer sequences within plant expression vectors may also be utilized including, e.g.,: (i) the nopaline synthetase promoter (see e.g., Herrar-Estrella, et al., *Nature* 303: 209–213 (1984)); (ii) the cauliflower mosaic virus 35S RNA promoter (see e.g., Garder, et al., *Nuc. Acids Res.* 9: 2871 (1981)) and (iii) the promoter of the photosynthetic enzyme ribulose bisphosphate carboxylase (see e.g., Herrera-Estrella, et al., *Nature* 310: 115–120 (1984)).

Promoter/enhancer elements from yeast and other fungi (e.g., the Gal4 promoter, the alcohol dehydrogenase promoter, the phosphoglycerol kinase promoter, the alkaline phosphatase promoter), as well as the following animal transcriptional control regions, which possess tissue specificity and have been used in transgenic animals, may be utilized in the production of proteins of the present invention.

Other animal transcriptional control sequences derived from animals include, e.g.,: (i) the insulin gene control region active within pancreatic β-cells (see e.g., Hanahan, et al., *Nature* 315: 115–122 (1985)); (ii) the immunoglobulin gene control region active within lymphoid cells (see e.g., Grosschedl, et al., *Cell* 38: 647–658 (1984)); (iii) the albumin gene control region active within liver (see e.g., Pinckert, et al., *Genes and Devel.* 1: 268–276 (1987)); (iv) the myelin basic protein gene control region active within brain oligodendrocyte cells (see e.g., Readhead, et al., *Cell* 48: 703–712 (1987)); and (v) the gonadotrophin-releasing hormone gene control region active within the hypothalamus (see e.g., Mason, et al., *Science* 234: 1372–1378 (1986)).

The vector may include a promoter operably-linked to nucleic acid sequences which encode a chimeric polypeptide, one or more origins of replication, and optionally, one or more selectable markers (e.g., an antibiotic resistance gene). A host cell strain may be selected which modulates the expression of chimeric sequences, or modifies/processes the expressed proteins in a desired manner. Moreover, different host cells possess characteristic and specific mechanisms for the translational and post-translational processing and modification (e.g., glycosylation, phosphorylation, and the like) of expressed proteins. Appropriate cell lines or host systems may thus be chosen to ensure the desired modification and processing of the foreign protein is achieved. For example, protein expression within a bacterial system can be used to produce an unglycosylated core protein; whereas expression within mammalian cells ensures "native" glycosylation of a heterologous protein.

Antibodies Specific for Polypeptide Complexes

The invention further provides antibodies and antibody fragments (such as Fab or (Fab)2 fragments) that bind specifically to the complexes described herein. By "specifically binds" is meant an antibody that recognizes and binds to a particular polypeptide complex of the invention, but which does not substantially recognize or bind to other molecules in a sample, or to any of the polypeptides of the complex when those polypeptides are not complexed.

For example, a purified complex, or a portion, variant, or fragment thereof, can be used as an immunogen to generate antibodies that specifically bind the complex using standard techniques for polyclonal and monoclonal antibody preparation.

A full-length polypeptide complex can be used, if desired. Alternatively, the invention provides antigenic fragments of polypeptide complexes for use as immunogens. In some embodiments, the antigenic complex fragment includes at least 6, 8, 10, 15, 20, or 30 or more amino acid residues of a polypeptide. In one embodiment, epitopes encompassed by the antigenic peptide include the binding domains of the polypeptides, or are located on the surface of the protein, e.g., hydrophilic regions.

If desired, peptides containing antigenic regions can be selected using hydropathy plots showing regions of hydrophilicity and hydrophobicity. These plots may be generated by any method well known in the art, including, for example, the Kyte Doolittle or the Hopp Woods methods, either with or without Fourier transformation. See, e.g., Hopp and Woods, *Proc. Nat. Acad. Sci. USA* 78:3824–3828 (1981); Kyte and Doolittle, *J. Mol. Biol.* 157:105–142 (1982).

The term "antibody" as used herein refers to immunoglobulin molecules and immunologically active portions of immunoglobulin molecules, i.e., molecules that contain an antigen binding site that specifically binds (immunoreacts with) an antigen, such as a polypeptide complex. Such antibodies include, e.g.,polyclonal, monoclonal, chimeric, single chain, Fab and F(ab')2 fragments, and an Fab expression library. In specific embodiments, antibodies to human ortholog complexes.

Various procedures known within the art may be used for the production of polyclonal or monoclonal antibodies. For example, for the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed polypeptide complex. Alternatively, the immunogenic polypeptides or complex may be chemically synthesized, as discussed above. The preparation can further include an adjuvant. Various adjuvants used to increase the immunological response include, e.g., Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents. If desired, the antibody molecules directed against complex can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of a polypeptide complex. A monoclonal antibody composition thus typically displays a single binding affinity for a particular protein with which it immunoreacts. For preparation of monoclonal antibodies directed towards a particular complex, or polypeptide, any technique that provides for the production of antibody molecules by continuous cell line culture may be utilized. Such techniques include, e.g., the hybridoma technique (see Kohler & Milstein, *Nature* 256: 495–497 (1975)); the trioma technique; the human B-cell hybridoma technique (see Kozbor, et al., *Immunol Today* 4: 72 (1983)); and the EBV hybridoma technique to produce human monoclonal antibodies (see Cole, et al., In: *Monoclonal Antibodies and Cancer Therapy*, Alan R. Liss, Inc., (1985) pp. 77–96). If desired, human monoclonal antibodies may be prepared by using human hybridomas (see Cote, et al., *Proc. Natl. Acad. Sci. USA* 80: 2026–2030 (1983)) or by transforming human B-cells with Epstein Barr Virus in vitro (see Cole, et al., In: *Monoclonal Antibodies and Cancer Therapy*, supra).

Methods can be adapted for the construction of $F_{ab}$ expression libraries (see e.g., Huse, et al., *Science* 246: 1275–1281 (1989)) to allow rapid and effective identification of monoclonal $F_{ab}$ fragments with the desired specificity for the desired protein or derivatives, fragments, analogs or homologs thereof. Non-human antibodies can be "humanized" by techniques well known in the art. See e.g., U.S. Pat. No. 5,225,539. Antibody fragments that contain the idiotypes to a polypeptide or polypeptide complex may be produced by techniques known in the art including, e.g.: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Chimeric and humanized monoclonal antibodies against the polypeptide complexes, or polypeptides, described herein are also within the scope of the invention, and can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., *Science* 240: 1041–1043 (1988); Liu et al., *Proc. Nat. Acad. Sci. USA* 84: 3439–3443 (1987); Liu et al., *J. Immunol.* 139: 3521–3526 (1987); Sun et al., *Proc. Nat. Acad. Sci. USA* 84: 214–218 (1987); Nishimura et al., *Cancer Res.* 47: 999–1005 (1987); Wood et al., *Nature* 314: 446–449 (1985); Shaw et al., *J. Natl. Cancer Inst.* 80: 1553–1559 (1988); Morrison, *Science* 229: 1202–1207 (1985); Oi et al., *BioTechniques* 4: 214 (1986); U.S. Pat. No. 5,225,539; Jones et al., *Nature* 321: 552–525 (1986); Verhoeyan et al., *Science* 239: 1534 (1988); and Beidler et al., *J. Immunol.* 141: 4053–4060 (1988).

Methods for the screening of antibodies that possess the desired specificity include, e.g., enzyme-linked immunosorbent assay (ELISA) and other immunologically-mediated techniques known within the art. For example, selection of antibodies that are specific to a particular domain of a polypeptide complex is facilitated by generation of hybridomas that bind to the complex, or fragment thereof, possessing such a domain.

In certain embodiments of the invention, antibodies specific for the polypeptide complexes described herein may be used in various methods, such as detection of complex, and identification of agents which disrupt complexes. These methods are described in more detail, below. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

Polypeptide complex-specific, or polypeptide-specific antibodies, can also be used to isolate complexes using standard techniques, such as affinity chromatography or immunoprecipitation. Thus, the antibodies disclosed herein can facilitate the purification of specific polypeptide complexes from cells, as well as recombinantly produced complexes expressed in host cells.

Kits

In a specific embodiment, the invention provides kits containing a reagent, for example, an antibody described above, which can specifically detect a polypeptide complex, or a constituent polypeptide, described herein. Such kits can contain, for example, reaction vessels, reagents for detecting complex in sample, and reagents for development of detected complex, e.g. a secondary antibody coupled to a detectable marker. The label incorporated into the anti-complex, or anti-polypeptide antibody may include, e.g., a chemiluminescent, enzymatic, fluorescent, colorimetric or radioactive moiety. Kits of the present invention may be employed in diagnostic and/or clinical screening assays.

Pharmaceutical Compositions

The invention further provides pharmaceutical compositions of purified complexes suitable for administration to a subject, most preferably, a human, in the treatment of disorders involving altered levels of such complexes. Such preparations include a therapeutically-effective amount of a complex, and a pharmaceutically acceptable carrier. As utilized herein, the term "pharmaceutically acceptable" means approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

The therapeutic amount of a complex which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. [[However, suitable dosage ranges for intravenous administration of the complexes of the present invention are generally about 20–500 micrograms ($\mu$g) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

Various delivery systems are known and can be used to administer a pharmaceutical preparation of a complex of the invention including, e.g.: (i) encapsulation in liposomes, microparticles, microcapsules; (ii) recombinant cells capable of expressing the polypeptides of the complex; (iii) receptor-mediated endocytosis (see, e.g., Wu et al., *J. Biol. Chem.* 262: 4429–4432 (1987)); (iv) construction of a nucleic acid encoding the polypeptides of the complex as part of a retroviral or other vector, and the like.

Methods of administration include, e.g., intradermal, intramuscular, intraperitoneal, intravenous, subcutaneous, intranasal, epidural, and oral routes. The pharmaceutical preparations of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the pharmaceutical preparation into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the pharmaceutical preparation locally to the area in need of treatment; this may be achieved by, for example, and not by way of limitation, local infusion during surgery, topical application, by injection, by means of a catheter, by means of a suppository, or by means of an implant. In a specific embodiment, administration may be by direct injection at the site (or former site) of a malignant tumor or neoplastic or pre-neoplastic tissue.

Alternatively, pharmaceutical preparations of the invention may be delivered in a vesicle, in particular a liposome, (see, e.g., Langer, *Science* 249:1527–1533 (1990)) or via a controlled release system including, e.g., a delivery pump (see, e.g., Saudek, et al., *New Engl. J. Med.* 321: 574 (1989) and a semi-permeable polymeric material (see, e.g., Howard, et al., *J. Neurosurg.* 71: 105 (1989)). Additionally, the controlled release system can be placed in proximity of the therapeutic target (e.g., the brain), thus requiring only a fraction of the systemic dose. See, e.g., Goodson, In: *Medical Applications of Controlled Release*, 1984 (CRC Press, Bocca Raton, Fla.).

Screening, Diagnostic, and Therapeutic Methods

The invention further provides methods of identifying an agent which modulate formation or stability a polypeptide complex described herein. By modulate is meant to increase or decrease the rate at which the complex is assembled or dissembled, or to increase or decrease the stability of an assembled complex. Thus, an agent can be tested for its ability to disrupt a complex, or to promote formation or stability of a complex.

In one embodiment, the invention provides a method of identifying an agent that promotes disruption of a complex. The method includes providing a polypeptide complex, contacting the complex with a test agent, and detecting the presence of a polypeptide displaced from the complex. The presence of displaced polypeptide indicates the disruption of the complex by the agent. In some embodiments, the complex is a human ortholog complex, as described above, which includes "bait" and "prey" proteins selected from those recited in Table 7. In other embodiments, the complex contains at least one microtubule or microtubule-associated protein, as described above, and is selected from the complexes recited in Table 4. In other embodiments, the complex contains at least one heme biosynthesis protein, as described above, and is the complex recited in Table 5. In yet another embodiment, the complex contains at least one cell wall or cell wall-synthesis protein, as described above, and is selected from the complexes recited in Table 6. Agents which disrupt complexes of the invention may present novel modulators of cell processes and pathways in which the complexes participate. For example, agents which disrupt complexes involving microtubule proteins may be selected as potential anti-fungal therapeutics.

Any compound or other molecule (or mixture or aggregate thereof) can be used as a test agent. In some embodiments, the agent can be a small peptide, or other small molecule produced by e.g., combinatorial synthetic methods known in the art. Disruption of the complex by the test agent, e.g. binding of the agent to the complex, can be determined using art recognized methods, e.g., detection of polypeptide using polypeptide-specific antibodies, as described above. Bound agents can alternatively be identified by comparing the relative electrophoretic mobility of complexes exposed to the test agent to the mobility of complexes that have not been exposed to the test agent.

Agents identified in the screening assays can be further tested for their ability to alter and/or modulate cellular functions, particularly those functions in which the complex has been implicated. These functions include, e.g., control of cell-cycle progression; regulation of transcription; control of intracellular signal transduction, etc., as described in detail above.

In another embodiment, the invention provides methods for inhibiting the interaction of a polypeptide with a ligand, by contacting a complex of the protein and the ligand with an agent that disrupts the complex, as described above. In certain embodiments, the polypeptides are microtubule or microtubule-associated proteins, heme biosynthesis proteins, or cell wall or cell wall-synthesis proteins. In certain embodiments, the ligand is an interacting polypeptide, and the polypeptide and ligands are selected from those recited in Tables 4–6. Inhibition of complex formation allows for modulation of cellular functions and pathways in which the targeted complexes participate.

In another embodiment, the invention provides a method for identifying a polypeptide complex in a subject. The method includes the steps of providing a biological sample from the subject, detecting, if present, the level of polypeptide complex. In some embodiments, the complex includes a first polypeptide (a "bait" polypeptide) selected from the polypeptides recited in Table 7, column 2, and a second polypeptide ("prey" polypeptide) selected from the polypeptides recited in Table 7, column 6. Any suitable biological sample potentially containing the complex may be employed, e.g. blood, urine, cerebral-spinal fluid, plasma, etc. Complexes may be detected by, e.g., using complex-specific antibodies as described above. The method provides for diagnostic screening, including in the clinical setting, using, e.g., the kits described above.

In still another embodiment, the present invention provides methods for detecting a polypeptide in a biological sample, by providing a biological sample containing the polypeptide, contacting the sample with a corresponding polypeptide to form a complex under suitable conditions, and detecting the presence of the complex. A complex will form if the sample does, indeed, contain the first polypeptide. In some embodiments, the polypeptide being detecting is a "prey" protein selected from the polypeptides recited in Table 7, column 6, and is detected by complexing with the corresponding "bait" protein recited in Table 7, column 2. Conversely, in other embodiments the polypeptide being detected is the "bait" protein. Alternatively, a yeast "bait" or "prey" ortholog may be employed to form a chimeric complex with the polypeptide in the biological sample.

In still another embodiment, the invention provides methods for removing a first polypeptide from a biological sample by contacting the biological sample with the corresponding second peptide to form a complex under conditions suitable for such formation. The complex is then removed from the sample, effectively removing the first polypeptide. As with the methods of detecting polypeptide described above, the polypeptide being removed may be either a "bait" or "prey" protein, and the second corresponding polypeptide used to remove it may be either a yeast or human ortholog polypeptide.

Methods of determining altered expression of a polypeptide in a subject, e.g. for diagnostic purposes, are also provided by the invention. Altered expression of proteins involved in cell processes and pathways can lead to deleterious effects in the subject. Altered expression of a polypeptide in a given pathway leads to altered formation of complexes which include the polypeptide, hence providing a means for indirect detection of the polypeptide level. The method involves providing a biological sample from a subject, measuring the level of a polypeptide complex of the invention in the sample, and comparing the level to the level of complex in a reference sample having known polypeptide expression. A higher or lower complex level in the sample versus the reference indicates altered expression of either of the polypeptides that forms the complex. The detection of altered expression of a polypeptide can be use to diagnose a given disease state, and or used to identify a subject with a predisposition for a disease state. Any suitable reference sample may be employed, but preferably the test sample and the reference sample are derived from the same medium, e.g. both are urine, etc. The reference sample should be suitably representative of the level polypeptide expressed in a control population.

In a certain embodiment, the polypeptide complex contains a "bait" polypeptide selected from the polypeptides recited in Table 7, column 2, and a "prey" polypeptide selected from the polypeptides recited in Table 7, column 6.

The invention further provides methods for treating or preventing a disease or disorder involving altered levels of a polypeptide complex, or polypeptide, disclosed herein, by administering to a subject a therapeutically-effective amount of at least one molecule that modulates the function of the complex. As discussed above, altered levels of polypeptide complexes described herein may be implicated in disease states resulting from a deviation in normal function of the pathway in which a complex is implicated. For example, altered levels of the observed complex between YGR010Wp and YLR328Wp may be implicated in disruptions in arginine metabolism, leading to retinal atrophy, for example. In subjects with a deleteriously high level of complex, modulation may consist, for example, by administering an agent which disrupts the complex, or an agent which does not disrupt, but down-regulates, the functional activity of the complex. Alternatively, modulation in subjects with a deleteriously low level of complex may be achieved by pharmaceutical administration of complex, constituent polypeptide, or an agent which up-regulates the functional activity of complex. Pharmaceutical preparations suitable for administration of complex are described above.

In one embodiment, a disease or disorder involving altered levels of a polypeptide selected from the polypeptides recited in Table 7, column 2 or the corresponding polypeptides in column 4, is treated by administering a molecule that modulates the function of the polypeptide. In certain embodiments, the modulating molecule is the corresponding polypeptide, e.g. administering a "prey" protein corresponding to a "bait" protein modulates the latter by forming a complex with it.

The details of one or more embodiments of the invention are set forth in the description above. Although any methods and materials similar or equivalent to those described herein can be used in the practice of the present invention, the preferred methods and materials are now described. For example, additional interactions can be identified using other two-hybrid systems (i.e. using a LexA binding domain fusion or HIS3 as a reporter gene), including variables such as different protein domains or genomic activation domain libraries. Other features, objects, and advantages of the invention will be apparent from the description and from the claims.

The following examples are presented in order to more fully illustrate the preferred embodiments of the invention. These examples should in no way be construed as limiting the scope of the invention, as defined by the appended claims.

EXAMPLE 1

Cloning of S. Cerevisiae Open-reading Frames 6144 potential yeast open-reading frames (ORFs) have been previously described. See Goffeau et al., supra. These ORFs were amplified by PCR as full-length fragments, and each fragment was fused to sequences encoding the Gal4 DNA binding domain and the Gal4 activation domain by gap-repair cloning into the vectors pOBD2 and pOAD. PCR amplified products of the 6144 yeast ORFs were made by amplification of yeast cDNA using 70 oligonucleotide primers to allow recombination with centromeric plasmids pOBD2 and pOAD. See Hudson et al., Genome Res 7: 1169 (1997). The yeast strains used were YULH (MATa ura3-52 trp1 lys2 his3 leu2 gal4 gal80 GAL1-URA3 GAL1-LacZ) for the Gal4 binding domain fusion in pOBD2 and N106r (MATα ura3-52 his3 ade2 trp1 leu2 gal4 gal80 cyh2 lys2::GAL1-HIS3 ura3::GAL1-LacZ) for the Gal4 AD fusion in pOAD. Yeast transformations were performed in a 96-well format using the lithium acetate procedure. See Ito et al., J. Bacteriol. 153: 163 (1983). Five µl from individual transformations were grown on selective media lacking leucine (Sc-Leu) or tryptophan (Sc-Trp) for two days and grown at 30° C. Patches of transformants were manually transferred into individual wells on micro-assay plates, to generate 64 barcoded 96-well plates for further use.

Of the 6144 ORFs, 5345 (87%) were successfully cloned into both plasmids (Table 1). Transformants from the Gal4 activation domain array were pooled to form an activation domain library. As yeast strains of opposite mating type were used to generate the two arrays, each binding domain fusion transformant was mated in duplicate to the activation domain library, and diploid cells that expressed interacting pairs were selected. Mating reactions were performed on 96-well filter plates (Millipore MAHV S45) by mixing $10^7$ MATa cells (Gal4 binding domain fusion) with $5\times10^6$ MATα cells (activation domain library) from liquid cultures in complete media (YPAD). After filtration, the 96-well filter plates were incubated overnight at 30° C. on rectangular YPAD solid media plates. Cells were collected from each filter with sterile water and the diploids containing potential interactors were selected on media lacking uracil and simultaneously screened by the addition of X-gal by incubating 4 days at 30° C. Each mating generated $5\times10^5$ to $10^6$ diploids per well, and was performed in duplicate to insure the reproducibility of the results. Up to 12 blue colonies were picked per mating and submitted for PCR and sequencing. A total of 8676 blue colonies were picked from the screen, 6909 (80%) passed PCR, sequencing, vector trimming, and annotation quality control, and 6215 (72%) passed interaction quality control.

To conduct transformation and mating reactions on such a large scale in a timely fashion, 96-well assay plates and a semi-automated Zymark® work station were used throughout the cloning and screening procedures. Sample handling and manipulation during the screens were tracked by computer, and data analysis was carried out using web-based software developed at CuraGen (GeneScape®). The final product of the screening process was a collection of 96-well plates of diploid clones. The activation domain fusion plasmids were sequenced to identify the yeast ORF. The resulting sequences were compared to the yeast sequence database using Blast2. See Altschul et al., J. Mol. Biol. 215: 403 (1990). Using these results, a list of interactors was obtained, as discussed above (see Table 3).

Results from this screen were also compared with a compilation of previously described interactions. Thirty-one protein pairs identified in the present screen were previously reported as two-hybrid interactions, and an additional 18 pairs confirmed interactions previously identified by biochemical assays (co-immunoprecipitation, copurification, affinity column). See MIPS Yeast Genome Database (MYGD) Functional Catalogue, supra.; Mewes et al., supra. Thus, 49 out of the 692 interactions identified in this screen overlap the approximately 700 interactions in S. cerevisiae reported in the literature. See id.

The limited overlap between the results described herein and the literature (7%) can be attributed to specifics of the screen: the exclusive use of full-length proteins as both binding and activation domain fusions and the version of the two-hybrid system used, which includes Gal4 as the binding domain fusion protein, centromeric plasmids, and a stringent reporter gene (URA3). Each of these components can affect the sensitivity of the assay. See Legrain et al., Nucl. Acid. Res. 22: 3241 (1994).

SEQUENCE LISTING

The patent contains a lengthy "Sequence Listing" section. A copy of the "Sequence Listing" is available in electronic form from the USPTO web site (http://seqdata.uspto.gov/sequence.html?DocID=5917994B9). An electronic copy of the "Sequence Listing" will also be available from the USPTO upon request and payment of the fee set forth in 37 CFR 1.19(b)(3).

We claim:

1. A purified protein complex comprising a first polypeptide and a second polypeptide, wherein said complex comprises the amino acid sequences of a first polypeptide (SMI1, SEQ ID NO: 359), and a second polypeptide (BAS1, SEQ ID NO: 518), denoted as ProPair 267a–267b.

2. The complex of claim 1, wherein said second polypeptide is labeled with a detectable substance.

3. The complex of claim 1, wherein said second polypeptide is labeled with a detectable substance.

4. The complex of claim 2, wherein said second polypeptide is labeled with a detectable substance.

5. A composition comprising the complex of claim 1 and a pharmaceutically acceptable carrier.

* * * * *

UNITED STATES PATENT AND TRADEMARK OFFICE
CERTIFICATE OF CORRECTION

PATENT NO.    : 6,753,314 B1  
DATED         : June 22, 2004  
INVENTOR(S)   : Loic Giot and Traci Mansfield It is certified that error appears in the above-identified patent and that said Letters Patent is hereby corrected as shown below:

<u>Column 125,</u>  
Line 20, that portion of the claim reading "second" should read -- first --.

Signed and Sealed this

Fifth Day of April, 2005

JON W. DUDAS  
*Director of the United States Patent and Trademark Office*